United States Patent
Bandyopadhyay

(10) Patent No.: US 12,098,138 B2
(45) Date of Patent: Sep. 24, 2024

(54) SUBSTITUTED PYRIDINYL AZETIDINONE DERIVATIVES FOR USE IN TREATING CANCER AND OTHER DISEASES

(71) Applicant: The Board of Regents of the University of Texas System, Austin, TX (US)

(72) Inventor: Debasish Bandyopadhyay, Edinburg, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 843 days.

(21) Appl. No.: 17/058,740

(22) PCT Filed: May 24, 2019

(86) PCT No.: PCT/US2019/033996
§ 371 (c)(1),
(2) Date: Nov. 25, 2020

(87) PCT Pub. No.: WO2019/227040
PCT Pub. Date: Nov. 28, 2019

(65) Prior Publication Data
US 2021/0214341 A1    Jul. 15, 2021

Related U.S. Application Data

(60) Provisional application No. 62/676,603, filed on May 25, 2018.

(51) Int. Cl.
C07D 401/14    (2006.01)
C07D 401/04    (2006.01)
C07F 7/08      (2006.01)

(52) U.S. Cl.
CPC ......... *C07D 401/14* (2013.01); *C07D 401/04* (2013.01); *C07F 7/0812* (2013.01)

(58) Field of Classification Search
CPC .... C07D 401/14; C07D 401/04; C07F 7/0812
See application file for complete search history.

(56) References Cited

U.S. PATENT DOCUMENTS

| | | |
|---|---|---|
| 6,225,463 B1 | 5/2001 | De Vos et al. |
| 6,946,458 B2 | 9/2005 | Turos |
| 7,026,472 B2 | 4/2006 | Dou et al. |
| 7,635,693 B2 | 12/2009 | Dou et al. |
| 8,633,238 B2 | 1/2014 | Chiang et al. |
| 8,822,679 B2 | 9/2014 | Stoltz et al. |
| 8,946,409 B2 | 2/2015 | Becker et al. |
| 2005/0107430 A1 | 5/2005 | Banik et al. |
| 2010/0035856 A1 | 2/2010 | Mertin et al. |
| 2014/0066423 A1 | 3/2014 | Becker et al. |

FOREIGN PATENT DOCUMENTS

| | | |
|---|---|---|
| WO | WO 2012/103456 | 8/2012 |
| WO | WO 2019/227040 | 11/2019 |

OTHER PUBLICATIONS

Chemical Reviews, 1996, vol. 96, No. 8, p. 3152.*
Banik et al., "Asymmetric synthesis of anticancer β-lactams via Staudinger reaction: Utilization of chiral ketene from carbohydrate," *European Journal of Medicinal Chemistry*, 45:846-848, 2010.
Banik, et al., "Novel Anticancer β-Lactams," in Topics in Heterocyclic Chemistry: Heterocyclic Scaffolds I, Bimal K. Banik, Ed., 22:349-373, 2010.
Banik, et al., "Stereocontrolled synthesis of anticancer β-lactams via the Staudinger reaction," *Bioorganic & Medicinal Chemistry*, 13:3611-3622, 2005.
Banik, et al., "Stereoselective synthesis of β-lactams with polyaromatic imines: Entry into new and novel anticancer agents," *J. Med. Chem.*, 46:12-15, 2003.
Banik, et al., "Stereospecific glycosylation via Ferrier Rearrangement for optical resolution," *J. Org. Chem.*, 59(17):4714-4716, 1994.
Banik, et al., "Synthesis of anticancer β-lactams: mechanism of action," *Bioorganic & Medicinal Chemistry*, 12:2523-2528, 2004.
Banik, et al., "Unprecedented stereoselectivity in the Staudinger reaction with polycyclic aromatic imines," *Tetrahedron Letters*, 41:6551-6554, 2000.
Banik, et al., "Versatile β-lactam synthons: enantiospecifc synthesis of (−)-polyoxamic acid," *J. Org. Chem.*, 58(2):307-309, 1993.
Banik, In: β-*Lactams: Synthesis, Stereochemistry, Synthon, and Biological Evaluation*, Bentham Sci. Publ. Ltd., vol. 11, 2004.

(Continued)

*Primary Examiner* — Kamal A Saeed
(74) *Attorney, Agent, or Firm* — Parker Highlander PLLC

(57) ABSTRACT

Disclosed herein are compounds of the formula: as well as analogs thereof, wherein the variables are defined herein. Also provided are pharmaceutical compositions thereof. The compounds and compositions provided herein may be used for the treatment or prevention of diseases or disorders, including but not limited to cancer (e.g., pancreatic cancer), including drug-resistant cancers, such as gemcitabine-resistant pancreatic cancer or KRAS dependent tumors.

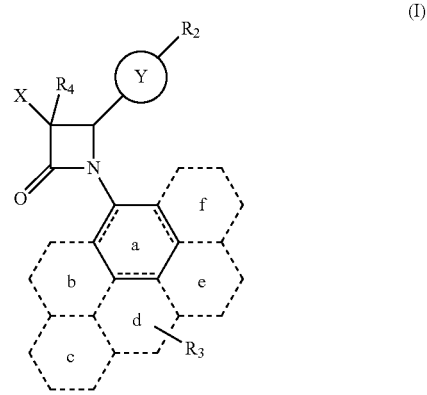

(I)

15 Claims, 20 Drawing Sheets

(56) References Cited

OTHER PUBLICATIONS

Bose, et al., "Polyhydroxy Amino Acid Derivatives via β-Lactams Using Enantiospecific Approaches and Microwave Techniques," *Tetrahedron Symposium*, 56:5603-5619, 2000.

Bose, et al., In: *The Amide Linkage: Selected Structural Aspects in Chemistry, Biochemistry, and Material Science*, Greenberg, et al., (Eds.), Wiley-Interscience, NY, 7:157-214, 2000.

Burnett, "β-Lactam Cholesterol Absorption Inhibitors," *Curr. Med. Chem.* 11:1873-1887, 2004.

Burnett, et al., "2-Azetidinones as Inhibitors of Cholesterol Absorption," *J. Med. Chem.*, 37(12):1733-1736, 1994.

Buynak, "The Discovery and Development of Modified Penicillin- and Cephalosporin-Derived β-Lactamase Inhibitors," *Curr. Med. Chem.*, 11:1951-1964, 2004.

Clader, "The Discovery of Ezetimib: A View from Outside the Receptor," *J. Med. Chem.*, 47(1):1-9, 2004.

Clader, et al., "2-Azetidinone Cholesterol Absorption Inhibitors: Structure-Activity Relationships on the Heterocyclic Nucleus," *J. Med. Chem.*, 39:3684-3693, 1996.

Cox et al., "Ras Family Signaling: Therapeutic Targeting", *Cancer Biology & Therapy*, 1(6) 599-606, 2002.

Finke et al., "Orally Active β-Lactam Inhibitors of Human Leukocyte Elastase. 3. Stereospecific Synthesis and Structure-Activity Relationships for 3,3-Dialkylazetidin-2-ones," *J. Med. Chem.*, 38:2449-2462, 1995.

Furuya et al., "Catalysis for fluorination and trifluoromethylation," *Nature*, 473(7348):470-477, 2011.

Garcia et al.; "IER3 supports KRAS G12D-dependent pancreatic cancer development by sustaining ERK1/2 phosphorylation," *J. Clin. Invest.*, 124(11):4709-4722, 2014.

Georg and Ravikumar, In: *The Organic Chemistry of β-Lactams*, VCH publishers, NY, 1992.

Glazer et al., "Noninvasive Radiofrequency Field Destruction of Pancreatic Adenocarcinoma Xenografts Treated with Targeted Gold Nanoparticles," *Clin Cancer Res.*, 16(23):5712-5721, 2010.

Johnson et al., "In vitro tumorsphere formation assays," *Bio. Protoc.*, 3(3): e325, 2013.

Kidwai et al., "Synthetic Strategies and Medicinal Properties of β-Lactams," *Curr. Med. Chem.*, 6:195-215, 1999.

Manhas et al., "Vinyl-β-lactams as Efficient Synthons. Eco-friendly Approaches via Microwave Assisted Reactions," *Tetrahedron, Symposium*, 56:5587-5601, 2000.

Mazur et al., "SMYD3 links lysine methylation of MAP3K2 to Ras-driven cancer," *Nature*, 510(7504):283-287, 2014.

Ojima, "Recent Advances in the β-Lactam Synthon Method," *Acc. Chem. Res.*, 28(9):383-389, 1995.

Park et al., "Metabolism of Fluorine-containing Drugs," *Annu. Rev. Pharmacol. Toxicol.*, 41(1):443-470, 2001.

PCT International Search Report and Written Opinion issued in International Application No. PCT/US2019/033996, dated Aug. 26, 2019.

PCT International Search Report and Written Opinion issued in International Application No. PCT/US2012/022935, dated Aug. 24, 2012.

Southgate et al., In: *Recent Progress in the Chemical Synthesis of Antibiotics and Related Microbial Products*, Lukacs (Ed.), Springer-Verlag, Berlin, 621(2), 1993.

Stadel et al., "TRAIL-Induced Apoptosis is Preferentially Mediated via TRAIL Receptor 1 in Pancreatic Carcinoma Cells and Profoundly Enhanced by XIAP Inhibitors," *Clin Cancer Res.*, 16(23):5734-5749, 2010.

STN Database entry for CAS Registry No. 1135236-18-8, dated Apr. 16, 2009.

Suffness, In: *Taxol Science and Applications*, CRC Press, Boca Raton, FL, 1995.

Uprety et al., "KRAS: From undruggable to a druggable Cancer Target", Cancer Treatment Reviews, 89(102070):1-14, 2020.

Cannon, "Chapter Sixteen in Burger's Medicinal Chemistry and Drug Discovery," Sixth Edition, vol. 1: Drug Discovery, Wiley & Sons, Inc., 687-714, 2003.

\* cited by examiner

SUBSTITUTED PYRIDINYL AZETIDINONE DERIVATIVES FOR USE IN TREATING CANCER AND OTHER DISEASES

This application is a national phase application under 35 U.S.C. § 371 of International Application No. PCT/US2019/033996, filed May 24, 2019, which claims the benefit of U.S. Provisional Application No. 62/676,603, filed May 25, 2018, the entirety of which are incorporated herein by reference.

BACKGROUND OF THE INVENTION

I. Field of the Invention

The present disclosure relates generally to the fields of chemistry, biology and medicine. More particularly, it concerns substituted pyridinyl azetidinone derivatives, compositions, and methods for the treatment and prevention of diseases such as cancer (e.g., pancreatic cancer), including drug-resistant cancers, such as gemcitabine-resistant pancreatic cancer or KRAS dependent tumors.

II. Description of Related Art

Cancers figure among the leading causes of death worldwide, accounting for 8.2 million deaths in 2012. It is anticipated that annual cancer cases will rise from 14 million in 2012 to 22 within the next two decades. Although treatments like radiotherapy, immunotherapy, hormone therapy or gene therapy are used extensively, chemotherapy continues to play a crucial role in the treatment of cancer. Based on the variety of cell lines, more than 400 different types of cancers are known and some of these are drug-resistant where the rate of prognosis (survival of cancer patients) is very low. Effectively, there is no medicine in the market for drug-resistant cancers.

Pancreatic cancer is the third leading cause of cancer-related death for both men and women in the United States and is the only major cancer with a 5-year relative survival rate in the single digits, at just 7.7%. While overall cancer incidence and death rates are declining, the incidence and death rates for pancreatic cancer are increasing dangerously. According to the Texas Department of State Health Services, in Texas 3,080 new pancreatic cancer patients were diagnosed and 2664 pancreatic cancer patients died in the first eight months (January-August) of 2016. It is a matter of serious concern that pancreatic cancer is projected to move past colorectal cancer to become the second leading cause of cancer-related death in the United States around 2020. The justifications behind this estimation are: (i) in comparison to other cancers, pancreatic cancer can progress very quickly from stage I (localized within the pancreas) to stage IV (metastatic disease) in an average of 1.3 years; (ii) currently, there are no proven biomarkers, or clues detectable in the blood or other bodily fluids that could indicate the presence of a pancreatic tumor; (iii) only fewer than 20% of pancreatic cancer cases are diagnosed that meet the criteria for surgical intervention (often the Whipple procedure) although the disease recurs in approximately 80% of these surgical patients; (iv) for non-surgical patients (not suitable for surgery), chemotherapy (sometimes along with radiation) is typically offered but is not considered curative at all; (v) around 95% of pancreatic tumors are driven by mutations in KRAS (K-ras or Ki-ras) gene, which signifies a very aggressive and treatment-resistant tumor (Mazur et al., 2014 and Garcia et al., 2014). Mutated KRAS has been dubbed "undruggable," and it is prevalent in five drug-resistant pancreatic cancers that include HS 766T, CaPan-2, HPAC, HPAF-II and PANC-1. Currently there is NO effective treatment (surgery, chemotherapy, radiotherapy, immunotherapy; either individual or in combination) for these five drug-resistant pancreatic cancers; (vi) since 1974, only four drugs have been approved by the U.S. Food & Drug Administration (FDA) to treat pancreatic cancer. These are (a) gemcitabine (Gemzar®) in 1996, (b) erlotinib (Tarceva®) in 2005, (c) albumin-bound paclitaxel (Abraxane®) in 2013, and (d) irinotecan liposome injection (Onivyde™) in 2015. Unfortunately, none of these four drugs is effective against the aforementioned drug-resistant pancreatic adenocarcinoma. For example, the widely used anti-pancreatic cancer drug gemcitabine has an average $IC_{50}$ value against drug-resistant pancreatic cancer cell lines that range from 16 µM to >50 µM. Accordingly, identifying and developing therapies that may be used to treat this disease would be highly desirable.

β-lactam derivatives have many medicinal applications (Southgate et al., 1993; Kidwai et al., 1999; Bose et al., 2000; Banik, 2004). The need for potent β-lactam antibiotics and effective β-lactamase inhibitors has challenged chemists to design novel β-lactams (Buynak, 2004). These compounds have served as useful in the preparation of many heterocyclics of medicinal significance (Manhas et al., 2000; Bose et al., 2000; Ojima, 1995; Banik et al., 1994; Banik et al., 1993). Hydroxy β-lactam derivatives have been used as the starting materials in the semi synthesis of paclitaxel (Taxol) and docetaxel (Taxotere) (Suffness, 1995). The clinical use of β-lactams as therapeutic agents for lowering plasma cholesterol levels has been published (Clader et al., 1996; Burnett et al., 1994; Burnett, 2004; Clader, 2004). The biological activities of β-lactams against human leukocyte elastase have also been reported (Finke et al., 1995). The biological activites of a promising pyridinyl β-lactam derivative, TX-262, was reported in U.S. Pat. No. 8,946,409 and PCT Pub. WO 2012/103456. Developing new β-lactams analogs, especially ones with potent anti-cancer properties against pancreatic tumors are driven by mutations in KRAS gene, would be highly desirable.

SUMMARY OF THE INVENTION

The present disclosure provides novel compounds β-lactam derivatives with potent anti-cancer properties. Methods for their use for the treatment of disease, including pancreatic cancer, and methods of their manufacture are also disclosed herein.

In some aspects, the present disclosure provides compounds of the formula:

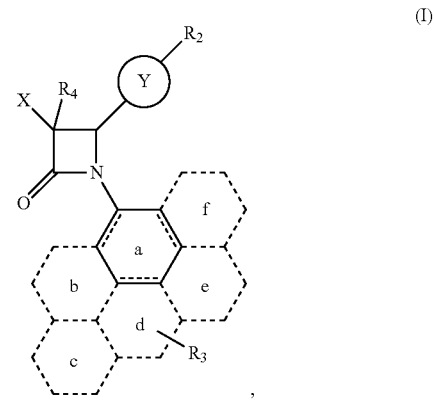

wherein:
Y is arenediyl$_{(C\leq12)}$, heteroarenediyl$_{(C\leq12)}$, substituted arenediyl$_{(C\leq12)}$, or substituted heteroarenediyl$_{(C\leq12)}$;
X is —OS(O)$_2$R$_1$, —S(O)$_2$NH$_2$, —C(O)NH$_2$ or guanidinyl, wherein:
R$_1$ is hydrogen, hydroxy, amino, or isocyanyl; or
alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, alkylamino$_{(C\leq12)}$, dialkylamino$_{(C\leq12)}$, heterocycloalkyl$_{(C\leq12)}$, or a substituted version of any of these groups;
R$_2$ is halo, hydroxy, or amino; or
alkoxy$_{(C\leq12)}$, acyloxy$_{(C\leq12)}$, alkylamino$_{(C\leq12)}$, dialkylamino$_{(C\leq12)}$, or a substituted version of any of these groups;
R$_3$ and R$_4$ are each independently:
amino, azido, cyano, halo, hydrogen, or hydroxy; or
alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, aryloxy$_{(C\leq12)}$, aralkoxy$_{(C\leq12)}$, acyloxy$_{(C\leq12)}$, alkylamino$_{(C\leq12)}$, dialkylamino$_{(C\leq12)}$, amido$_{(C\leq12)}$, or a substituted version of any of these groups; and
rings b, c, d, e, and f, if present, are aromatic;
or a pharmaceutically acceptable salt or tautomer thereof.

In some embodiments, the compound is further defined as:

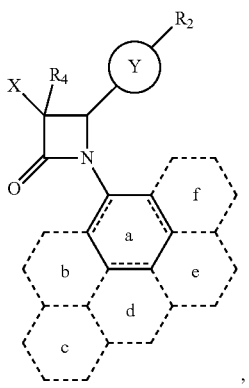

(II)

wherein:
Y is arenediyl$_{(C\leq12)}$, heteroarenediyl$_{(C\leq12)}$, substituted arenediyl$_{(C\leq12)}$, or substituted heteroarenediyl$_{(C\leq12)}$;
X is —OS(O)$_2$R$_1$, —S(O)$_2$NH$_2$, —C(O)NH$_2$ or guanidinyl, wherein:
R$_1$ is hydrogen, hydroxy, amino, or isocyanyl; or
alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, alkylamino$_{(C\leq12)}$, dialkylamino$_{(C\leq12)}$, heterocycloalkyl$_{(C\leq12)}$, or a substituted version of any of these groups;
R$_2$ is halo, hydroxy, or amino; or
alkoxy$_{(C\leq12)}$, acyloxy$_{(C\leq12)}$, alkylamino$_{(C\leq12)}$, dialkylamino$_{(C\leq12)}$, or a substituted version of any of these groups;
R$_4$ is amino, azido, cyano, halo, hydrogen, or hydroxy; or
alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, aryloxy$_{(C\leq12)}$, aralkoxy$_{(C\leq12)}$, acyloxy$_{(C\leq12)}$, alkylamino$_{(C\leq12)}$, dialkylamino$_{(C\leq12)}$, amido$_{(C\leq12)}$, or a substituted version of any of these groups; and
rings b, c, d, e, and f, if present, are aromatic;
or a pharmaceutically acceptable salt or tautomer thereof.

In further embodiments, the compounds are further defined as:

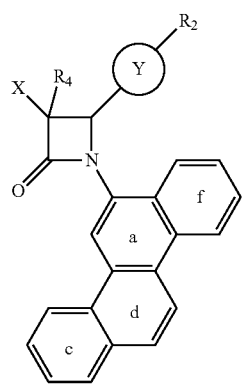

(III)

wherein:
Y is arenediyl$_{(C\leq12)}$, heteroarenediyl$_{(C\leq12)}$, substituted arenediyl$_{(C\leq12)}$, or substituted heteroarenediyl$_{(C\leq12)}$;
X is —OS(O)$_2$R$_1$, —S(O)$_2$NH$_2$, —C(O)NH$_2$ or guanidinyl, wherein:
R$_1$ is hydrogen, hydroxy, amino, or isocyanyl; or
alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, alkylamino$_{(C\leq12)}$, dialkylamino$_{(C\leq12)}$, heterocycloalkyl$_{(C\leq12)}$, or a substituted version of any of these groups;
R$_2$ is halo, hydroxy, or amino; or
alkoxy$_{(C\leq12)}$, acyloxy$_{(C\leq12)}$, alkylamino$_{(C\leq12)}$, dialkylamino$_{(C\leq12)}$, or a substituted version of any of these groups; and
R$_4$ is amino, azido, cyano, halo, hydrogen, or hydroxy; or
alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, aryloxy$_{(C\leq12)}$, aralkoxy$_{(C\leq12)}$, acyloxy$_{(C\leq12)}$, alkylamino$_{(C\leq12)}$, dialkylamino$_{(C\leq12)}$, amido$_{(C\leq12)}$, or a substituted version of any of these groups;
or a pharmaceutically acceptable salt or tautomer thereof.

In still further embodiments, the compounds are further defined as:

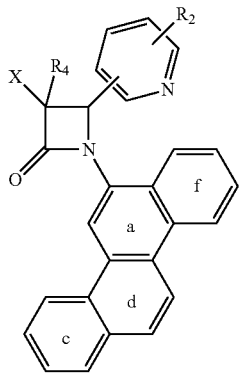

(IV)

wherein:
X is —OS(O)$_2$R$_1$, —S(O)$_2$NH$_2$, —C(O)NH$_2$ or guanidinyl, wherein:
R$_1$ is hydrogen, hydroxy, amino, or isocyanyl; or
alkyl$_{(C \leq 12)}$, cycloalkyl$_{(C \leq 12)}$, alkenyl$_{(C \leq 12)}$, cycloalkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, alkylamino$_{(C \leq 12)}$, dialkylamino$_{(C \leq 12)}$, heterocycloalkyl$_{(C \leq 12)}$, or a substituted version of any of these groups;
R$_2$ is halo, hydroxy, or amino; or
alkoxy$_{(C \leq 12)}$, acyloxy$_{(C \leq 12)}$, alkylamino$_{(C \leq 12)}$, dialkylamino$_{(C \leq 12)}$, or a substituted version of any of these groups; and
R$_4$ is amino, azido, cyano, halo, hydrogen, or hydroxy; or
alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, acyloxy$_{(C \leq 12)}$, alkylamino$_{(C \leq 12)}$, dialkylamino$_{(C \leq 12)}$, amido$_{(C \leq 12)}$, or a substituted version of any of these groups;
or a pharmaceutically acceptable salt or tautomer thereof.

In still further embodiments, the compounds are further defined as:

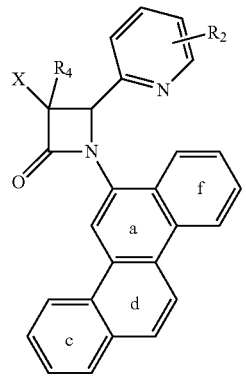

(V)

wherein:
X is —OS(O)$_2$R$_1$, —S(O)$_2$NH$_2$, —C(O)NH$_2$ or guanidinyl, wherein:
R$_1$ is hydrogen, hydroxy, amino, or isocyanyl; or
alkyl$_{(C \leq 12)}$, cycloalkyl$_{(C \leq 12)}$, alkenyl$_{(C \leq 12)}$, cycloalkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, alkylamino$_{(C \leq 12)}$, dialkylamino$_{(C \leq 12)}$, heterocycloalkyl$_{(C \leq 12)}$, or a substituted version of any of these groups;
R$_2$ is halo, hydroxy, or amino; or
alkoxy$_{(C \leq 12)}$, acyloxy$_{(C \leq 12)}$, alkylamino$_{(C \leq 12)}$, dialkylamino$_{(C \leq 12)}$, or a substituted version of any of these groups; and
R$_4$ is amino, azido, cyano, halo, hydrogen, or hydroxy; or
alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, acyloxy$_{(C \leq 12)}$, alkylamino$_{(C \leq 12)}$, dialkylamino$_{(C \leq 12)}$, amido$_{(C \leq 12)}$, or a substituted version of any of these groups;
or a pharmaceutically acceptable salt or tautomer thereof.

In yet further embodiments, the compounds are further defined as:

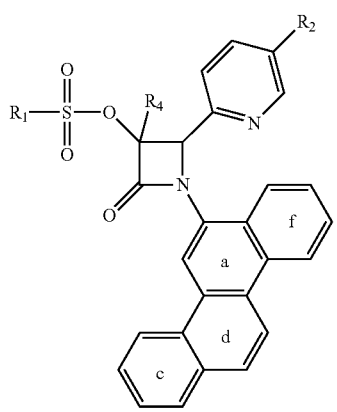

(VI)

wherein:
R$_1$ is hydrogen, hydroxy, amino, or isocyanyl; or
alkyl$_{(C \leq 12)}$, cycloalkyl$_{(C \leq 12)}$, alkenyl$_{(C \leq 12)}$, cycloalkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, alkylamino$_{(C \leq 12)}$, dialkylamino$_{(C \leq 12)}$, heterocycloalkyl$_{(C \leq 12)}$, or a substituted version of any of these groups;
R$_2$ is halo, hydroxy, or amino; or
alkoxy$_{(C \leq 12)}$, acyloxy$_{(C \leq 12)}$, alkylamino$_{(C \leq 12)}$, dialkylamino$_{(C \leq 12)}$, or a substituted version of any of these groups; and
R$_4$ is amino, azido, cyano, halo, hydrogen, or hydroxy; or
alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, acyloxy$_{(C \leq 12)}$, alkylamino$_{(C \leq 12)}$, dialkylamino$_{(C \leq 12)}$, amido$_{(C \leq 12)}$, or a substituted version of any of these groups;
or a pharmaceutically acceptable salt or tautomer thereof.

In some embodiments, Y is heteroarenediyl$_{(C \leq 12)}$. In some embodiments, $R_2$ is halo, such as fluoro. In some embodiments, $R_4$ is hydrogen. In some embodiments, X is —OS(O)$_2$R$_1$. In some embodiments, $R_1$ is hydrogen, hydroxy, amino, or isocyanyl. In further embodiments, $R_1$ is isocyanyl. In other embodiments, $R_1$ is alkyl$_{(C \leq 12)}$, cycloalkyl$_{(C \leq 12)}$, alkenyl$_{(C \leq 12)}$, cycloalkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, alkylamino$_{(C \leq 12)}$, dialkylamino$_{(C \leq 12)}$, heterocycloalkyl$_{(C \leq 12)}$, or a substituted version of any of these groups. In further embodiments, $R_1$ is alkyl$_{(C \leq 12)}$, cycloalkyl$_{(C \leq 12)}$, aryl$_{(C \leq 12)}$, dialkylamino$_{(C \leq 12)}$, heterocycloalkyl$_{(C \leq 12)}$, or a substituted version of any of these groups. In still further embodiments, $R_1$ is methyl, 2,2,2-trifluoroethyl, 3-cyanoazetidine, cyclobutyl, isopropyl(methyl)amino, cyclopropyl, 4-methylpiperizinyl, 2-(trimethylsilyl)ethyl, pyrrolidinyl, dimethylamino, or tolyl.

In some embodiments, the carbon atom 3 of the following ring portion of the compound is in the R conformation:

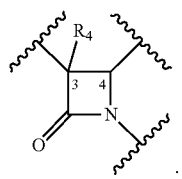

In other embodiments, the carbon atom 3 of the following ring portion of the compound is in the S conformation:

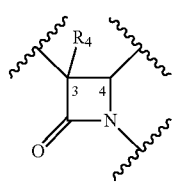

In some embodiments, the carbon atom 4 of the following ring portion of the compound is in the R conformation:

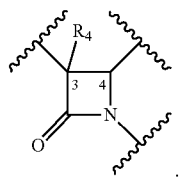

In other embodiments, carbon atom 4 of the following ring portion of the compound is in the S conformation:

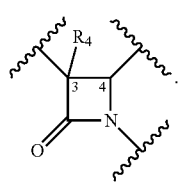

In some embodiments, the compound is further defined as:

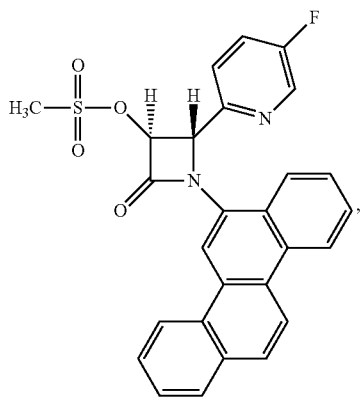

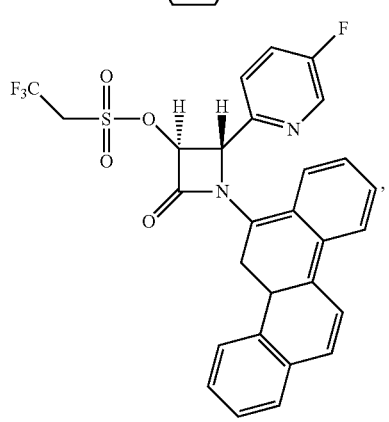

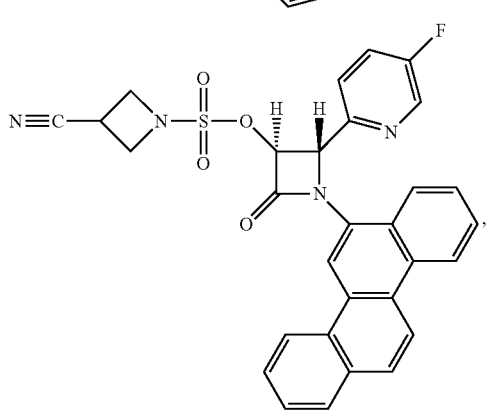

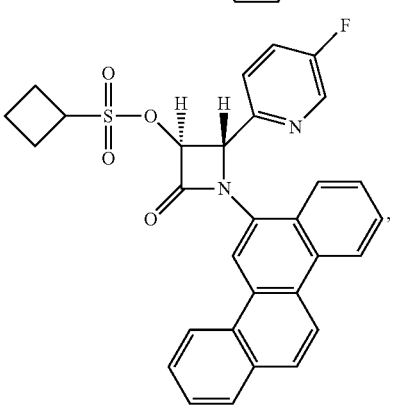

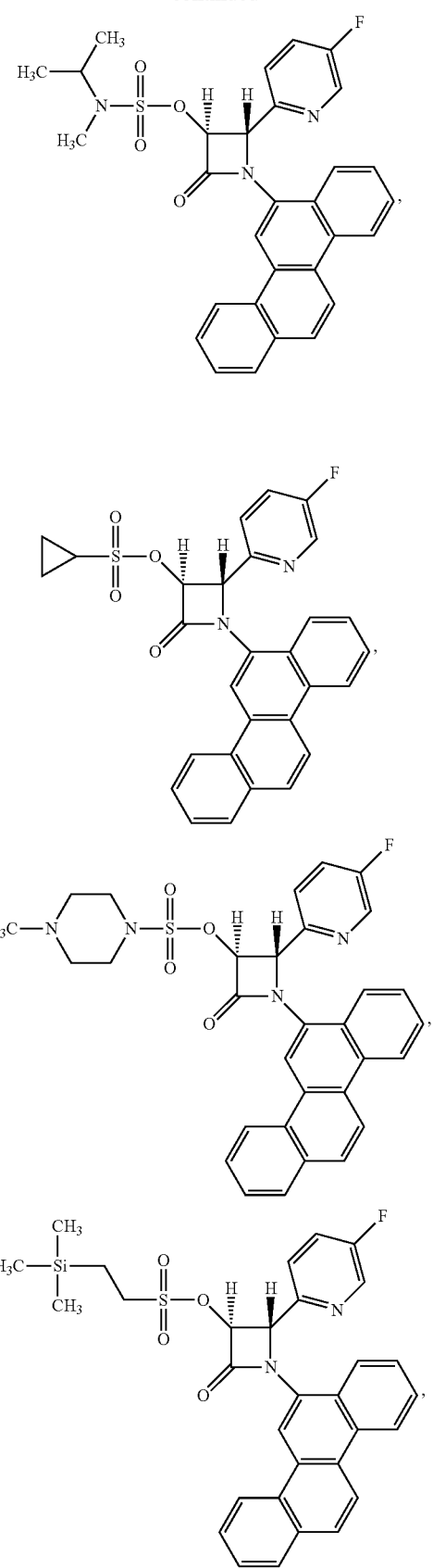
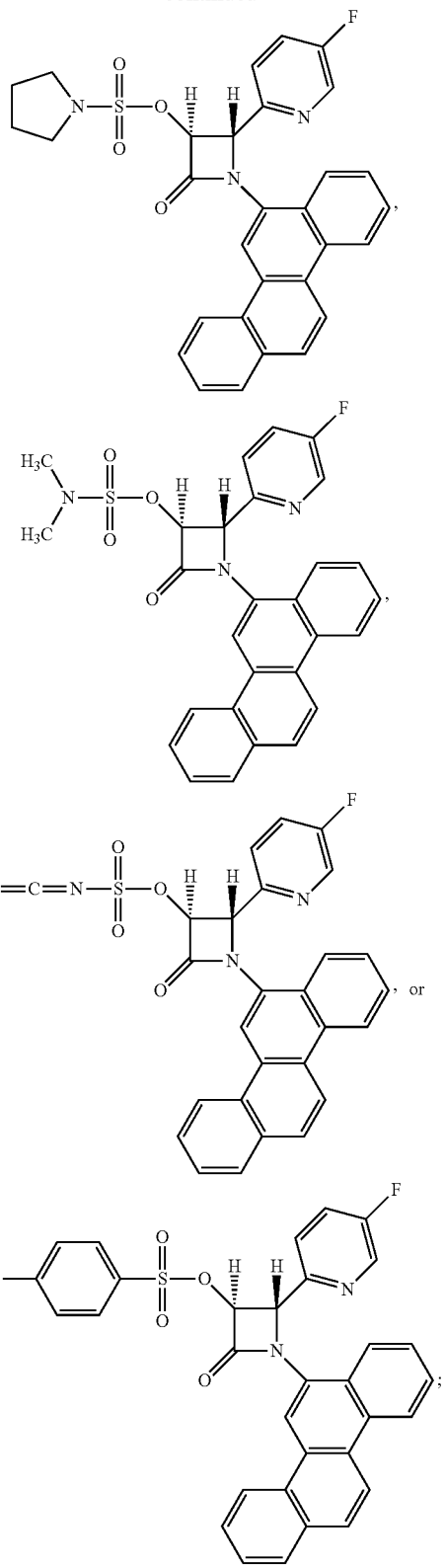
or a pharmaceutically acceptable salt or tautomer thereof.
In another aspect, the present disclosure provides pharmaceutical compositions comprising a compound of the present disclosure and an excipient.

In still another aspect, the present disclosure provides methods of treating or preventing a disease or disorder in a patient in need thereof comprising administering to the patient a therapeutically effective amount of a compound or composition of the present disclosure. In some embodiments, the disease or disorder is cancer. In further embodiments, the cancer is resistant to one or more anti-cancer drugs. In still further embodiments, the cancer is pancreatic cancer. In still further embodiments, the pancreatic cancer is resistant to treatment with gemcitabine. In still further embodiments, the cancer is a KRAS-dependent tumor.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

Histones are elementary nuclear proteins that consist the structure of nucleosome, a basic unit of DNA. Two molecules of each of the four core histones (H2A, H2B, H3, and H4) form an octamer and each histone octamer is wrapped with approximately 146 DNA base pairs in 1.67 left-handed superhelical turns around a histone octamer. Phospho-H2AX or γ-H2AX is an authentic marker of DNA damage through double-stranded breaks that can be stained for. Positive staining is an indication of genomic instability due to telomere dysfunction in cancer cells (telomere is a specific nucleoprotein complex that wraps the terminals of eukaryotic chromosome). Telomere dysfunction triggers the canonical DNA damage response pathway that engages p53 to initiate apoptosis. The positive staining (with red fluorophore/Alexa Fluor® 594) is visible by phospho-H2AX foci—bright red dots in the nucleus of the compound D [DB-3 (OCS)] treated PANC-1 cell lines. Taken together, the bright red dots (FIG. 6, right) are indicative of telomere dysfunction and subsequent DNA damage, followed by apoptosis and eventually death of compound D [DB-3 (OCS)] treated PANC-1 cells in comparison to the control (left).

Figure 7:
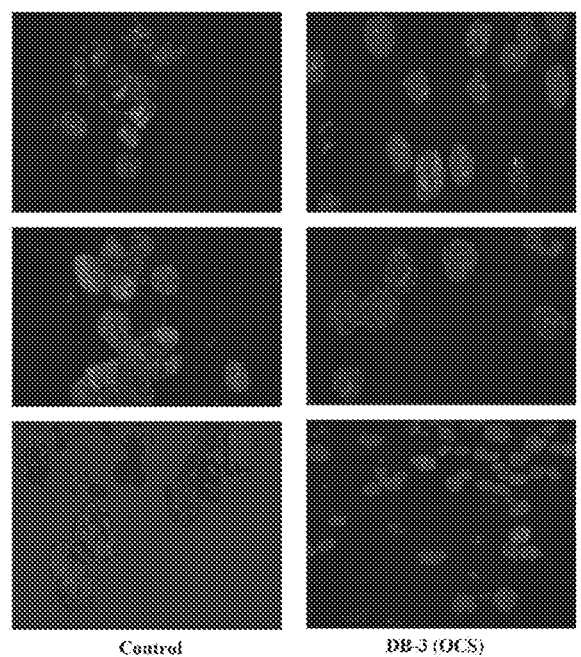

FIG. 7 shows BrdU incorporation of compound D [DB-3 (OCS)]. BrdU (5-bromo-2'-deoxyuridine) incorporation to proceed with immunostaining coverslip slides with Prolong® Gold Antifade reagent were visualized under microscope. Alexa Fluor® 488 (green) was used for BrdU staining along with nuclear marker DAPI (blue). BrdU images were co-localized with nuclear marker DAPI blue.

5'-bromo-2'-deoxyuridine (BrdU) is an analog of the DNA nucleoside thymidine. Thymidine and BrdU have the identical structure except in place of a methyl ($CH_3$) in thymidine there is a bromine (Br) at C-5 in BrdU. BrdU incorporation is a highly explored assay to determine cell proliferation rates in a wide variety of species from plants to mammals. Because of structural identity, BrdU is incorporated (instead of thymidine) in the replicating cells, during the S-phase of the cell cycle (when DNA is replicated) into newly synthesized DNA. Incorporation of BrdU was detected with anti-BrdU antibodies (BrdU Mouse mAb) and subsequent incubation with fluorochrome-conjugated secondary antibody. BrdU specific antibodies were detected by staining with Alexa Fluor® 488 (green) along with nuclear marker DAPI (blue) to identify cells that were actively replicating their DNA. For successful staining, a DNA denaturing step is included to allow the antibody access to the incorporated BrdU. DAPI (4',6-diamidino-2-phenylindole) was used as a secondary stain to provide contrast that helped the primary stain (Alexa Fluor® 488) be prominent. The FIG. 7 clearly shows the rate of DNA replication and subsequent cell proliferation were significantly low in compound D [DB-3 (OCS)] treated PANC-1 cells (right, only a few blue dots) in comparison to the control (left).

DESCRIPTION OF ILLUSTRATIVE EMBODIMENTS

The present disclosure provides novel substituted pyridinyl azetidinone derivatives compounds with potent anticancer properties. Methods for their use for the treatment of disease, such as cancer, including drug-resistant cancers, are also provided. Methods for the manufacture of these compounds are also disclosed herein.

I. COMPOUNDS AND SYNTHETIC METHODS

The compounds of the present disclosure are shown, for example, above, in the summary of the invention section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

The compounds of the present disclosure may be useful for the prevention and treatment of one or more diseases or disorders discussed herein or otherwise. In some embodiments, the compounds disclosed herein are "active compounds" and/or "therapeutic compounds" that may be used as active pharmaceutical ingredients (APIs). In other embodiments, one or more of the disclosed compounds disclosed herein may be characterized or exemplified as an intermediate, a metabolite, and/or prodrug. In some embodiments, one or more of such compounds may also be used for the prevention and treatment of one or more diseases or disorders. Actual suitability for human or veterinary use is typically determined using a combination of clinical trial protocols and regulatory procedures, such as those administered by the Food and Drug Administration (FDA).

In some embodiments, the compounds disclosed herein have the advantage that they may be more efficacious than, be less toxic than, be longer acting than, be more hydrophilic than, be more metabolically stable than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds disclosed herein may contain one or more asymmetrically-substituted carbon or nitrogen atom, and such compounds may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds disclosed herein can have the S or the R configuration. In some embodiments, the present compounds may contain two or more atoms which have a defined stereochemical orientation.

In one aspect, the compounds of the present disclosure contain at least one stereogenic centers at carbon atoms 3 and 4. In some embodiments, carbon atom 3 is in the S configuration. In other embodiments, carbon atom 3 is in the R configuration. In some embodiments, the compounds of the present disclosure contain a stereogenic center at carbon atom 4. In some of these embodiments carbon atom 4 is in the S configuration. In other embodiments, carbon atom 4 is in the R configuration.

Chemical formulas used to represent compounds disclosed herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds disclosed herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds disclosed herein may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds disclosed herein as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

II. TREATMENT OF CANCER AND OTHER DISORDERS

In one aspect, compounds of the present disclosure may be used to induce apoptosis in tumor cells, to induce cell differentiation, to inhibit cancer cell proliferation, and/or to function in a chemopreventative capacity. For example, the β-lactam D was tested using human cancer cell lines. See Example 3 below and FIGS. 1-4. The β-lactams disclosed herein may also be used to reduce cancer cell proliferation and regresses tumor growth in vivo.

In another aspect, the compounds, compositions, and methods disclosed herein may be used to treat cancer or other hyperproliferative diseases. While hyperproliferative diseases can be associated with any disease which causes a cell to begin to reproduce uncontrollably, the prototypical example is cancer. One of the elements of cancer is that the cell's normal apoptotic cycle is interrupted. As such, agents that interrupt the growth of the cells are important as therapeutic agents for treating these diseases. In this disclosure, the compounds of the present disclosure thereof may be used to lead to decreased cell counts and may be used to treat a variety of types of cancer lines. In some embodiments, the compounds are efficacious against cancers which contain a mutation or deletion of the one or more genes, such as the gene which encodes for KRAS.

In some embodiments, cancer cells that may be treated with the compounds or compositions of the present disclosure include, but are not limited to, bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, and uterus cells.

In some embodiments, tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

In some embodiments, cancer cells may be treated by the compounds, methods, and compositions disclosed herein. Cancer cells that may be treated include but are not limited to cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the cancer may be of the following histological types: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

In certain embodiments regarding methods of treating cancer in a patient, comprising administering to the patient a pharmaceutically effective amount of a compound of the present disclosure, the pharmaceutically effective amount is 0.1-1000 mg/kg. In certain embodiments, the pharmaceutically effective amount is administered in a single dose per day. In certain embodiments, the pharmaceutically effective amount is administered in two or more doses per day. The compound may be administered by contacting a tumor cell during ex vivo purging, for example. The method of treatment may comprise any one or more of the following: a) inducing cytotoxicity in a tumor cell; b) killing a tumor cell; c) inducing apoptosis in a tumor cell; d) inducing differentiation in a tumor cell; or e) inhibiting growth in a tumor cell. The tumor cell may be any type of tumor cell, such as a brain cell. Other types of cells include, for example, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

In some embodiments, treatment methods further comprise monitoring treatment progress. In some of these embodiments, the method includes the step of determining a level of changes in hematological parameters and/or cancer stem cell (CSC) analysis with cell surface proteins as diagnostic markers or diagnostic measurement (e.g., screen, assay) in a patient suffering from or susceptible to a disorder or symptoms thereof associated with cancer in which the patient has been administered a therapeutic amount of a compound or composition as described herein. The level of the marker determined in the method can be compared to known levels of marker in either healthy normal controls or in other afflicted patients to establish the patient's disease status. In some embodiments, a second level of the marker in the patient is determined at a time point later than the determination of the first level, and the two levels are compared to monitor the course of disease or the efficacy of the therapy. In some embodiments, a pre-treatment level of marker in the patient is determined prior to beginning treatment according to the methods described herein; this pre-treatment level of marker can then be compared to the level of marker in the patient after the treatment commences, to determine the efficacy of the treatment.

In some embodiments, the patient is a mammal, e.g., a primate, preferably a higher primate, e.g., a human (e.g., a patient having, or at risk of having, a disorder described herein). In some embodiments, the patient is in need of enhancing the patient's immune response. In certain embodiments, the patient is, or is at risk of being, immunocompromised. For example, in some embodiments, the patient is undergoing or has undergone a chemotherapeutic treatment and/or radiation therapy. Alternatively, or in combination, the patient is, or is at risk of being, immunocompromised as a result of an infection.

In some embodiments, the present disclosure provides methods for treating cancers associated with KRAS mutations. In some of these embodiments, the cancer cells may have acquired resistance to gemcitabine and/or broad-spectrum drug resistance.

A. Pancreatic Cancer

Pancreatic cancer is the third leading cause of cancer-related death for both men and women in the United States and is the only major cancer with a 5-year relative survival rate in the single digits, at just 7.7%. While overall cancer incidence and death rates are declining, the incidence and death rates for pancreatic cancer are increasing dangerously. According to the Texas Department of State Health Services, in Texas 3,080 new pancreatic cancer patients were diagnosed and 2664 pancreatic cancer patients died in the first eight months (January-August) of 2016. It is a matter of serious concern that pancreatic cancer is projected to move past colorectal cancer to become the second leading cause of cancer-related death in the United States around 2020. The justifications behind this estimation are: (i) in comparison to other cancers, pancreatic cancer can progress very quickly from stage I (localized within the pancreas) to stage IV (metastatic disease) in an average of 1.3 years; (ii) currently, there are no proven biomarkers, or clues detectable in the blood or other bodily fluids that could indicate the presence of a pancreatic tumor; (iii) only fewer than 20% of pancreatic cancer cases are diagnosed that meet the criteria for surgical intervention (often the Whipple procedure) although the disease recurs in approximately 80% of these surgical patients; (iv) for non-surgical patients (not suitable for surgery), chemotherapy (sometimes along with radiation) is typically offered but is not considered curative at all; (v) around 95% of pancreatic tumors are driven by mutations in KRAS (K-ras or Ki-ras) gene, which signifies a very aggressive and treatment-resistant tumor (Mazur et al., 2014 and Garcia et al., 2014). Mutated KRAS has been dubbed "undruggable," and it is prevalent in five drug-resistant pancreatic cancers that include HS 766T, CaPan-2, HPAC, HPAF-II and PANC-1. Currently there is NO effective treatment (surgery, chemotherapy, radiotherapy, immunotherapy; either individual or in combination) for these five drug-resistant pancreatic cancers; (vi) since 1974, only four drugs have been approved by the U.S. Food & Drug Administration (FDA) to treat pancreatic cancer. These are (a) gemcitabine (Gemzar®) in 1996, (b) erlotinib (Tarceva®) in 2005, (c) albumin-bound paclitaxel (Abraxane®) in 2013, and (d) irinotecan liposome injection (Onivyde™) in 2015. Unfortunately, none of these four drugs is effective against the aforementioned drug-resistant pancreatic adenocarcinoma. For example, the widely used anti-pancreatic cancer drug gemcitabine has an average $IC_{50}$ value against drug-resistant pancreatic cancer cell lines that range from 16 µM to >50 µM. Accordingly, identifying and developing therapies that may be used to treat this disease would be highly desirable.

The compounds of the present disclosure may be used to treat pancreatic cancer. For example, the about 0.002554 µM $IC_{50}$ demonstrated by compound B against PANC-1 is significantly lower than that observed for TX-262 (see Table A below). Stated otherwise, compound B demonstrated approximately 168 times better anticancer activity in preliminary in vitro biological evaluation (triplicate) against a drug-resistant cancer cell line. PANC-1 is referred to generically as the "gold standard of pancreatic cancers" representing as it does almost total resistance to GEM (gemcitabine), the first line treatment currently used in clinical situations. In some embodiments, the compounds of the present disclosure were also shown to be effective against other Gemcitabine-resistant cell lines, such as HPAF-II and HS 766T. See Example 3.

TABLE A

Comparison of IC$_{50}$ values against PANC-1 between TX-262, compound B, and Gemcitabine.

| Compound | PANC-1 cell lines IC$_{50}$ (μM) |
|---|---|
| 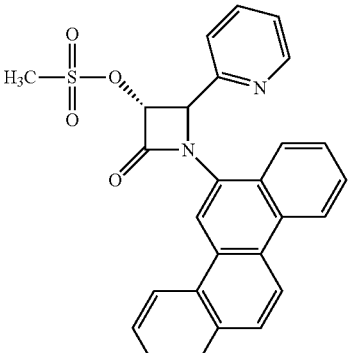 TX-262 | 0.43 |
| 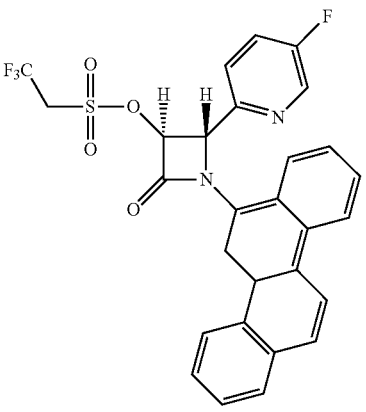 [SMILES: O=C1[C@@H](OS(=O)(=O)CC(F)(F)F)[C@H](c2ccc(F)cn2)N1C1=c2ccccc2=C2C=Cc3ccccc3C2C1] B | 0.002554 |
| Gemcitabine | 37.93 |

In some embodiments, the compounds disclosed herein are also more soluble than TX-262.

In some embodiments, the compounds disclosed herein exhibit higher target specificity than TX-262, including for KRAS, which has been considered to be "undruggable."

III. PHARMACEUTICAL FORMULATIONS AND ROUTES OF ADMINISTRATION

For the purpose of administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound disclosed herein formulated with one or more excipients and/or drug carriers appropriate to the indicated route of administration. In some embodiments, the compounds disclosed herein are formulated in a manner amenable for the treatment of human and/or veterinary patients. In some embodiments, formulation comprises admixing or combining one or more of the compounds disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. Pharmaceutical formulations may be subjected to conventional pharmaceutical operations, such as sterilization and/or may contain drug carriers and/or excipients such as preservatives, stabilizers, wetting agents, emulsifiers, encapsulating agents such as lipids, dendrimers, polymers, proteins such as albumin, or nucleic acids, and buffers, etc.

Pharmaceutical formulations may be administered by a variety of methods, e.g., orally or by injection (e.g. subcutaneous, intravenous, intraperitoneal, etc.). Depending on the route of administration, the compounds disclosed herein may be coated in a material to protect the compound from the action of acids and other natural conditions which may inactivate the compound. To administer the active compound by other than parenteral administration, it may be necessary to coat the compound with, or co-administer the compound with, a material to prevent its inactivation. For example, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds disclosed herein may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds disclosed herein can be administered orally, for example, with an inert diluent or an assimilable edible carrier. The compounds and other ingredients may also be enclosed in a hard or soft shell gelatin capsule, compressed into tablets, or incorporated directly into the patient's diet. For oral therapeutic administration, the compounds disclosed herein may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the therapeutic compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical carrier. In some embodiments, the specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In general a human equivalent dose (HED) in mg/kg can be calculated in accordance with the following formula (see, e.g., Reagan-Shaw et al., *FASEB J.*, 22(3): 659-661, 2008, which is incorporated herein by reference):

HED(mg/kg)=Animal dose(mg/kg)×(Animal $K_m$/Human $K_m$)

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25.

$K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some particular embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, patients may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the patient has eaten or will eat.

IV. COMBINATION THERAPY

In addition to being used as a monotherapy, the compounds disclosed herein may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples include administering to the patient a pharmaceutically effective amount of a compound of the present disclosure, and may further comprise a treatment selected from the group consisting of administering a pharmaceutically effective amount of a second drug, radiotherapy, gene therapy, and surgery. Such methods may further comprise (1) contacting a tumor cell with the compound prior to contacting the tumor cell with the second drug, (2) contacting a tumor cell with the second drug prior to contacting the tumor cell with the compound, or (3) contacting a tumor cell with the compound and the second drug at the same time. The second drug may, in certain embodiments, be an antibiotic, anti-inflammatory, anti-neoplastic, anti-proliferative, anti-viral, immunomodulatory, or immunosuppressive. The second drug may be an alkylating agent, androgen receptor modulator, cytoskeletal disruptor, estrogen receptor modulator, histone-deacetylase inhibitor, HMG-CoA reductase inhibitor, prenyl-protein transferase inhibitor, retinoid receptor modulator, topoisomerase inhibitor, or tyrosine kinase inhibitor. In certain embodiments, the second drug is 5-azacitidine, 5-fluorouracil, 9-cis-retinoic acid, actinomycin D, alitretinoin, all-trans-retinoic acid, annamycin, axitinib, belinostat, bevacizumab, bexarotene, bosutinib, busulfan, capecitabine, carboplatin, carmustine, CD437, cediranib, cetuximab, chlorambucil, cisplatin, cyclophosphamide, cytarabine, dacarbazine, dasatinib, daunorubicin, decitabine, docetaxel, dolastatin-10, doxifluridine, doxorubicin, doxorubicin, epirubicin, erlotinib, etoposide, etoposide, gefitinib, gemcitabine, gemtuzumab ozogamicin, hexamethylmelamine, idarubicin, ifosfamide, imatinib, irinotecan, isotretinoin, ixabepilone, lapatinib, LBH589, lomustine, mechlorethamine, melphalan, mercaptopurine, methotrexate, mitomycin, mitoxantrone, MS-275, neratinib, nilotinib, nitrosourea, oxaliplatin, paclitaxel, plicamycin, procarbazine, semaxanib, semustine, sodium butyrate, sodium phenylacetate, streptozotocin, suberoylanilide hydroxamic acid, sunitinib, tamoxifen, teniposide, thiopeta, tioguanine, topotecan, TRAIL, trastuzumab, tretinoin, trichostatin A, valproic acid, valrubicin, vandetanib, vinblastine, vincristine, vindesine, or vinorelbine.

In some embodiments for the treatment or prevention of cancer, compounds of the invention may be combined with one or more of the following: radiation, chemotherapy agents (e.g., cytotoxic agents such as anthracyclines, vincristine, vinblastin, microtubule-targeting agents such as paclitaxel and docetaxel, 5-FU and related agents, cisplatin and other platinum-containing compounds, irinotecan and topotecan, gemcitabine, temozolomide, etc.), targeted therapies (e.g., imatinib, bortezomib, bevacizumab, rituximab), or vaccine therapies designed to promote an enhanced immune response targeting cancer cells.

Various combinations may be employed, such as when a compound of the present disclosure is "A" and "B" represents a secondary agent, non-limiting examples of which are described below:

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

Administration of the compounds of the present disclosure to a patient will follow general protocols for the administration of pharmaceuticals, taking into account the toxicity, if any, of the drug. It is expected that the treatment cycles would be repeated as necessary.

V. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanyl" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "===" represents a single bond or a double bond. Thus, the formula

covers, for example,

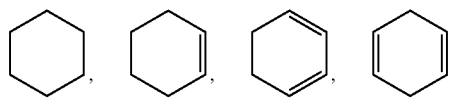

and

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⁓", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⦀⦀⦀" means a single bond where the group attached to the thick end of the wedge is "into the page". The symbol "⁓" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

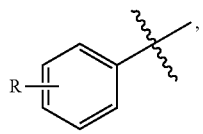

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

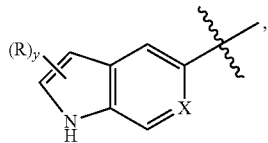

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C (CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present.

If more than one ring is present, the rings may be fused or unfused. Unfused rings are connected with a covalent bond. Non-limiting examples of arenediyl groups include:

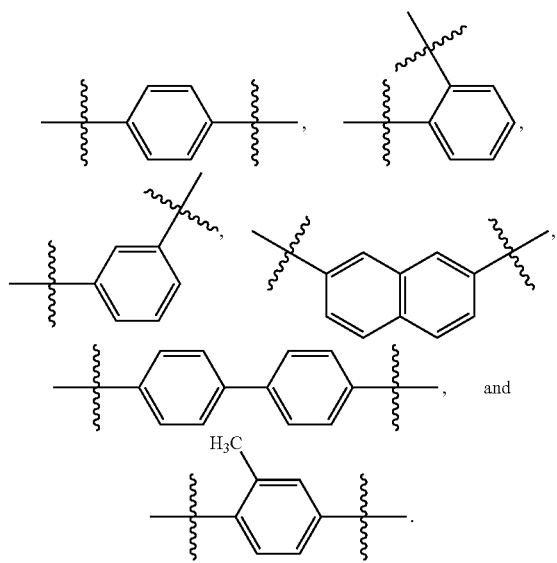

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to a divalent aromatic group, with two aromatic carbon atoms, two aromatic nitrogen atoms, or one aromatic carbon atom and one aromatic nitrogen atom as the two points of attachment, said atoms forming part of one or more aromatic ring structures, each with three to eight ring atoms, wherein at least one of the ring atoms of the aromatic ring structure(s) is nitrogen, oxygen or sulfur, and wherein the divalent group consists of no atoms other than carbon, hydrogen, aromatic nitrogen, aromatic oxygen and aromatic sulfur. If more than one ring is present, the rings are be fused; however, the term heteroarenediyl does not preclude the presence of one or more alkyl or aryl groups (carbon number limitation permitting) attached to one or more ring atoms. Non-limiting examples of heteroarenediyl groups include:

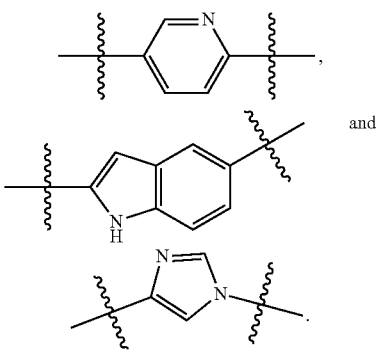

A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH₃, —C(O)N(CH₃)₂, —OC(O)CH₃, —NHC(O)CH₃, —S(O)₂OH, or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The term "heterocycloalkanediyl" when used without the "substituted" modifier refers to a divalent cyclic group, with two carbon atoms, two nitrogen atoms, or one carbon atom and one nitrogen atom as the two points of attachment, said atoms forming part of one or more ring structure(s) wherein at least one of the ring atoms of the non-aromatic ring structure(s) is nitrogen, oxygen or sulfur, and wherein the divalent group consists of no atoms other than carbon, hydrogen, nitrogen, oxygen and sulfur.

If more than one ring is present, the rings are fused. As used herein, the term heterocycloalkanediyl does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkanediyl groups include:

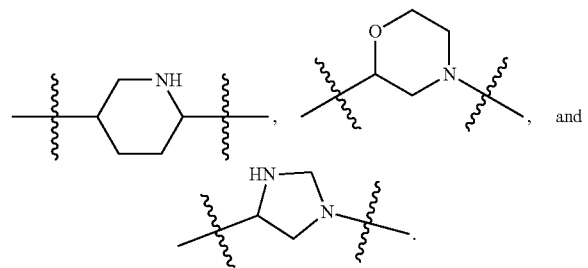

The term "acyl" when used without the "substituted" modifier refers to the group —C(O)R, in which R is a hydrogen, alkyl, cycloalkyl, or aryl as those terms are defined above. The groups, —CHO, —C(O)CH₃ (acetyl, Ac), —C(O)CH₂CH₃, —C(O)CH(CH₃)₂, —C(O)CH(CH₂)₂, —C(O)C₆H₅, and —C(O)C₆H₄CH₃ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The groups, —C(O)CH₂CF₃, —CO₂H (carboxyl), —CO₂CH₃ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples include: —OCH₃ (methoxy), —OCH₂CH₃ (ethoxy), —OCH₂CH₂CH₃, —OCH(CH₃)₂ (isopropoxy), or —OC(CH₃)₃ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier, one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "alkylamino" when used without the "substituted" modifier refers to the group —NHR, in which R is an alkyl, as that term is defined above. Non-limiting examples include: —NHCH₃ and —NHCH₂CH₃. The term "dialkylamino" when used without the "substituted" modifier refers to the group —NRR', in which R and R' can be the same or different alkyl groups. Non-limiting examples of dialkylamino groups include: —N(CH₃)₂ and —N(CH₃)(CH₂CH₃). The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —NHC₆H₅. The term "amido" (acylamino), when used without the "substituted" modifier, refers to the group —NHR, in which R is acyl, as that term is defined above. A non-limiting example of an amido group is —NHC(O)CH₃. When any of these terms is used with the "substituted" modifier, one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "cycloalkylsulfonyl", "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study patients.

An "active ingredient" (AI) (also referred to as an active compound, active substance, active agent, pharmaceutical agent, agent, biologically active molecule, or a therapeutic compound) is the ingredient in a pharmaceutical drug or a pesticide that is biologically active. The similar terms active pharmaceutical ingredient (API) and bulk active are also used in medicine, and the term active substance may be used for pesticide formulations.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug) is a compound or composition used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients (defined above) in pharmaceutical contexts.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom(s) in a subject or patient that is experiencing or displaying the pathology or symptomatology of the disease.

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringable liquid or other injectable formulations.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Synthesis and Characterization i. General Synthetic Methods

Melting points were determined by a DigiMelt MPA 160 (Stanford research systems, USA) melting point apparatus equipped with a microprocessor controlled built-in digital thermometer. FT-IR spectra were recorded on a Bruker Alpha modular Platinum-ATR FT-IR spectrometer with OPUS software, using the samples directly (neat) without making pallets. $^1$H-NMR (600 MHz), $^{13}$C-NMR (150 MHz), and $^{19}$F-NMR (564 MHz) spectra were obtained at ambient temperature with Bruker superconducting Ultrashield Plus 600 MHz NMR spectrometer with central field 14.09 T, coil inductance 89.1 H, and magnetic energy 1127.2 kJ using $d_6$-DMSO or CDCl$_3$ as solvent. The high-resolution electrospray ionization mass spectra (HR-ESIMS) were carried out by QSTAR XL (ABSCIEX, MA, USA) mass spectrometer by turbo ion spray electrospray ionization (ion spray voltage: +/−5100V). All the solvents were purchased from Fisher-Scientific throughout the investigation. Dichloromethane and triethylamine were dried following the standard procedures. Deionized water was used for the preparation of all aqueous solutions.

ii. Synthesis

Compounds A-L (Scheme 1) were synthesized following Scheme 2. All the reactions and separation steps were monitored by TLC (Thin Layer Chromatography). In all the steps, extraction was performed following standard procedure. Finally, column chromatographic separation was carried out after each step to isolate the respective products in pure form.

Scheme 1. Structure of 4-(5-fluoropyridin-2-yl)-2-azetidinones

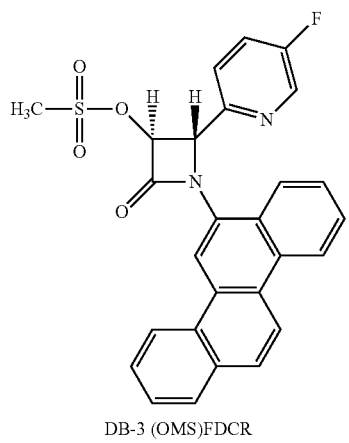

DB-3 (OMS)FDCR (A)

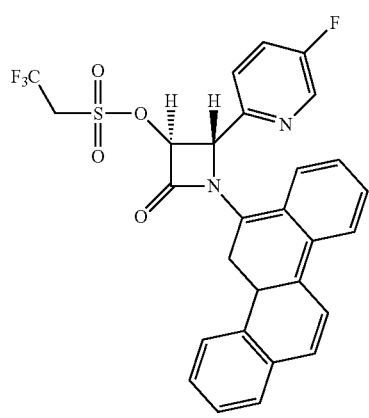

DB-3 (OTFE)LV (B)

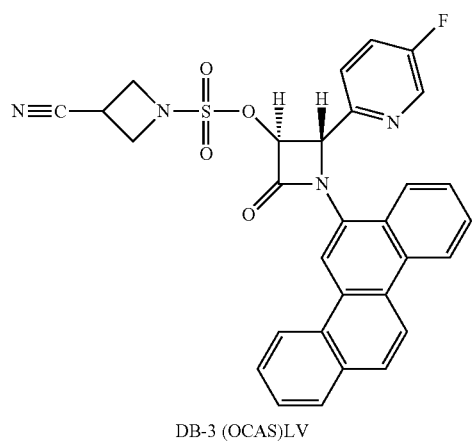

DB-3 (OCAS)LV (C)

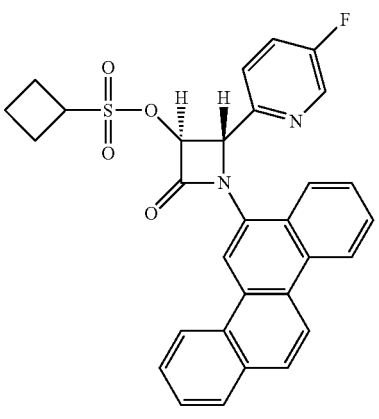

DB-3 (OCS)CRFD (D)

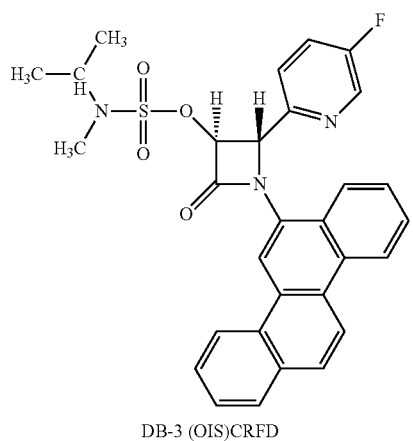
DB-3 (OIS)CRFD
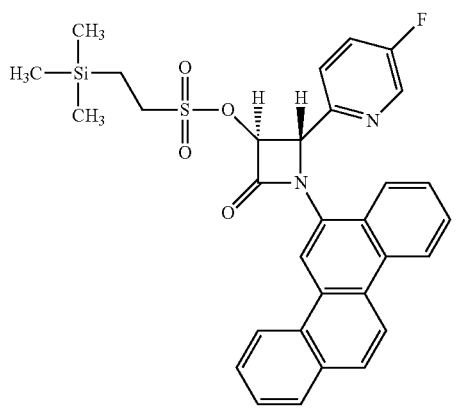
DB-3 (OTMS)FDCR
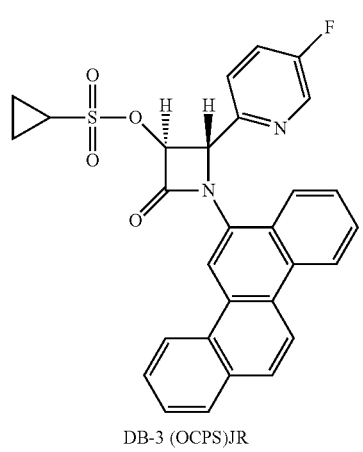
DB-3 (OCPS)JR
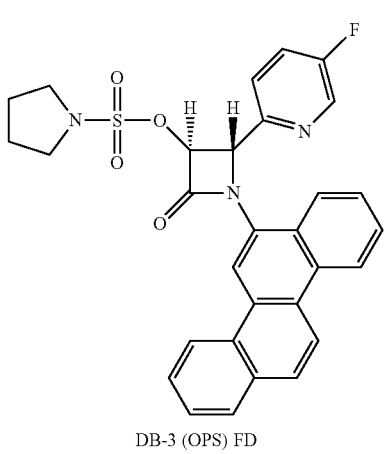
DB-3 (OPS) FD
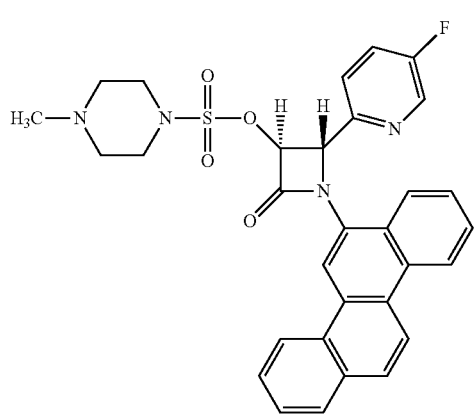
DB-3 (OMP)FDCR
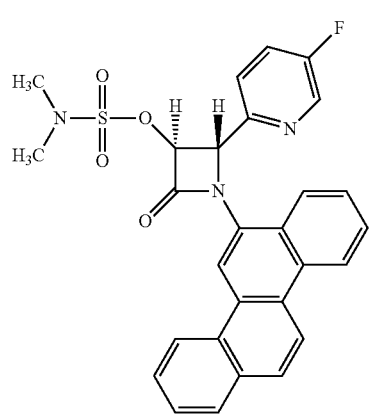
DB-3 (ODS) FDIS (K)

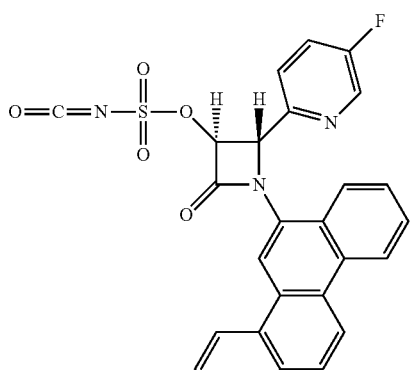

DB-3 (Isocyan)LVFD (L)

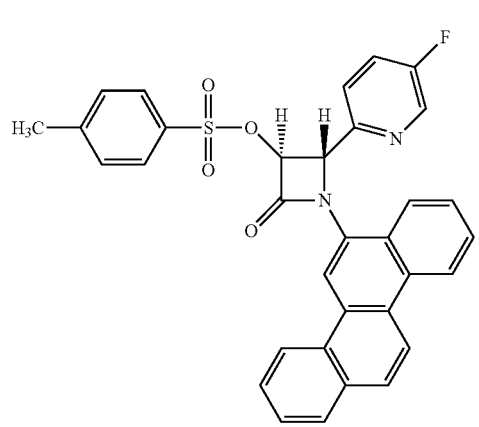

DB-3 (OTS)LV

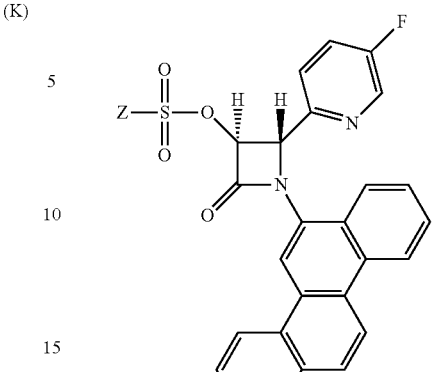

General Structure [A-L]

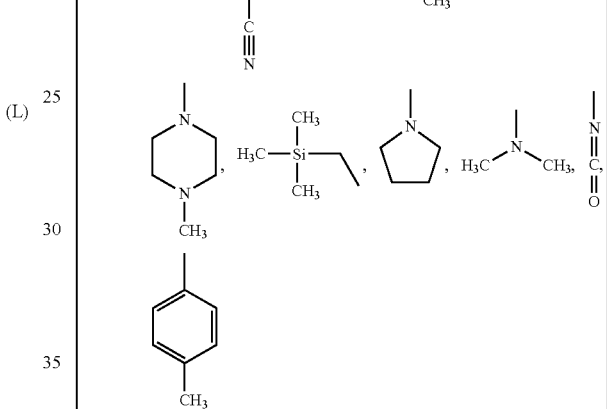

The compounds were synthesized following Scheme 2. All the steps were monitored by TLC (Thin Layer Chromatography). In all the steps, extraction was done following standard procedure. Finally, column chromatographic separation was carried out in every step to isolate the respective products in pure form.

Scheme 2. Synthesis of 4-(5-Fluoropyridin-2-yl)-2-azetidinones

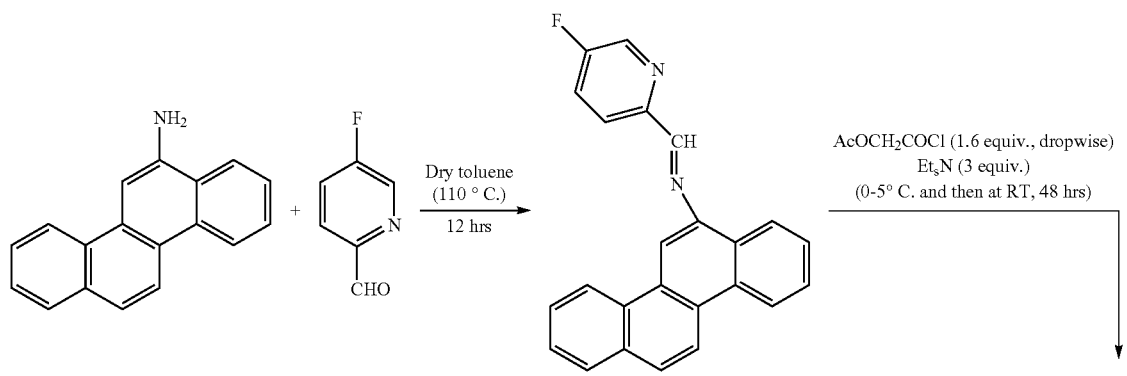

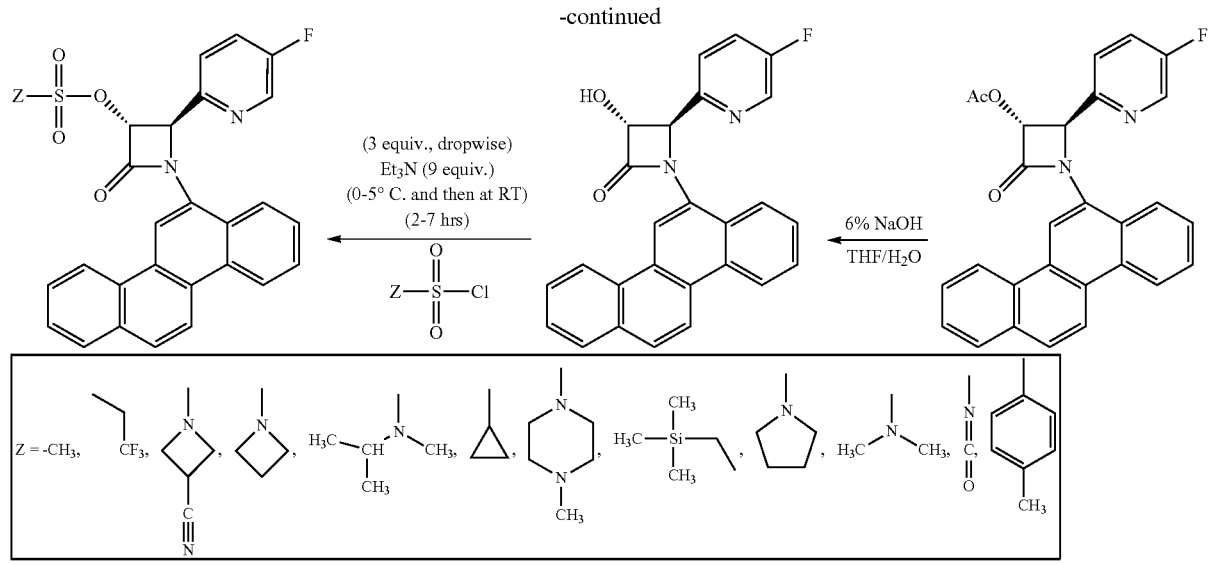

All compounds were characterized by extensive spectral studies. UTRGV in house infrared (IR), 1D- and 2D-NMR (nuclear magnetic resonance) spectroscopy were performed for each compound to find out the exact stereo-(racemic) and regiochemistry of the compounds and finally high resolution mass spectral (HRMS) analysis service was purchased from the State University of New York (SUNY).

iii. Characterization (±)-Trans-N-(chrysen-6-yl)-2-(5-fluoropyridin-2-yl)-4-oxoazetidin-3-yl methanesulfonate (A): Brownish white (96% yield); m.p. 253-254° C.; IR (cm$^{-1}$): v (max) 1766, 1440, 1369, 1144, 1041, 1026, 996, 841, 823, 778, 756, 485; $^1$H-NMR (600 MHz, d$_6$-DMSO): δ 9.00 (m, 3H), 8.95 (s, 1H), 8.85 (d, J=9.12 Hz, 1H), 8.58 (d, J=2.76 Hz, 1H), 8.31 (m, 1H), 8.12 (t, J=9.48 Hz, 1H), 7.81 (m, 4H), 7.71 (m, 2H), 6.43 (d, J=1.56 Hz, 1H), 6.09 (d, J=1.62 Hz, 1H), 3.52 (s, 3H); $^{13}$C-NMR (150 MHz, d$_6$-DMSO): δ 162.52, 160.34, 158.64, 150.60, 138.99, 138.83, 132.34, 131.21, 131.16, 130.16, 129.02, 128.53, 128.26, 127.67, 127.61, 127.43, 126.72, 125.66, 125.10, 124.53, 124.32, 124.13, 121.64, 116.17, 82.15, 63.69, 38.57; $^{19}$F-NMR (564 MHz, d$_6$-DMSO): δ –126.45; HR-ESIMS: m/z 487.1141 [M+H]+ (calcd for C$_{27}$H$_{19}$FN$_2$O$_4$S: 486.1128).

(±)-Trans-N-(chrysen-6-yl)-2-(5-fluoropyridin-2-yl)-4-oxoazetidin-3-yl-2,2,2-trifluoroethane-1-sulfonate (B): Greenish white (91% yield); m.p. 126-127° C.; JR (cm$^{-1}$): v (max) 1766, 1842, 1392, 1180, 1144, 1039, 1025, 989, 844, 817, 787, 758, 586; 1H-NMR (600 MHz, d$_6$-DMSO): δ 9.03 (d, J=8.40 Hz, 1H), 8.99 (d, J=1.14 Hz, 1H), 8.98 (s, 1H), 8.85 (d, J=9.12 Hz, 1H), 8.60 (d, J=2.88 Hz, 1H), 8.29 (m, 1H), 8.12 (t, J=9.42 Hz, 2H), 7.82 (m, 4H), 7.72 (m, 2H), 6.49 (d, J=1.62 Hz, 1H), 6.26 (d, J=1.74 Hz, 1H), 5.36 (m, 2H); $^{13}$C-NMR (150 MHz, d$_6$-DMSO): δ 160.59, 160.38, 158.69, 150.23, 139.10, 138.94, 132.34, 131.19, 131.01, 130.17, 129.02, 128.60, 128.27, 127.69, 127.65, 127.44, 126.62, 125.99, 125.05, 124.50, 124.38, 124.33, 124.16, 121.64, 116.30, 83.07, 63.52, 52.02; $^{19}$F-NMR (564 MHz, d$_6$-DMSO): δ –48.90, –126.25; HR-ESIMS: m/z 555.0978 [M–H]+(calcd for C$_{28}$H$_{20}$F$_4$N$_2$O$_4$S: 556.1080).

(±)-Trans-N-(chrysen-6-yl)-2-(5-fluoropyridin-2-yl)-4-oxoazetidin-3-yl 3-cyanoazetidine-1-sulfonate (C): Brownish white (89% yield); m.p. 212-213° C.; IR (cm$^{-1}$): v (max) 1754, 1483, 1373, 1153, 1079, 1027, 991, 843, 820, 788, 754, 547; $^1$H-NMR (600 MHz, CDCl3): δ 8.76 (m, 1H), 8.59 (m, 2H), 8.54 (s, 1H), 8.49 (d, J=2.70 Hz, 1H), 8.26 (m, 1H), 7.97 (distorted t, J=9.36 Hz, 2H), 7.73 (m, 3H), 7.44 (t, J=7.44 Hz, 1H), 7.31 (dd, J=4.20, 8.38 Hz, 1H), 7.31 (td, J=2.64, 8.10 Hz, 1H), 6.00 (d, J=1.02 Hz, 1H), 5.70 (d, J=1.02 Hz, 1H), 4.57 (t, J=8.82 Hz, 1H), 4.44 (m, 3H), 3.65 (m, 1H); $^{13}$C-NMR (150 MHz, CDCl$_3$): δ 162.02, 160.35, 158.63, 148.92, 148.89, 139.43, 139.26, 132.20, 131.46, 130.05, 129.83, 128.72, 128.39, 128.19, 127.61, 127.33, 127.20, 127.15, 126.93, 124.59, 124.56, 123.81, 123.70, 123.65, 123.52, 83.84, 65.57, 54.98, 54.79, 17.59; $^{19}$F-NMR (564 MHz, CDCl$_3$): δ –124.75; HR-ESIMS: m/z 553.1323 [M+H]+(calcd for C$_{30}$H$_{21}$FN$_4$O$_4$S: 552.1268).

(±)-Trans-N-(chrysen-6-yl)-2-(5-fluoropyridin-2-yl)-4-oxoazetidin-3-yl cyclobutanesulfonate (D): White (83% yield); m.p. 122-123° C.; IR (cm$^{-1}$): v (max) 1758, 1482, 1440, 1397, 1117, 1071, 1026, 991, 838, 819, 753, 427; 1H-NMR (600 MHz, CDCl$_3$): δ 8.68 (m, 1H), 8.51 (m, 2H), 8.46 (s, 1H), 8.40 (d, J=2.76 Hz, 1H), 8.20 (m, 1H), 7.89 (m, 2H), 7.65 (m, 3H), 7.56 (t, J=7.20 Hz, 1H), 7.31 (dd, J=4.20, 8.58 Hz, 1H), 7.16 (td, J=2.70, 6.75 Hz, 1H), 5.86 (d, J=1.68 Hz, 1H), 5.60 (d, J=1.62 Hz, 1H), 4.22 (quintet, J=8.28 Hz, 1H), 2.45 (m, 2H), 2.60 (m, 2H), 2.04 (m, 2H), 13C-NMR (150 MHz, CDCl$_3$): δ; 161.99, 139.31, 139.15, 132.19, 130.08, 130.06, 128.68, 128.25, 128.10, 127.52, 127.37, 127.28, 127.09, 127.07, 126.87, 124.56, 124.53, 123.94, 123.63, 123.54, 123.42, 122.88, 120.79, 117.63, 82.64, 65.70, 54.03, 24.40, 24.17, 17.34; $^{19}$F-NMR (564 MHz, CDCl$_3$): δ –125.15; HR-ESIMS: m/z 527.1456 [M+H]+ (calcd for C$_{30}$H$_{23}$FN$_2$O$_4$S: 526.1363).

(±)-Trans-N-(chrysen-6-yl)-2-(5-fluoropyridin-2-yl)-4-oxoazetidin-3-yl isopropyl(methyl)sulfamate (E): Dark Green (90% yield); m.p. 166-167° C.; IR (cm$^{-1}$): v (max) 2953, 2920, 2851, 1770, 1484, 1460, 1376, 1227, 1171, 1149, 1012, 959 755, 531; $^1$H-NMR (600 MHz, CDCl$_3$): δ 8.65 (m, 1H), 8.50 (m, 2H), 8.47 (s, 1H), 8.38 (d, J=2.70 Hz, 1H), 7.86 (m, 2H), 7.63 (m, 3H), 7.54 (t, J=7.44 Hz, 1H), 7.28 (m, 1H), 7.17 (s, 1H), 7.14 (td, J=2.76, 8.31 Hz, 1H), 5.73 (d, J=1.38 Hz, 1H), 5.63 (d, J=1.26 Hz, 1H), 4.17 (m, 1H), 2.83 (s, 3H), 1.19 (m, 6H); $^{13}$C-NMR (150 MHz, CDCl$_3$): δ 162.09, 160.22, 158.51, 149.64, 139.08, 138.91, 132.17, 131.42, 130.28, 130.09, 128.65, 128.15, 128.00, 127.46, 127.34, 127.04, 126.83, 124.67, 124.05, 123.58, 123.44, 122.94, 120.79, 117.60, 82.98, 65.70, 50.93, 28.74, 19.85, 19.79; $^{19}$F-NMR (564 MHz, CDCl$_3$): δ −125.49; HR-ESIMS: m/z 544.1718 [M+H]+(calcd for C$_{30}$H$_{26}$FN$_3$O$_4$S: 543.1628).

(±)-Trans-N-(chrysen-6-yl)-2-(5-fluoropyridin-2-yl)-4-oxoazetidin-3-yl cyclopropanesulfonate (F): Light grey (81% yield); m.p. 180-181° C.; IR (cm$^{-1}$): ν (max) 1750, 1481, 1369, 1351, 1166, 1076, 884, 838, 818, 754, 526; $^1$H-NMR (600 MHz, CDCl$_3$): δ 8.75 (m, 1H), 8.58 (m, 2H), 8.54 (s, 1H), 8.48 (d, J=2.76 Hz, 1H), 8.29 (m, 1H), 7.97 (t, J=8.70 Hz, 2H), 7.73 (m, 3H), 7.64 (t, J=7.14 Hz, 1H), 7.32 (m, 1H), 7.22 (td, J=2.82, 8.19 Hz, 1H), 5.99 (d, J=1.50 Hz, 1H), 5.70 (d, J=1.56 Hz, 1H), 2.86 (m, 1H), 1.38 (m, 2H), 1.25 (m, 1H), 1.21 (m, 1H); $^{13}$C-NMR (150 MHz, CDCl$_3$): δ; 161.91, 158.57, 149.26, 149.23, 139.29, 139.13, 132.18, 131.44, 130.08, 128.68, 128.27, 128.12, 127.53, 127.38, 127.34, 127.09, 126.87, 124.64, 123.93, 123.63, 123.56, 122.88, 120.79, 117.77, 82.93, 65.63, 28.78, 6.88, 6.20; $^{19}$F-NMR (564 MHz, CDCl$_3$): δ −125.13; HR-ESIMS: m/z 513.1261 [M+H]+(calcd for C$_{29}$H$_{21}$FN$_2$O$_4$S: 512.1206).

(±)-Trans-N-(chrysen-6-yl)-2-(5-fluoropyridin-2-yl)-4-oxoazetidin-3-yl 4-methylpiperazine-1-sulfonate (G): White (94% yield); m.p. 146-147° C.; IR (cm$^{-1}$): ν (max) 1761, 1483, 1382, 1225, 1176, 1153, 1026, 950, 887, 755, 626, 555; $^1$H-NMR (600 MHz, d$_6$-DMSO): δ 9.03 (m, 1H), 8.98 (m, 2H), 8.87 (s, 1H), 8.84 (d, J=9.18 Hz, 1H), 8.59 (d, J=2.64 Hz, 1H), 8.30 (d, J=7.74 Hz, 1H), 8.10 (m, 2H), 7.78 (m, 5H), 6.41 (d, J=0.90 Hz, 1H), 6.00 (d, J=1.32 Hz, 1H), 3.34 (m, 8H), 2.76 (s, 3H); $^{13}$C-NMR (150 MHz, d$_6$-DMSO): δ; 161.61, 160.38, 158.68, 150.47, 139.06, 138.89, 129.02, 128.86, 128.55, 128.01, 127.68, 127.62, 127.45, 127.15, 125.69, 125.66, 125.08, 124.50, 124.37, 124.16, 124.07, 121.64, 116.25, 115.71, 82.59, 65.38, 63.71, 52.90, 46.00; $^{19}$F-NMR (564 MHz, d$_6$-DMSO): δ −126.20; HR-ESIMS: m/z 571.1833 [M+H]+(calcd for C$_{31}$H$_{27}$FN$_4$O$_4$S: 570.1737).

(±)-Trans-N-(chrysen-6-yl)-2-(5-fluoropyridin-2-yl)-4-oxoazetidin-3-yl 2-(trimethylsilyl)ethane-1-sulfonate (H): Greyish white (79% yield); m.p. 210-211° C.; IR (cm$^{-1}$): ν (max) 1744, 1483, 1364, 1226, 1180, 1162, 1153, 1080, 891, 837, 810, 794, 749, 538, 508; $^1$H-NMR (600 MHz, CDCl$_3$): δ 8.66 (d, J=2.64 Hz, 1H), 8.50 (m, 2H), 8.45 (s, 1H), 8.38 (d, J=2.76 Hz, 1H), 8.18 (m, 2H), 7.86 (m, 2H), 7.63 (m, 2H), 7.53 (td, J=0.96, 7.83 Hz, 1H), 7.21 (m, 1H), 7.13 (td, J=2.82, 8.01 Hz, 1H), 5.85 (d, J=1.68 Hz, 1H), 5.59 (d, J=1.68 Hz, 1H), 3.30 (m, 2H), 1.44 (s, 9H), 1.14 (m, 2H); $^{13}$C-NMR (150 MHz, CDCl$_3$): δ; 164.10, 160.59, 151.22, 141.33, 141.16, 134.20, 133.47, 132.10, 132.02, 130.70, 130.31, 130.15, 129.55, 129.40, 129.38, 129.12, 129.11, 128.90, 128.56, 126.53, 125.66, 124.90, 122.81, 119.87, 84.76, 67.70, 50.92, 12.36, 2.01; $^{19}$F-NMR (564 MHz, CDCl$_3$): δ −125.15; HR-ESIMS: m/z 573.1697 [M+H]+(calcd for C$_{31}$H$_{29}$FN$_2$O$_4$SSi: 572.1601).

(±)-Trans-N-(chrysen-6-yl)-2-(5-fluoropyridin-2-yl)-4-oxoazetidin-3-yl pyrrolidine-1-sulfonate (I): Bluish white (95% yield); m.p. 205-206° C.; IR (cm$^{-1}$): ν (max) 1749, 1483, 1370, 1227, 1202, 1166, 1066, 1008, 987, 848, 821, 810, 752, 742, 669, 532; $^1$H-NMR (600 MHz, CDCl$_3$): δ 8.75 (m, 1H), 8.59 (m, 2H), 8.56 (s, 1H), 8.46 (d, J=2.76 Hz, 1H), 8.30 (m, 1H), 7.96 (m, 2H), 7.72 (m, 3H), 7.63 (td, J=0.84, 7.44 Hz, 1H), 7.35 (m, 1H), 7.22 (td, J=2.88, 8.37 Hz, 1H), 5.88 (d, J=1.62 Hz, 1H), 5.70 (d, J=1.62 Hz, 1H), 3.36 (m, 4H), 2.03 (m, 4H); $^{13}$C-NMR (150 MHz, CDCl$_3$): δ 162.36, 160.24, 158.52, 149.54, 139.19, 139.03, 132.19, 131.44, 130.23, 130.10, 128.67, 128.18, 128.04, 127.48, 127.36, 127.06, 126.85, 124.62, 124.03, 123.60, 123.39, 122.93, 120.81, 117.63, 83.16, 65.71, 49.17, 25.73; $^{19}$F-NMR (564 MHz, CDCl$_3$): δ −125.45; HR-ESIMS: m/z 542.1574 [M+H]+(calcd for C$_{30}$H$_{24}$FN$_3$O$_4$S: 541.1472).

(±)-Trans-N-(chrysen-6-yl)-2-(5-fluoropyridin-2-yl)-4-oxoazetidin-3-yl dimethylsulfamate (J): Beige (87% yield); m.p. 196-198° C.; IR (cm$^{-1}$): ν (max) 1758, 1481, 1438, 1337, 1305, 1234, 1203, 1170, 1071, 1006, 835, 754, 527; $^1$H-NMR (600 MHz, CDCl$_3$): δ 9.03 (d, J=8.34 Hz, 1H), 8.98 (m, 1H), 8.96 (s, 1H), 8.84 (d, J=9.18 Hz, 1H), 8.84 (d, J=9.18 Hz, 1H), 8.58 (d, J=2.88 Hz, 1H), 8.31 (m, 1H), 8.11 (m, 2H), 7.87 (m, 1H), 7.80 (m, 2H), 7.46 (m, 2H), 6.38 (d, J=1.92 Hz, 1H), 5.95 (d, J=1.92 Hz, 1H), 2.95 (s, 6H); $^{13}$C-NMR (150 MHz, CDCl$_3$): δ 161.83, 160.35, 158.66, 150.60, 139.02, 138.86, 132.34, 131.19, 131.08, 130.17, 129.01, 128.51, 127.68, 127.66, 127.59, 127.43, 126.78, 125.67, 125.64, 125.13, 124.28, 124.17, 121.64, 116.21, 82.35, 63.80, 38.55; $^{19}$F-NMR (564 MHz, CDCl$_3$): δ −125.45; HR-ESIMS: m/z 516.1366 [M+H]+(calcd for C$_{26}$H$_{22}$FN$_3$O$_4$S: 515.1315).

(±)-Trans-N-(chrysen-6-yl)-2-(5-fluoropyridin-2-yl)-4-oxoazetidin-3-yl sulfurisocyanatidate (K): Pale pink (85% yield); m.p. 125-126° C.; IR (cm$^{-1}$): ν (max) 2920, 2851, 1737, 1593, 1514, 1483, 1462, 1377, 1279, 1224, 1185, 1031, 946, 756; $^1$H-NMR (600 MHz, d$_6$-DMSO): δ 9.00 (m, 1H), 8.95 (m, 1H), 8.85 (s, 1H), 8.81 (m, 2H), 8.55 (m, 1H), 8.36 (m, 2H), 7.71 (m, 6H), 6.19 (broad s, 1H), 5.84 (broad s, 1H); $^{13}$C-NMR (150 MHz, d$_6$-DMSO): δ 172.50, 158.50, 155.63, 138.74, 138.58, 132.33, 131.77, 131.22, 130.13, 128.98, 128.25, 128.15, 127.75, 127.63, 127.54, 127.32, 127.27, 126.90, 125.63, 125.41, 124.28, 124.18, 124.12, 121.62, 115.52, 79.45, 63.80; $^{19}$F-NMR (564 MHz, d$_6$-DMSO): δ −127.10; HR-ESIMS: m/z 452.1390 [M+H-CNOF]+(calcd for C$_{26}$H$_{17}$N$_2$O$_4$S: 453.0909).

(±)-Trans-N-(chrysen-6-yl)-2-(5-fluoropyridin-2-yl)-4-oxoazetidin-3-yl 4-methylbenzenesulfonate (L): Transparent white (94% yield); m.p. 220-221° C.; IR (cm$^{-1}$): ν (max) 1771, 1596, 1481, 1391, 1365, 1281, 1225, 1192, 1152, 1094, 1067, 1025, 1006, 986, 886, 859, 754, 635, 582, 493; $^1$H-NMR (600 MHz, d$_6$-DMSO): δ 8.95 (d, J=8.40 Hz, 1H), 8.88 (s, 1H), 8.85 (m, 1H), 8.71 (d, J=6.06 Hz, 1H), 8.46 (m, 1H), 8.19 (m, 1H), 8.02 (d, J=8.70 Hz, 2H), 7.73 (m, 6H), 7.54 (d, J=5.22 Hz, 2H), 7.36 (d, J=8.16 Hz, 2H), 6.14 (d, J=1.68 Hz, 1H), 5.90 (d, J=1.74 Hz, 1H), 2.35 (s, 3H); $^{13}$C-NMR (150 MHz, d$_6$-DMSO): δ 161.16, 160.30, 158.61, 149.96, 149.94, 146.56, 138.92, 138.76, 132.32, 131.61, 131.14, 130.89, 130.87, 130.18, 128.99, 128.54, 128.21, 127.65, 127.60, 127.43, 126.75, 125.74, 125.71, 125.00, 124.23, 124.11, 121.58, 116.41, 81.93, 63.54, 21.61; $^{19}$F-NMR (564 MHz, d$_6$-DMSO): δ −126.15; HR-ESIMS: m/z 563.1415 [M+H]+(calcd for C$_{33}$H$_{23}$FN$_2$O$_4$S: 562.1363).

Example 2: Docking Studies

Prior to the synthesis extensive docking studies were carried out against ten human proteins that are mainly responsible for cancers. These proteins include Cytidine deaminase (CDA, PDB ID: IMQ0), Ribonucleotide reductase (RNR, PDB ID: 2WGH), Thymidylate synthase (TS, PDB ID: 1HVY), Thymidylate phosphorylase (PDB ID: 1UOU), Topoisomerase II (PDB ID: 4FM9), Protein phosphatase 2A (PP2A, PDB ID: 2IE3), Aminopeptidase N (APN, PDB ID: 4FYR), β-Tubulin (PDB ID: 3M8O), cMet Kinase (PDB ID: 2WD1) and Kras (PDB ID: 4 EPV). In all the cases, five frontline anticancer drugs (Taxol, Adriamycin/Doxorubicin, Gemcitabine, Vincristine and Colchicine) have been compared as positive controls. The positive controls were chosen from diverse origins such as plant, microbes, synthetic and, semi-synthetic. The protein-ligand docking results are presented in tabular form (Tables 1-12) considering the letter code of the 12 compounds (Scheme 1).

TABLE 1

Docking scores (binding energy in kcal/mol) of the compound [A, FIG. 1] with 10 major cancer-causing proteins including drug-resistance K-Ras protein

| | | Binding Affinity (kcal/mol) | | | | | |
|---|---|---|---|---|---|---|---|
| PDB-ID | Target Name | A | Colchicine | Vincristine | Doxorubicin | Gemcitabine | Taxol |
| 1HVY | Thymidylate Synthase | −4.9 | −0.2 | 5.5 | −1.6 | −7.1 | 26.8 |
| 1MQO | Cytidine Deaminase | −6.6 | −5.4 | −5.4 | −6.0 | −5.7 | −5.8 |
| 1UOU | Thymidine Phosphorylase | −6.8 | −5.6 | −0.8 | −5.3 | −8.1 | −4.0 |
| 2IE3 | Protein Phosphatase 2A | −7.9 | −6.1 | −7.6 | −7.4 | −6.7 | −6.6 |
| 2WD1 | c-Met Kinase | −9.7 | −6.5 | −7.4 | −8.7 | −6.3 | −9.3 |
| 2WGH | Ribonucleotide Reductase R1 | −7.8 | −5.8 | −6.4 | −7.9 | −7.0 | −7.0 |
| 3M8O | IgA1 Fab fragment | −9.3 | −7.2 | −9.7 | −8.4 | −6.3 | −9.3 |
| 4EPV | K-Ras | −7.2 | −4.9 | −7.1 | −6.5 | −7.3 | −5.6 |
| 4FM9 | Topoisomerase II | −9.7 | −6.2 | −1.0 | −8.5 | −6.8 | −8.2 |
| 4FYR | Aminopeptidase N | −10.5 | −6.8 | −8.9 | −10.2 | −7.1 | −9.1 |

"PDB-ID" indicates the Protein Data Bank identifier.

TABLE 2

Docking scores (binding energy in kcal/mol) of the compound [B, FIG. 1] with 10 major cancer-causing proteins including drug-resistance K-Ras protein

| | | Binding Affinity (kcal/mol) | | | | | |
|---|---|---|---|---|---|---|---|
| PDB-ID | Target Name | B | Colchicine | Vincristine | Doxorubicin | Gemcitabine | Taxol |
| 1HVY | Thymidylate Synthase | −5.9 | −0.2 | 5.5 | −1.6 | −7.1 | 26.8 |
| 1MQO | Cytidine Deaminase | −6.9 | −5.4 | −5.4 | −6.0 | −5.7 | −5.8 |
| 1UOU | Thymidine Phosphorylase | −6.9 | −5.6 | −0.8 | −5.3 | −8.1 | −4.0 |
| 2IE3 | Protein Phosphatase 2A | −8.0 | −6.1 | −7.6 | −7.4 | −6.7 | −6.6 |
| 2WD1 | c-Met Kinase | −9.7 | −6.5 | −7.4 | −8.7 | −6.3 | −9.3 |
| 2WGH | Ribonucleotide Reductase R1 | −7.5 | −5.8 | −6.4 | −7.9 | −7.0 | −7.0 |
| 3M8O | IgA1 Fab fragment | −9.9 | −7.2 | −9.7 | −8.4 | −6.3 | −9.3 |
| 4EPV | K-Ras | −7.4 | −4.9 | −7.1 | −6.5 | −7.3 | −5.6 |
| 4FM9 | Topoisomerase II | −9.6 | −6.2 | −1.0 | −8.5 | −6.8 | −8.2 |
| 4FYR | Aminopeptidase N | −11.4 | −6.8 | −8.9 | −10.2 | −7.1 | −9.1 |

TABLE 3

Docking scores (binding energy in kcal/mol) of the compound [C, FIG. 1] with 10 major cancer-causing proteins including drug-resistance K-Ras protein

| | | Binding Affinity (kcal/mol) | | | | | |
|---|---|---|---|---|---|---|---|
| PDB-ID | Target Name | C | Colchicine | Vincristine | Doxorubicin | Gemcitabine | Taxol |
| 1HVY | Thymidylate Synthase | 8.3 | −0.2 | 5.5 | −1.6 | −7.1 | 26.8 |
| 1MQO | Cytidine Deaminase | −6.5 | −5.4 | −5.4 | −6.0 | −5.7 | −5.8 |
| 1UOU | Thymidine Phosphorylase | −7.4 | −5.6 | −0.8 | −5.3 | −8.1 | −4.0 |
| 2IE3 | Protein Phosphatase 2A | −8.6 | −6.1 | −7.6 | −7.4 | −6.7 | −6.6 |
| 2WD1 | c-Met Kinase | −10.5 | −6.5 | −7.4 | −8.7 | −6.3 | −9.3 |
| 2WGH | Ribonucleotide Reductase R1 | −8.1 | −5.8 | −6.4 | −7.9 | −7.0 | −7.0 |
| 3M8O | IgA1 Fab fragment | −9.8 | −7.2 | −9.7 | −8.4 | −6.3 | −9.3 |
| 4EPV | K-Ras | −8.1 | −4.9 | −7.1 | −6.5 | −7.3 | −5.6 |
| 4FM9 | Topoisomerase II | −10.6 | −6.2 | −1.0 | −8.5 | −6.8 | −8.2 |
| 4FYR | Aminopeptidase N | −11.1 | −6.8 | −8.9 | −10.2 | −7.1 | −9.1 |

TABLE 4

Docking scores (binding energy in kcal/mol) of the compound [D, FIG. 1] with 10 major cancer-causing proteins including drug-resistance K-Ras protein

| | | Binding Affinity (kcal/mol) | | | | | |
|---|---|---|---|---|---|---|---|
| PDB-ID | Target Name | D | Colchicine | Vincristine | Doxorubicin | Gemcitabine | Taxol |
| 1HVY | Thymidylate Synthase | 5.0 | −0.2 | 5.5 | −1.6 | −7.1 | 26.8 |
| 1MQO | Cytidine Deaminase | −6.9 | −5.4 | −5.4 | −6.0 | −5.7 | −5.8 |
| 1UOU | Thymidine Phosphorylase | −7.1 | −5.6 | −0.8 | −5.3 | −8.1 | −4.0 |
| 2IE3 | Protein Phosphatase 2A | −8.1 | −6.1 | −7.6 | −7.4 | −6.7 | −6.6 |
| 2WD1 | c-Met Kinase | −10.1 | −6.5 | −7.4 | −8.7 | −6.3 | −9.3 |

TABLE 4-continued

Docking scores (binding energy in kcal/mol) of the compound [D, FIG. 1] with 10 major cancer-causing proteins including drug-resistance K-Ras protein

| | | Binding Affinity (kcal/mol) | | | | | |
|---|---|---|---|---|---|---|---|
| PDB-ID | Target Name | D | Colchicine | Vincristine | Doxorubicin | Gemcitabine | Taxol |
| 2WGH | Ribonucleotide Reductase R1 | −8.1 | −5.8 | −6.4 | −7.9 | −7.0 | −7.0 |
| 3M8O | IgA1 Fab fragment | −10.1 | −7.2 | −9.7 | −8.4 | −6.3 | −9.3 |
| 4EPV | K-Ras | −9.7 | −4.9 | −7.1 | −6.5 | −7.3 | −5.6 |
| 4FM9 | Topoisomerase II | −9.8 | −6.2 | −1.0 | −8.5 | −6.8 | −8.2 |
| 4FYR | Aminopeptidase N | −11.3 | −6.8 | −8.9 | −10.2 | −7.1 | −9.1 |

TABLE 5

Docking scores (binding energy in kcal/mol) of the compound [E, FIG. 1] with 10 major cancer-causing proteins including drug-resistance K-Ras protein

| | | Binding Affinity (kcal/mol) | | | | | |
|---|---|---|---|---|---|---|---|
| PDB-ID | Target Name | E | Colchicine | Vincristine | Doxorubicin | Gemcitabine | Taxol |
| 1HVY | Thymidylate Synthase | −5.4 | −0.2 | 5.5 | −1.6 | −7.1 | 26.8 |
| 1MQO | Cytidine Deaminase | −6.7 | −5.4 | −5.4 | −6.0 | −5.7 | −5.8 |
| 1UOU | Thymidine Phosphorylase | −7.0 | −5.6 | −0.8 | −5.3 | −8.1 | −4.0 |
| 2IE3 | Protein Phosphatase 2A | −8.0 | −6.1 | −7.6 | −7.4 | −6.7 | −6.6 |
| 2WD1 | c-Met Kinase | −9.8 | −6.5 | −7.4 | −8.7 | −6.3 | −9.3 |
| 2WGH | Ribonucleotide Reductase R1 | −7.8 | −5.8 | −6.4 | −7.9 | −7.0 | −7.0 |
| 3M8O | IgA1 Fab fragment | −9.8 | −7.2 | −9.7 | −8.4 | −6.3 | −9.3 |
| 4EPV | K-Ras | −8.0 | −4.9 | −7.1 | −6.5 | −7.3 | −5.6 |
| 4FM9 | Topoisomerase II | −9.5 | −6.2 | −1.0 | −8.5 | −6.8 | −8.2 |
| 4FYR | Aminopeptidase N | −11.1 | −6.8 | −8.9 | −10.2 | −7.1 | −9.1 |

TABLE 6

Docking scores (binding energy in kcal/mol) of the compound [F, FIG. 1] with 10 major cancer-causing proteins including drug-resistance K-Ras protein

| | | Binding Affinity (kcal/mol) | | | | | |
|---|---|---|---|---|---|---|---|
| PDB-ID | Target Name | F | Colchicine | Vincristine | Doxorubicin | Gemcitabine | Taxol |
| 1HVY | Thymidylate Synthase | 2.0 | −0.2 | 5.5 | −1.6 | −7.1 | 26.8 |
| 1MQO | Cytidine Deaminase | −6.3 | −5.4 | −5.4 | −6.0 | −5.7 | −5.8 |
| 1UOU | Thymidine Phosphorylase | −7.2 | −5.6 | −0.8 | −5.3 | −8.1 | −4.0 |
| 2IE3 | Protein Phosphatase 2A | −7.6 | −6.1 | −7.6 | −7.4 | −6.7 | −6.6 |
| 2WD1 | c-Met Kinase | −10.0 | −6.5 | −7.4 | −8.7 | −6.3 | −9.3 |
| 2WGH | Ribonucleotide Reductase R1 | −7.0 | −5.8 | −6.4 | −7.9 | −7.0 | −7.0 |
| 3M8O | IgA1 Fab fragment | −9.2 | −7.2 | −9.7 | −8.4 | −6.3 | −9.3 |
| 4EPV | K-Ras | −7.1 | −4.9 | −7.1 | −6.5 | −7.3 | −5.6 |
| 4FM9 | Topoisomerase II | −8.9 | −6.2 | −1.0 | −8.5 | −6.8 | −8.2 |
| 4FYR | Aminopeptidase N | −10.6 | −6.8 | −8.9 | −10.2 | −7.1 | −9.1 |

TABLE 7

Docking scores (binding energy in kcal/mol) of the compound [G, FIG. 1] with 10 major cancer-causing proteins including drug-resistance K-Ras protein

| | | Binding Affinity (kcal/mol) | | | | | |
|---|---|---|---|---|---|---|---|
| PDB-ID | Target Name | G | Colchicine | Vincristine | Doxorubicin | Gemcitabine | Taxol |
| 1HVY | Thymidylate Synthase | 6.1 | −0.2 | 5.5 | −1.6 | −7.1 | 26.8 |
| 1MQO | Cytidine Deaminase | −7.4 | −5.4 | −5.4 | −6.0 | −5.7 | −5.8 |
| 1UOU | Thymidine Phosphorylase | −7.5 | −5.6 | −0.8 | −5.3 | −8.1 | −4.0 |
| 2IE3 | Protein Phosphatase 2A | −8.3 | −6.1 | −7.6 | −7.4 | −6.7 | −6.6 |
| 2WD1 | c-Met Kinase | −9.9 | −6.5 | −7.4 | −8.7 | −6.3 | −9.3 |
| 2WGH | Ribonucleotide Reductase R1 | −8.0 | −5.8 | −6.4 | −7.9 | −7.0 | −7.0 |
| 3M8O | IgA1 Fab fragment | −10.0 | −7.2 | −9.7 | −8.4 | −6.3 | −9.3 |
| 4EPV | K-Ras | −7.9 | −4.9 | −7.1 | −6.5 | −7.3 | −5.6 |
| 4FM9 | Topoisomerase II | −10.7 | −6.2 | −1.0 | −8.5 | −6.8 | −8.2 |
| 4FYR | Aminopeptidase N | −11.6 | −6.8 | −8.9 | −10.2 | −7.1 | −9.1 |

TABLE 8

Docking scores (binding energy in kcal/mol) of the compound [H, FIG. 1] with 10 major cancer-causing proteins including drug-resistance K-Ras protein

| | | Binding Affinity (kcal/mol) | | | | | |
|---|---|---|---|---|---|---|---|
| PDB-ID | Target Name | H | Colchicine | Vincristine | Doxorubicin | Gemcitabine | Taxol |
| 1HVY | Thymidylate Synthase | 2.4 | −0.2 | 5.5 | −1.6 | −7.1 | 26.8 |
| 1MQO | Cytidine Deaminase | −6.6 | −5.4 | −5.4 | −6.0 | −5.7 | −5.8 |
| 1UOU | Thymidine Phosphorylase | −7.1 | −5.6 | −0.8 | −5.3 | −8.1 | −4.0 |
| 2IE3 | Protein Phosphatase 2A | −7.9 | −6.1 | −7.6 | −7.4 | −6.7 | −6.6 |
| 2WD1 | c-Met Kinase | −9.6 | −6.5 | −7.4 | −8.7 | −6.3 | −9.3 |
| 2WGH | Ribonucleotide Reductase R1 | −7.6 | −5.8 | −6.4 | −7.9 | −7.0 | −7.0 |
| 3M8O | IgA1 Fab fragment | −9.9 | −7.2 | −9.7 | −8.4 | −6.3 | −9.3 |
| 4EPV | K-Ras | −8.4 | −4.9 | −7.1 | −6.5 | −7.3 | −5.6 |
| 4FM9 | Topoisomerase II | −9.5 | −6.2 | −1.0 | −8.5 | −6.8 | −8.2 |
| 4FYR | Aminopeptidase N | −11.0 | −6.8 | −8.9 | −10.2 | −7.1 | −9.1 |

TABLE 9

Docking scores (binding energy in kcal/mol) of the compound [I, FIG. 1] with 10 major cancer-causing proteins including drug-resistance K-Ras protein

| | | Binding Affinity (kcal/mol) | | | | | |
|---|---|---|---|---|---|---|---|
| PDB-ID | Target Name | I | Colchicine | Vincristine | Doxorubicin | Gemcitabine | Taxol |
| 1HVY | Thymidylate Synthase | −6.3 | −0.2 | 5.5 | −1.6 | −7.1 | 26.8 |
| 1MQO | Cytidine Deaminase | −7.8 | −5.4 | −5.4 | −6.0 | −5.7 | −5.8 |
| 1UOU | Thymidine Phosphorylase | −7.4 | −5.6 | −0.8 | −5.3 | −8.1 | −4.0 |
| 2IE3 | Protein Phosphatase 2A | −8.5 | −6.1 | −7.6 | −7.4 | −6.7 | −6.6 |
| 2WD1 | c-Met Kinase | −10.3 | −6.5 | −7.4 | −8.7 | −6.3 | −9.3 |
| 2WGH | Ribonucleotide Reductase R1 | −7.7 | −5.8 | −6.4 | −7.9 | −7.0 | −7.0 |
| 3M8O | IgA1 Fab fragment | −9.8 | −7.2 | −9.7 | −8.4 | −6.3 | −9.3 |
| 4EPV | K-Ras | −8.1 | −4.9 | −7.1 | −6.5 | −7.3 | −5.6 |
| 4FM9 | Topoisomerase II | −10.4 | −6.2 | −1.0 | −8.5 | −6.8 | −8.2 |
| 4FYR | Aminopeptidase N | −10.9 | −6.8 | −8.9 | −10.2 | −7.1 | −9.1 |

TABLE 10

Docking scores (binding energy in kcal/mol) of the compound [J, FIG. 1] with 10 major cancer-causing proteins including drug-resistance K-Ras protein

| | | Binding Affinity (kcal/mol) | | | | | |
|---|---|---|---|---|---|---|---|
| PDB-ID | Target Name | J | Colchicine | Vincristine | Doxorubicin | Gemcitabine | Taxol |
| 1HVY | Thymidylate Synthase | −5.8 | −0.2 | 5.5 | −1.6 | −7.1 | 26.8 |
| 1MQO | Cytidine Deaminase | −6.6 | −5.4 | −5.4 | −6.0 | −5.7 | −5.8 |
| 1UOU | Thymidine Phosphorylase | −6.8 | −5.6 | −0.8 | −5.3 | −8.1 | −4.0 |
| 2IE3 | Protein Phosphatase 2A | −7.7 | −6.1 | −7.6 | −7.4 | −6.7 | −6.6 |
| 2WD1 | c-Met Kinase | −9.7 | −6.5 | −7.4 | −8.7 | −6.3 | −9.3 |
| 2WGH | Ribonucleotide Reductase R1 | −7.7 | −5.8 | −6.4 | −7.9 | −7.0 | −7.0 |
| 3M8O | IgA1 Fab fragment | −9.4 | −7.2 | −9.7 | −8.4 | −6.3 | −9.3 |
| 4EPV | K-Ras | −10.3 | −4.9 | −7.1 | −6.5 | −7.3 | −5.6 |
| 4FM9 | Topoisomerase II | −9.7 | −6.2 | −1.0 | −8.5 | −6.8 | −8.2 |
| 4FYR | Aminopeptidase N | −10.8 | −6.8 | −8.9 | −10.2 | −7.1 | −9.1 |

TABLE 11

Docking scores (binding energy in kcal/mol) of the compound [K, FIG. 1] with 10 major cancer-causing proteins including drug-resistance K-Ras protein

| | | Binding Affinity (kcal/mol) | | | | | |
|---|---|---|---|---|---|---|---|
| PDB-ID | Target Name | K | Colchicine | Vincristine | Doxorubicin | Gemcitabine | Taxol |
| 1HVY | Thymidylate Synthase | −6.4 | −0.2 | 5.5 | −1.6 | −7.1 | 26.8 |
| 1MQO | Cytidine Deaminase | −7.4 | −5.4 | −5.4 | −6.0 | −5.7 | −5.8 |
| 1UOU | Thymidine Phosphorylase | −7.0 | −5.6 | −0.8 | −5.3 | −8.1 | −4.0 |
| 2IE3 | Protein Phosphatase 2A | −8.1 | −6.1 | −7.6 | −7.4 | −6.7 | −6.6 |
| 2WD1 | c-Met Kinase | −9.9 | −6.5 | −7.4 | −8.7 | −6.3 | −9.3 |
| 2WGH | Ribonucleotide Reductase R1 | −7.8 | −5.8 | −6.4 | −7.9 | −7.0 | −7.0 |

TABLE 11-continued

Docking scores (binding energy in kcal/mol) of the compound [K, FIG. 1] with 10 major cancer-causing proteins including drug-resistance K-Ras protein

| PDB-ID | Target Name | Binding Affinity (kcal/mol) | | | | |
|---|---|---|---|---|---|---|
| | | K | Colchicine | Vincristine | Doxorubicin | Gemcitabine | Taxol |
| 3M8O | IgA1 Fab fragment | −9.4 | −7.2 | −9.7 | −8.4 | −6.3 | −9.3 |
| 4EPV | K-Ras | −11.1 | −4.9 | −7.1 | −6.5 | −7.3 | −5.6 |
| 4FM9 | Topoisomerase II | −9.8 | −6.2 | −1.0 | −8.5 | −6.8 | −8.2 |
| 4FYR | Aminopeptidase N | −9.9 | −6.8 | −8.9 | −10.2 | −7.1 | −9.1 |

TABLE 12

Docking scores (binding energy in kcal/mol) of the compound [L, FIG. 1] with 10 major cancer-causing proteins including drug-resistance K-Ras protein

| PDB-ID | Target Name | Binding Affinity (kcal/mol) | | | | |
|---|---|---|---|---|---|---|
| | | L | Colchicine | Vincristine | Doxorubicin | Gemcitabine | Taxol |
| 1HVY | Thymidylate Synthase | 5.1 | −0.2 | 5.5 | −1.6 | −7.1 | 26.8 |
| 1MQO | Cytidine Deaminase | −7.4 | −5.4 | −5.4 | −6.0 | −5.7 | −5.8 |
| 1UOU | Thymidine Phosphorylase | −7.0 | −5.6 | −0.8 | −5.3 | −8.1 | −4.0 |
| 2IE3 | Protein Phosphatase 2A | −8.7 | −6.1 | −7.6 | −7.4 | −6.7 | −6.6 |
| 2WD1 | c-Met Kinase | −9.9 | −6.5 | −7.4 | −8.7 | −6.3 | −9.3 |
| 2WGH | Ribonucleotide Reductase R1 | −7.9 | −5.8 | −6.4 | −7.9 | −7.0 | −7.0 |
| 3M8O | IgA1 Fab fragment | −10.7 | −7.2 | −9.7 | −8.4 | −6.3 | −9.3 |
| 4EPV | K-Ras | −9.2 | −4.9 | −7.1 | −6.5 | −7.3 | −5.6 |
| 4FM9 | Topoisomerase II | −10.4 | −6.2 | −1.0 | −8.5 | −6.8 | −8.2 |
| 4FYR | Aminopeptidase N | −12.4 | −6.8 | −8.9 | −10.2 | −7.1 | −9.1 |

Example 3: Biological Activity Methods and Materials

A. Druggability Studies (in Silico)

The 'druggability' of the compounds disclosed herein was determined by calculating the (1) miLogP which is Moriguchi octanol-water partition coefficient, is based on quantitative structure-LogP relationships, by using topological indexes; (2) Total polar surface area (TPSA); (3) Hydrogen bond donor (HBD); (4) Hydrogen bond acceptor (HBA); (5) Rotatable bonds (RB); (6) Molecular volume, and (7) Molecular weight (MW). The results are shown in Table B. All the twelve investigational molecules qualified RO5 (Lipinski's rule of five). Taken together, all the twelve molecules possess 'druggability'.

TABLE B

Structure and Druggability Validation[†] of the 12 β-lactam derivatives

| Compound Code (Letter Code) | miLogP[a] | TPSA[b] | HBA[c] | HBD[d] | Violation | RB[e] | Molecular Volume | MW[f] |
|---|---|---|---|---|---|---|---|---|
| A | 4.77 | 76.58 | 6 | 0 | None | 4 | 399.76 | 486.52 |
| B | 4.37 | 76.58 | 6 | 0 | 1 | 6 | 437.51 | 556.54 |
| C | 4.79 | 103.61 | 8 | 0 | 1 | 5 | 452.43 | 552.59 |
| D | 5.43 | 76.58 | 6 | 0 | 2 | 5 | 439.59 | 526.59 |
| E | 5.45 | 79.81 | 7 | 0 | 2 | 6 | 462.49 | 543.62 |
| F | 5.13 | 76.78 | 6 | 0 | 2 | 5 | 422.79 | 512.56 |
| G | 4.66 | 83.05 | 8 | 0 | 1 | 5 | 481.69 | 570.65 |
| H | 7.08 | 76.58 | 6 | 0 | 2 | 7 | 496.04 | 572.73 |
| I | 5.17 | 79.81 | 7 | 0 | 2 | 5 | 452.35 | 541.60 |
| J | 4.77 | 79.81 | 7 | 0 | 1 | 5 | 429.11 | 515.57 |
| K | 4.50 | 106.01 | 8 | 0 | 1 | 5 | 409.10 | 513.51 |
| L | 6.75 | 76.58 | 6 | 0 | 2 | 5 | 471.17 | 562.62 |

[†]Molinspiration property engine v2016.10;

[a]miLogP: Moriguchi octanol-water partition coefficient, is based on quantitative structure-LogP relationships, by using topological indexes;

[b]Total polar surface area;

[c]Hydrogen bond acceptor;

[d]Hydrogen bond donor;

[e]Number of rotatable bonds;

[f]Molecular weight

B. Cytotoxicity Studies: Determination of $IC_{50}$ Values (Single Run) in Capain-2, HPAC. HPAF-II, and HS766T Cell Lines After successful design, in silico validation, and synthesis of the 4-(5-fluoropyridin-2-yl)-2-azetidinones (β-lactams), the next step involved in vitro anticancer evaluation that demonstrated excellent cytotoxicity against an array of four drug-resistant pancreatic cancer cell lines viz. Capan-2, HPAC. HPAF-II, and HS766T. The compounds A, D, E, G, and H were chosen randomly, out of twelve β-laclam molecules, to carry out this evaluation. The compounds disclosed herein (A, D, E, G, and H) demonstrated excellent in silico as well as in vitro cytotoxicity against the Gemcitabine-resistant cell lines (Table C).

TABLE C $IC_{50}$ values (mean ± standard error, in μM) against four drug-resistant pancreatic cancer cell lines.

| Compds. | Cell lines | | | |
|---|---|---|---|---|
| | CaPan-2 | HPAC | HPAF-II | HS 766T |
| DB-3 (OMS)-FDCR (A) | >10 | >10 | 0.98 ± 0.38 | 0.24 ± 0.38 |
| DB-3 (OCS)-CRFD (D) | † | † | 1.39 ± 0.40 | 0.73 ± 0.40 |
| DB-3 (OIS)-CRFD (E) | † | † | 0.50 ± 0.16 | 0.04 ± 0.16 |
| DB-3 (OMP)-FDCR (G) | † | † | 1.18 ± 0.26 | † |
| DB-3(OTMS)-FDCR (H) | † | † | 0.66 ± 0.12 | 0.79 ± 0.12 |
| Gemcitabine (drug) | >50 | >50 | >50 | 16.32 ± 0.6 |

"†" indicates negative $IC_{50}$ values (obtained from calculation).

Figure 1A:
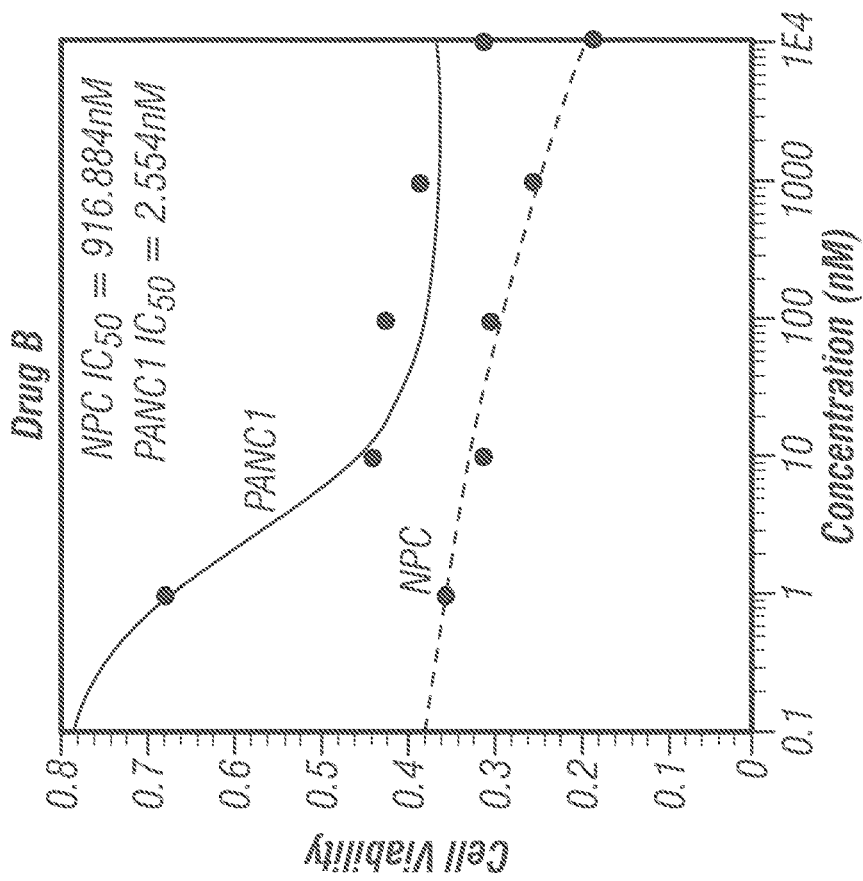
FIGS. 1A-1B show the $IC_{50}$ curves of the twelve investigational β-lactams in pancreatic cancer cells PANC-1 (ATCC CRL-1469) and normal pancreatic ductal epithelial cells (ATCC CRL-4038). The GraphPad Prism software was used to process the results. The $IC_{50}$ values were determined by SRB (Sulforhodamine B) assay following standard procedure. PANC-1 cells were plated in 96 well plates and treated with 1, 10, 100, 1000 and 10,000 nM of each of the drugs in triplicate for 72 hrs. Cells were fixed, washed and stained with SRB dye, the stained cells were washed, and the dye solubilized. It was read using a plate reader at 565 nm. The $IC_{50}$ values were calculated assuming that the 10 μM sample has reached saturation. Following similar way, $IC_{50}$ values were determined for normal pancreatic ductal epithelial cells.
Figure 1A:
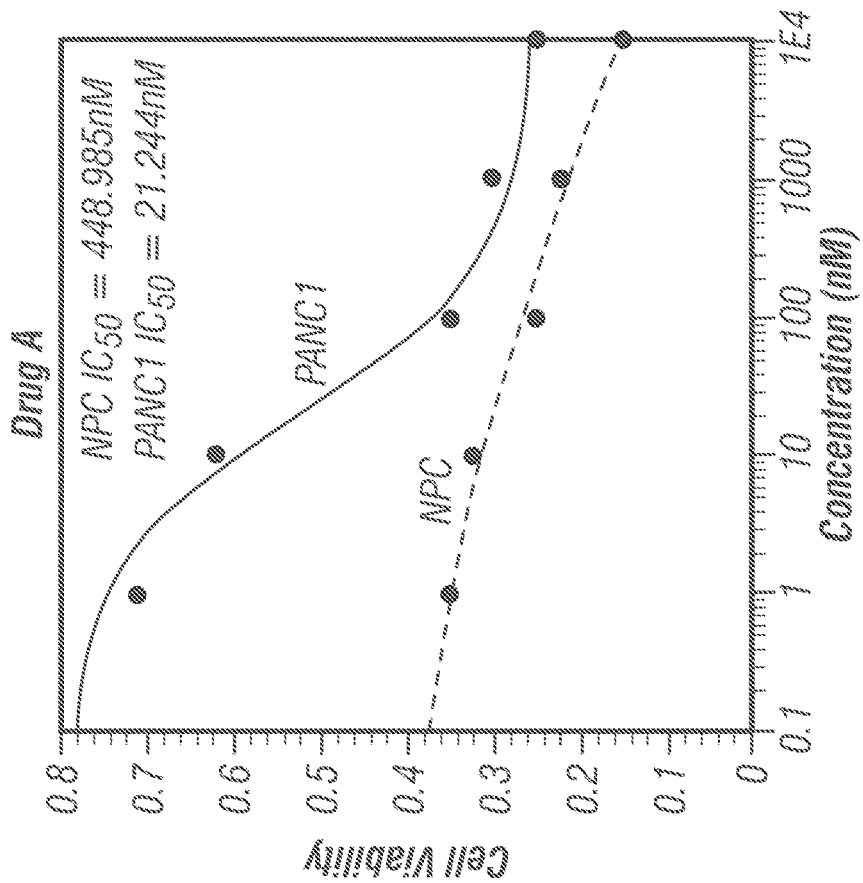
Figure 1A:
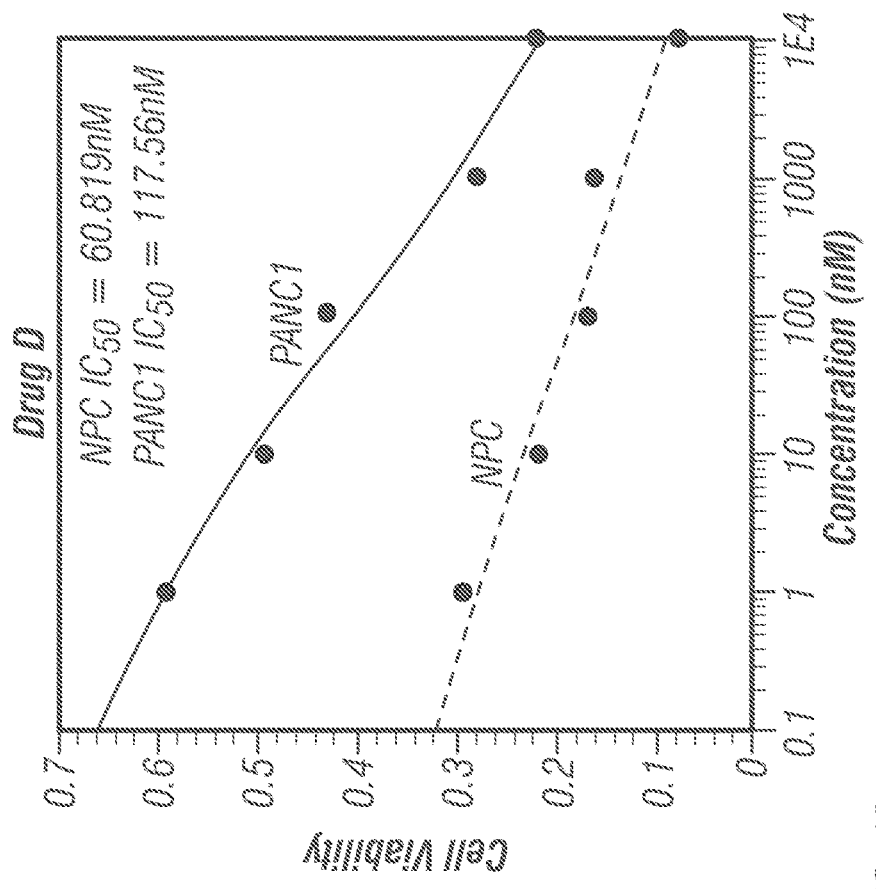
Figure 1A:
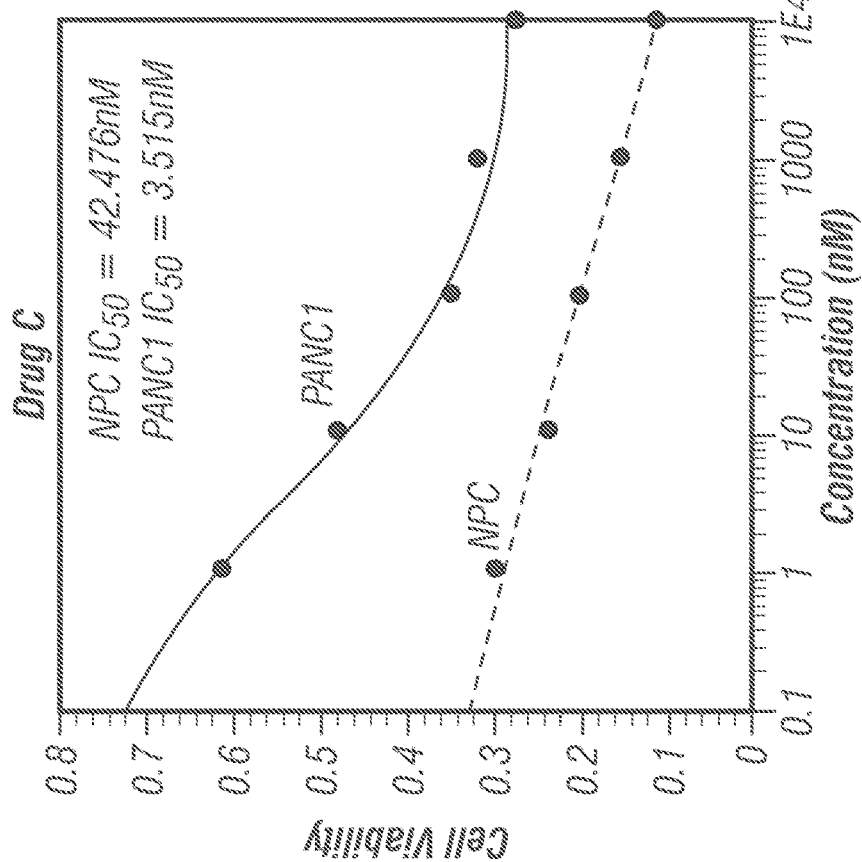
Figure 1A:
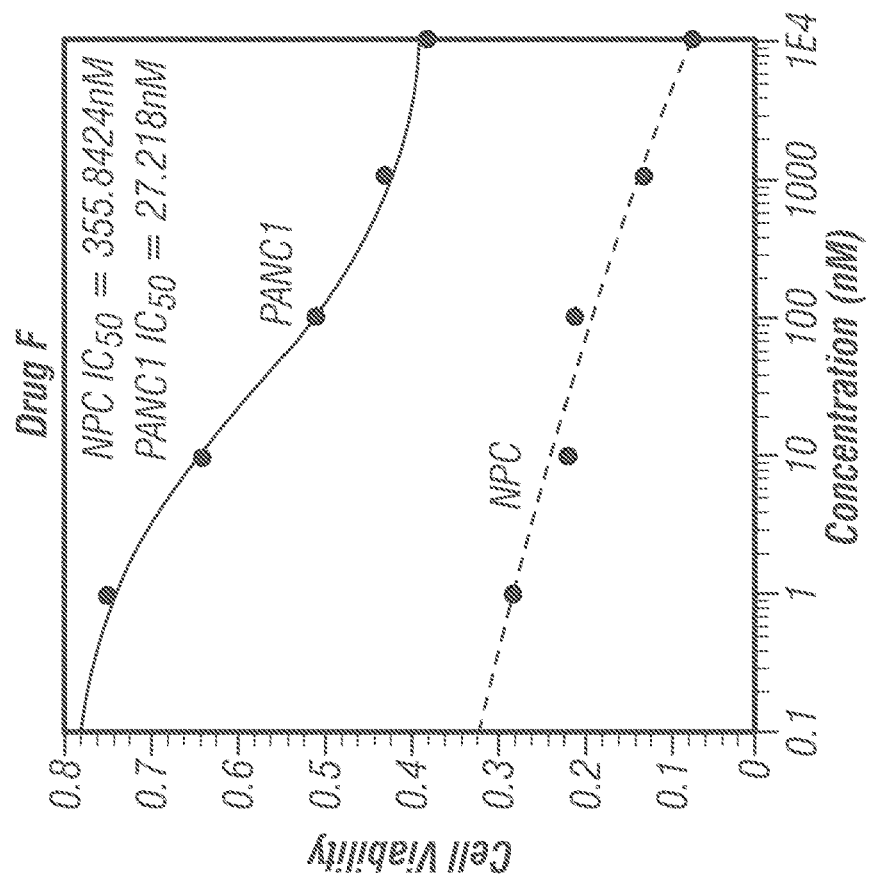
Figure 1A:
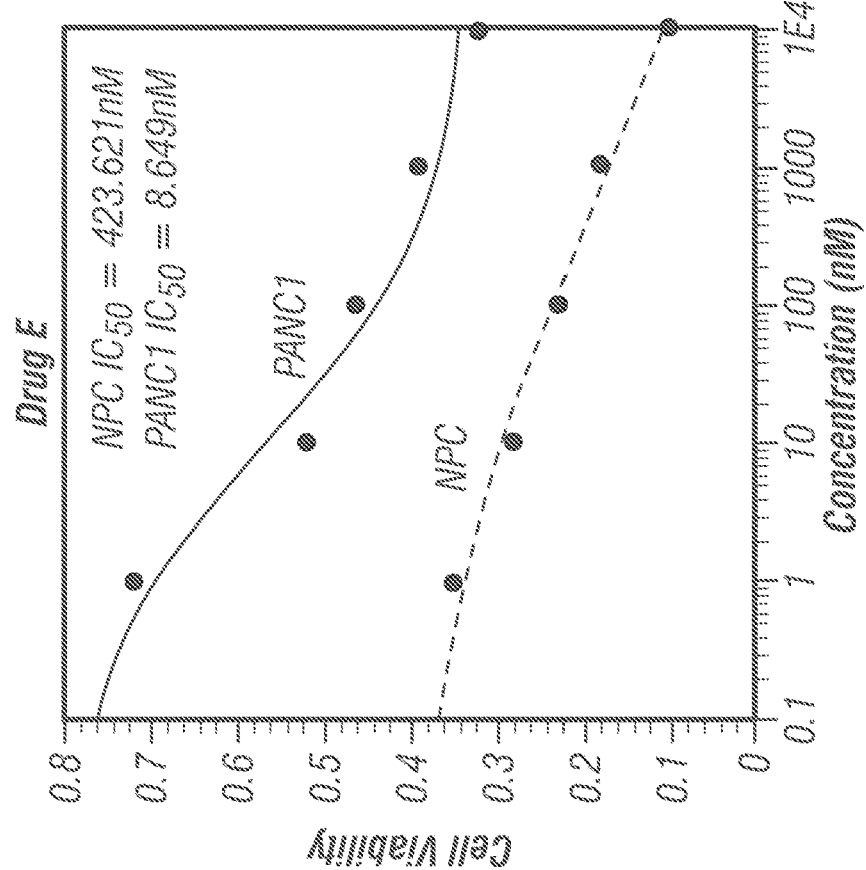
Figure 1B:
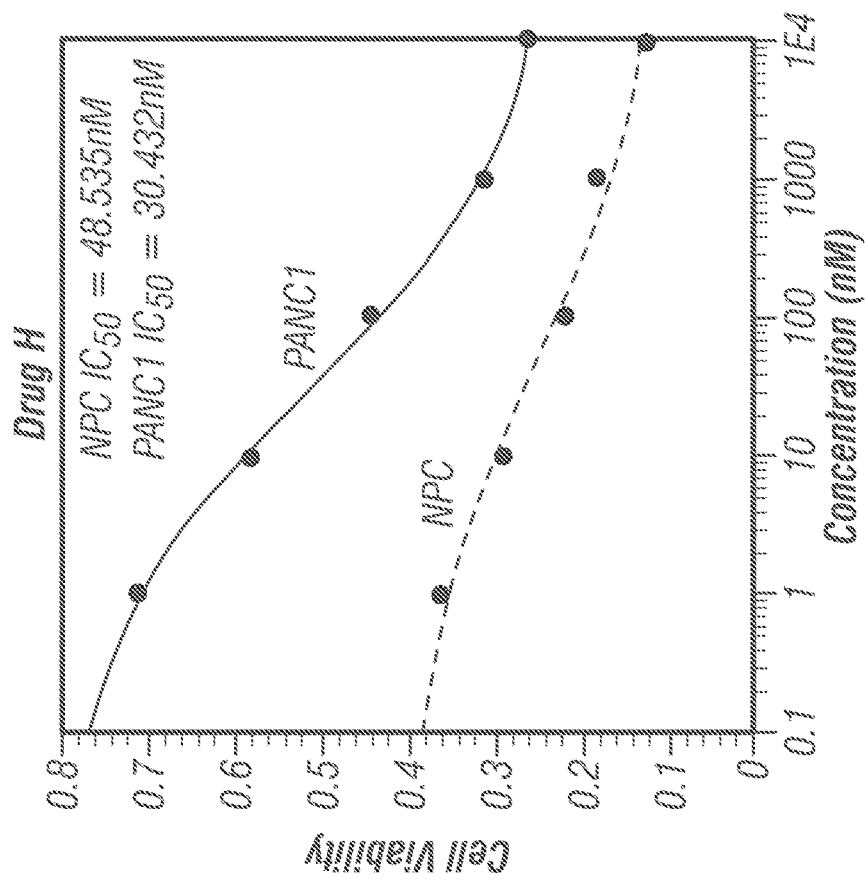
Figure 1B:
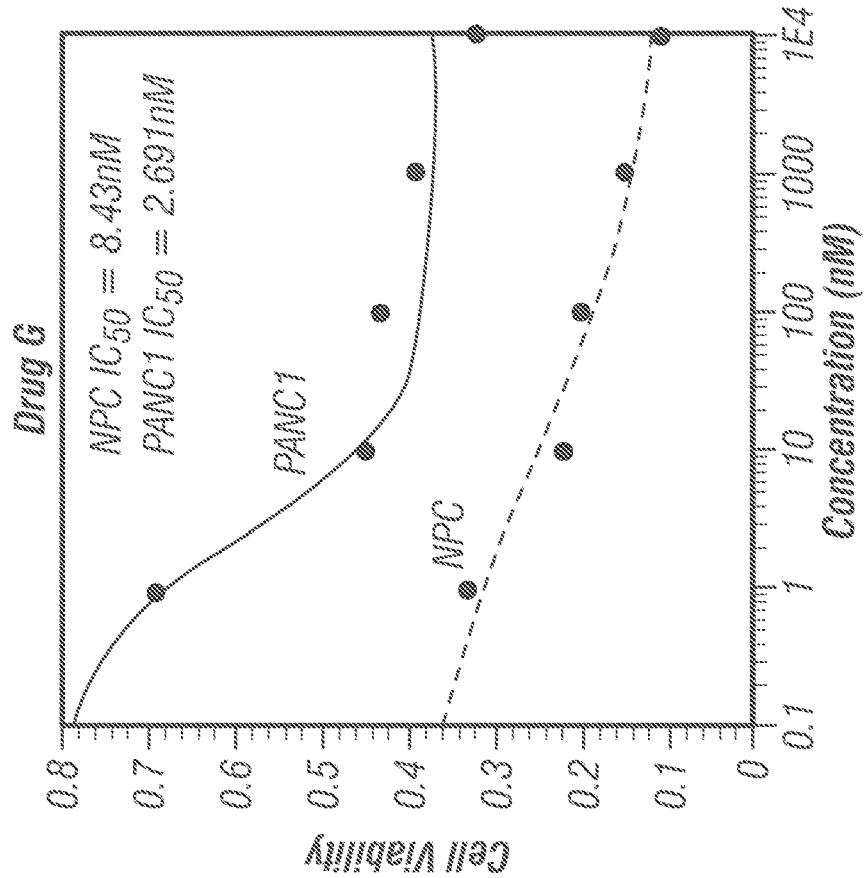
Figure 1B:
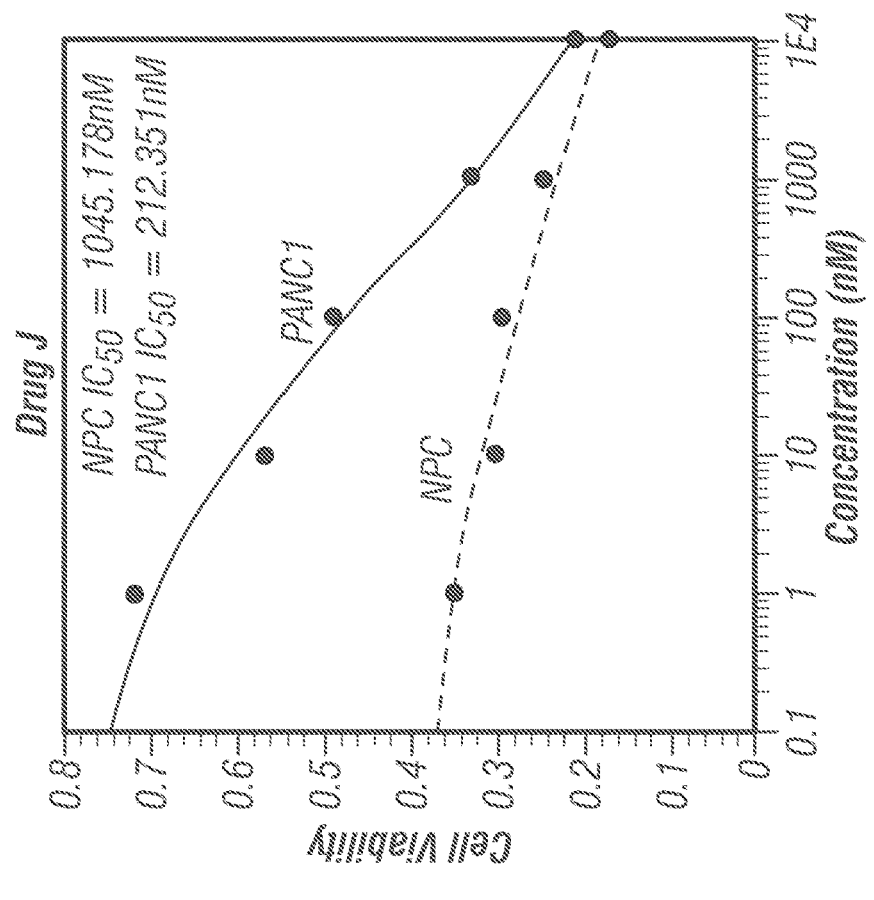
Figure 1B:
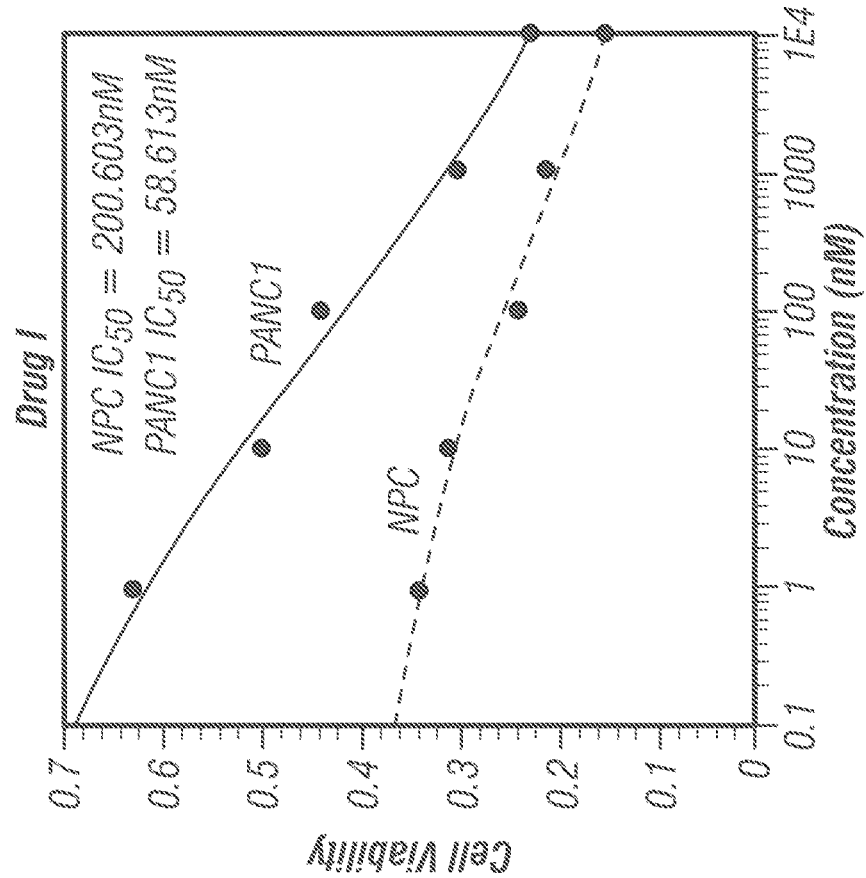
Figure 1B:
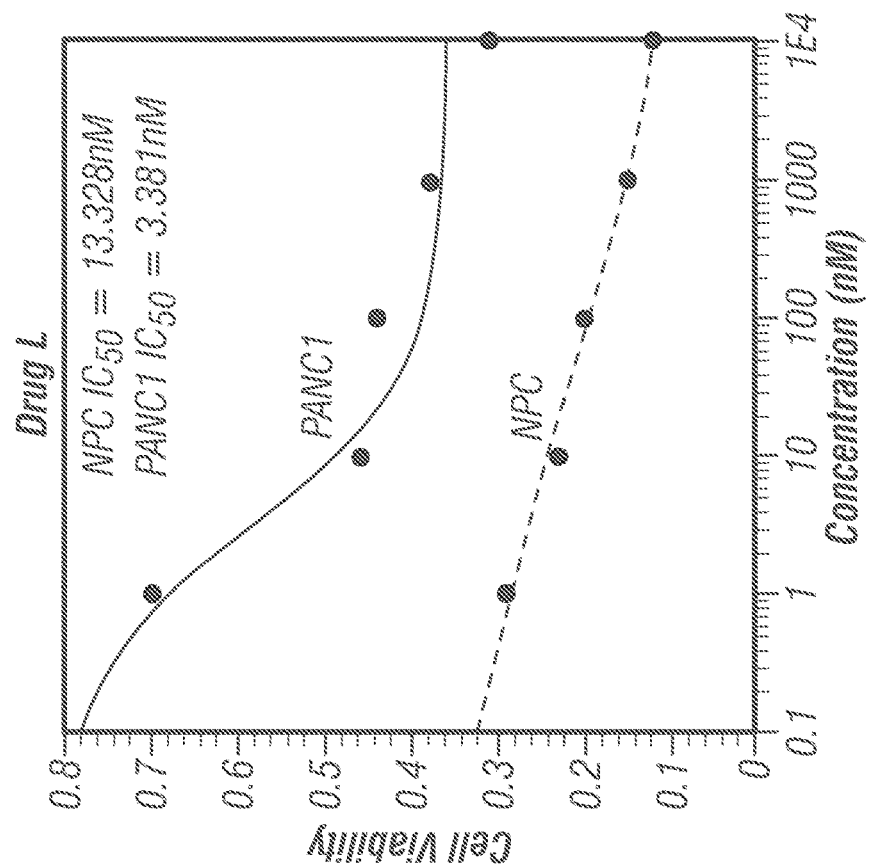
Figure 1B:
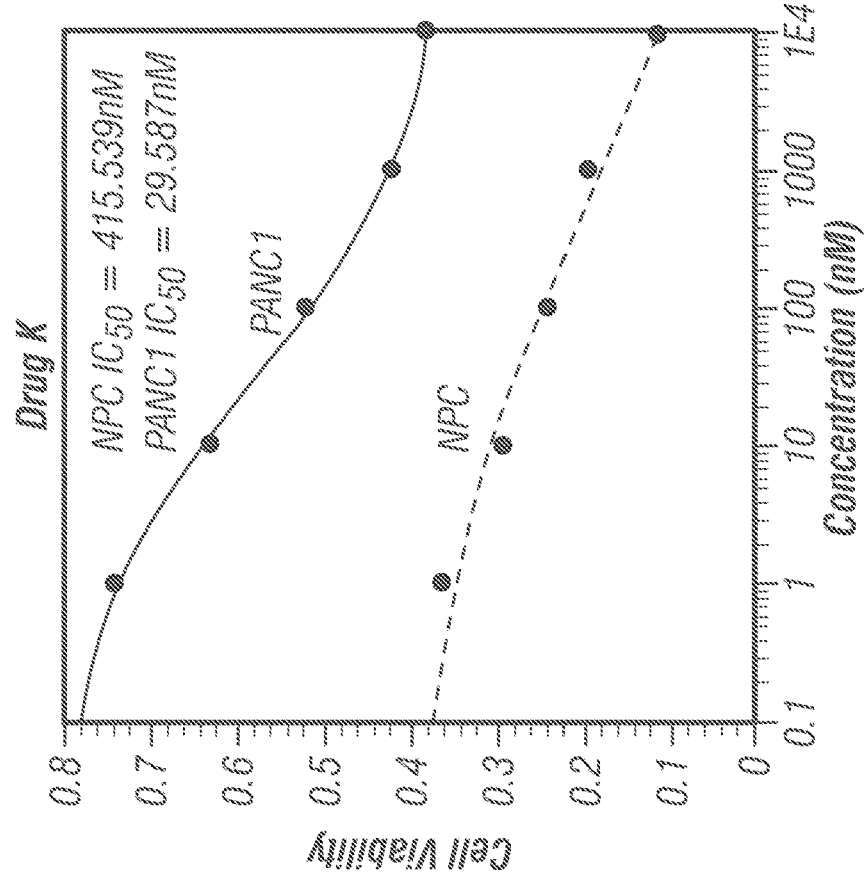

C. Determination of $IC_{50}$ Values (Triplicate) in PANC-1 and Normal Pancreatic Ductal Epithelial Cells As mentioned earlier, PANC-1 is referred to generically as the "gold standard of pancreatic cancers" representing as it does almost total resistance to GEM, the first line treatment currently used in clinical situations. Pancreatic cancer cells PANC-1 (ATCC CRL-1469) and normal pancreatic ductal epithelial cells (ATCC CRL-4038) were used in this study. The GraphPad Prism software was used to process the results. The $IC_{50}$ values were determined by SRB (Sulforhodamine B) assay following standard procedure: PANC-1 cells were plated in 96 well plates and treated with 1, 10, 100, 1000 and 10,000 nM of each of the drugs in triplicate for 72 hrs. Cells were fixed, washed and stained with SRB dye, the stained cells were washed, and the dye solubilized. It was read using a plate reader at 565 nm. The $IC_{50}$ values were calculated assuming that the 10 μM sample has reached saturation. Following similar way, $IC_{50}$ values were determined for normal pancreatic ductal epithelial cells. All the $IC_{50}$ values are shown in Table D. All the twelve molecules demonstrated hundreds to thousands-fold higher activity than the positive control Gemcitabine, the commercially available drug for pancreatic cancer. All the twelve molecules also demonstrated more than 2 to 168 times higher potency than TX-262 (Table D) in PANC-1 cells during in vitro evaluation. Comparison of the $IC_{50}$ values in pancreatic cancer cells (PANC-1) and normal pancreatic epithelial cells (NPC) clearly indicates that almost all the compounds possess 3 to 359 times higher selectivity towards drug-resistance pancreatic cancer cells (PANC-1) compared to normal pancreatic ductal epithelial cells (NPC). The $IC_{50}$ curves are shown in FIGS. 1A-1B.

TABLE D $IC_{50}$ values (in nM, triplicate) of the compounds (A-L) against PANC-1 pancreatic cancer and normal pancreatic ductal epithelial cell (NPC) lines.

| Code | $IC_{50}$ (PANC-1)[b] | $IC_{50}$ (NPC)[b] |
|---|---|---|
| A | 21.244 | 448.985 |
| B | 2.554 | 916.884 |
| C | 3.515 | 42.476 |
| D | 117.564 | 60.819 |
| E | 8.649 | 423.621 |
| F | 27.218 | 355.842 |
| G | 2.691 | 8.43 |
| H | 30.432 | 48.535 |
| I | 58.613 | 200.603 |
| J | 212.351 | 1045.178 |
| K | 29.587 | 415.539 |
| L | 3.381 | 13.328 |
| TX-262[a] | 430 | ND[c] |
| Gemcitabine (control) | 37930 | ND[c] |

[a]Banik et al., WO 2012/103456.
[b]average of 3 runs.
[c]not determined

Figure 2:
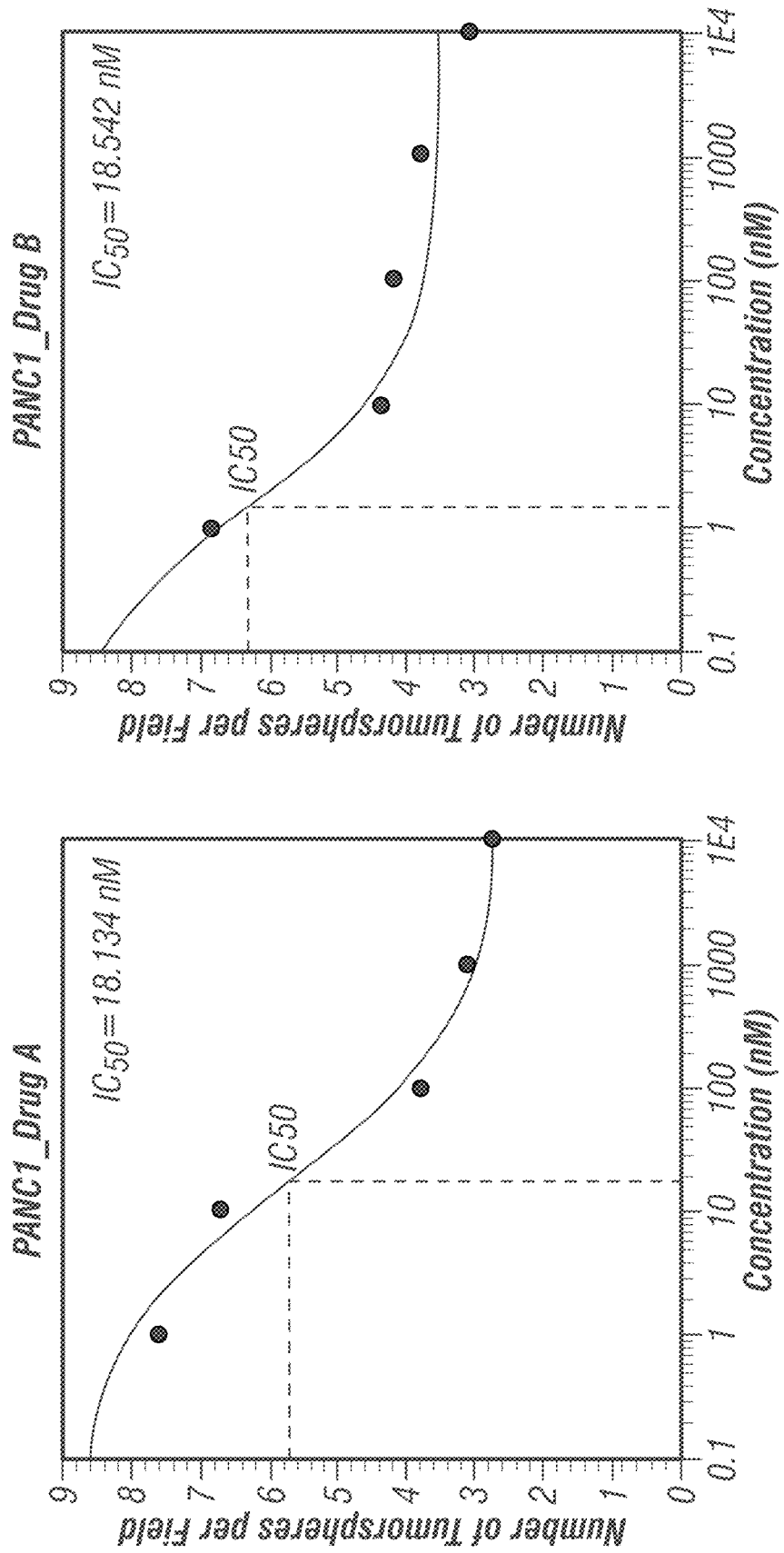
FIG. 2 shows the $IC_{50}$ values of the six investigational β-lactams (A, B, C, E, F, and G) as obtained by 3D-tumorsphere formation assay. Number of tumorspheres formed can be used to distinguish the efficacy of different anticancer drugs in a more physically acceptable method than 2D culture. Based on selectivity and toxicity towards PANC-1 cells in comparison to normal pancreatic ductal epithelial cells (Table D), six compounds (A, B, C, E, F, and G) were chosen for the 3D-tumorsphere formation assay. The assay was carried out by following the protocol developed by Johnson et al., (2013). PANC-1 cells (5000) were plated as single cells in Corning ultra-low attachment 24 well plates in 0.5 ml DMEM+10% FBS. The cells were grown in a humidified atmosphere of 5% $CO_2$ for 168 hrs. 0.1 ml Media was added on 72nd and 144 hrs. The β-lactams were dissolved in DMSO and maintained at −20° C. On the day of assay, on the addition of media, the drugs were freshly diluted in media. The final concentrations of drugs were 0, 1 nM, 10 nM, 100 nM, 1 μM, 10 μM. After 144 hours the total number tumorspheres that were larger than 100 micrometers were counted in a field of 1 mm×1 mm at 10× magnification in a bright field microscope. The data was plotted and the $IC_{50}$ value was calculated.
Figure 2:
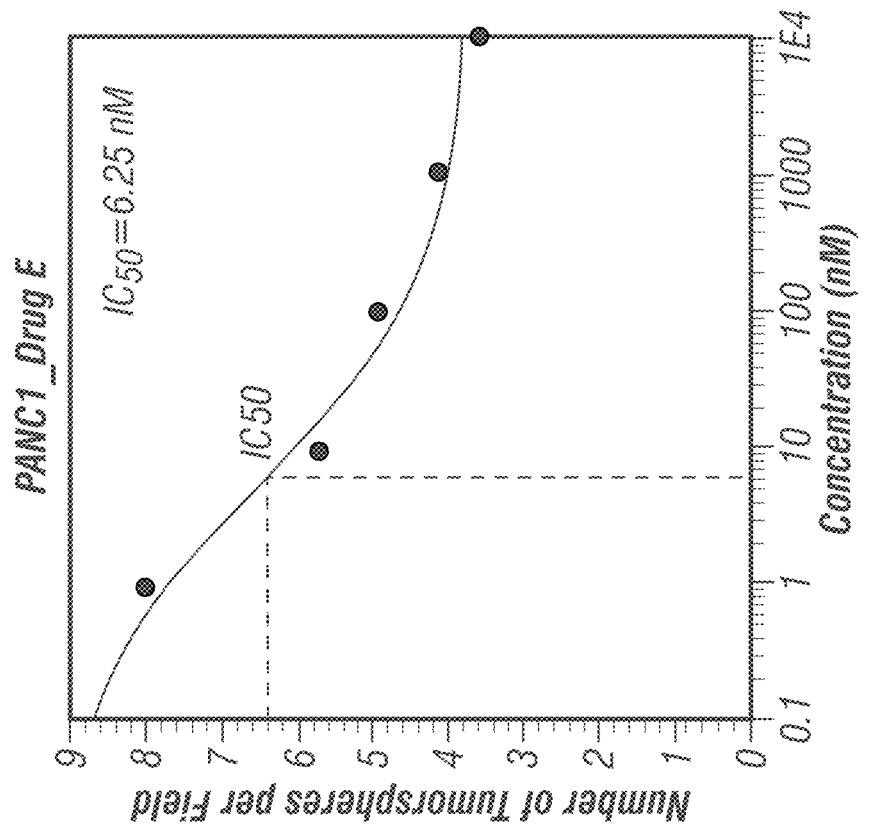
Figure 2:
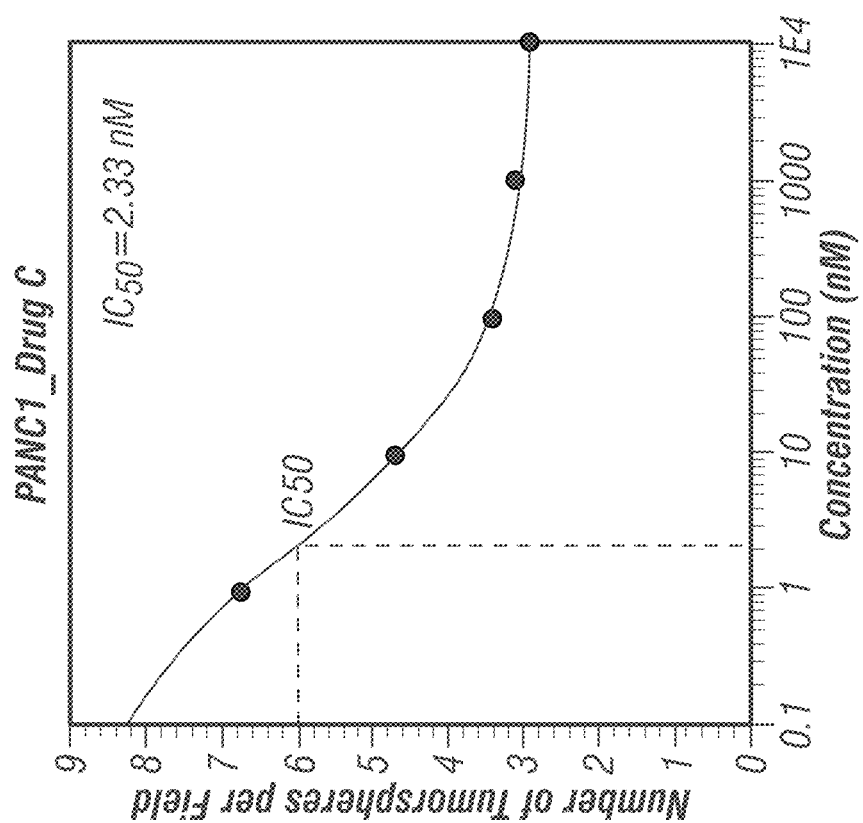
Figure 2:
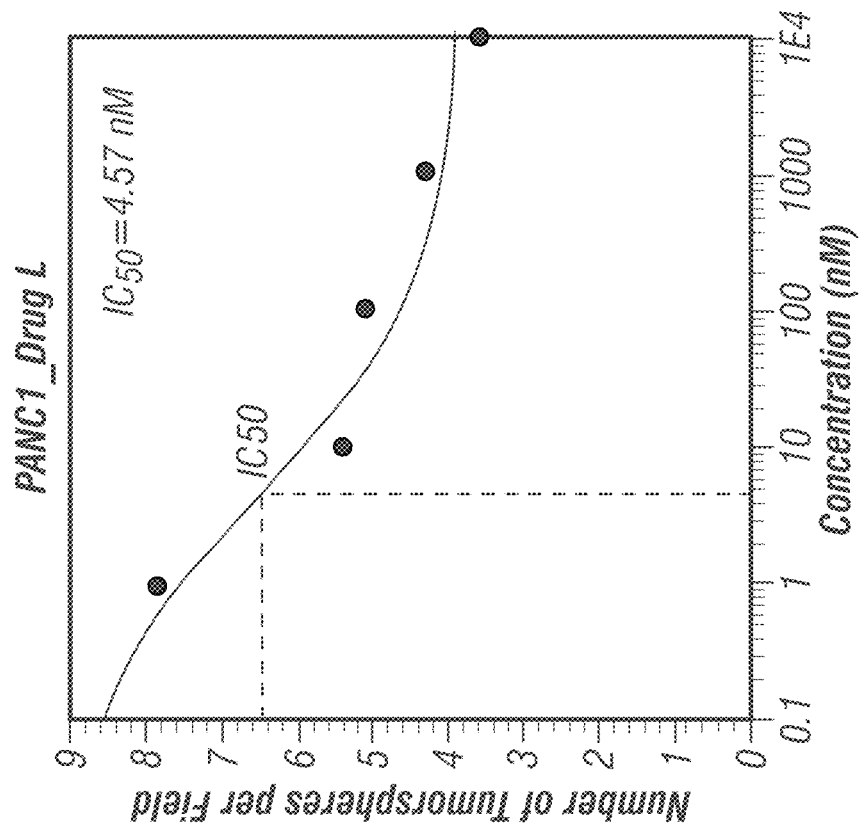
Figure 2:
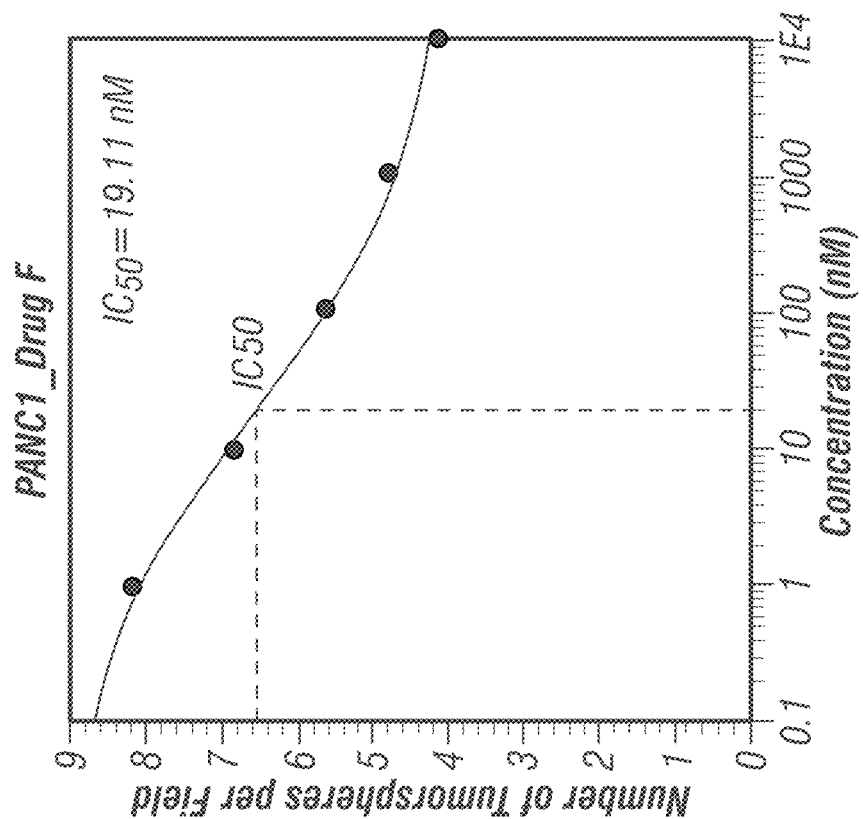

D. 3D-Tumorsphere Formation Assay and Determination of $IC_{50}$ Values in PANC-1 Cells 3D-tumorsphere formation assay is considered to be a fast and economical intermediary step between in vitro and in vivo biological evaluations. A tumorsphere is a solid, spherical formation developed from the proliferation of a single cancer stem/progenitor cell in 3D culture. These cells are easily distinguishable from single or aggregated as they appear to become fused together and individual cells cannot be appearing to become fused together and individual cells cannot be identified. The size can vary from less than 50 micrometers to 250 micrometers. The number of tumorspheres formed can be used to characterize the cancer stem cell population within different in vitro cultured cancer cell lines. The number of tumorspheres formed can also be used to distinguish the efficacy of different anticancer drugs in a more physically acceptable method than 2D culture. Based on selectivity and toxicity towards PANC-1 cells in comparison to normal pancreatic ductal epithelial cells (Table D), six compounds (A, B, C, E, F, and G) were chosen for the 3D-tumorsphere formation assay. The assay was carried out by following the protocol developed by Johnson et al., (2013). Tumorspheres do not form for normal cells. The results are presented in Table E and the $IC_{50}$ curves are presented in FIG. 2. Four out of six tested compounds (A, C, E, and F) demonstrated higher activity in 3D-tumorphere formation assay than 2D-culture (FIG. 2). The below steps were followed to accomplish the assay.

5000 PANC-1 cells were plated as single cells in Corning ultra-low attachment 24 well plates in 0.5 ml DMEM+ 10% FBS.

Cells were grown in a humidified atmosphere of 5% ($CO_2$ for 168 hrs. 0.1 ml Media was added on 72nd and 144 hrs.

Drugs were dissolved in DMSO and maintained at −20° C. On the day of assay, on the addition of media, the drugs were freshly diluted in media.

The final concentrations of drugs were 0, 1 nM, 10 nM, 100 nM, 1 μM, 10 μM.

After 144 hrs the total number tumorspheres that were larger than 100 micrometers were counted in a field of 1 mm×1 mm at 10× magnification in a bright field microscope. The data was plotted and the $IC_{50}$ value was calculated.

TABLE E 3D-tumorsphere formation assay: IC$_{50}$ values (in nM) of the compounds A, B, C, E, F, and L against PANC-1 tumorspheres.

| Code | IC$_{50}$ (PANC-1) (2D-culture) | IC$_{50}$ (PANC-1) 3D-tumorsphere formation assay | IC$_{50}$ (NPC) (2D-culture) |
|---|---|---|---|
| A | 21.244 | 18.134 | 448.985 |
| B | 2.554 | 18.542 | 916.884 |
| C | 3.515 | 2.33 | 42.476 |
| E | 8.649 | 6.25 | 423.621 |
| F | 27.218 | 19.11 | 355.842 |
| L | 3.381 | 4.57 | 13.328 |

Figure 3:
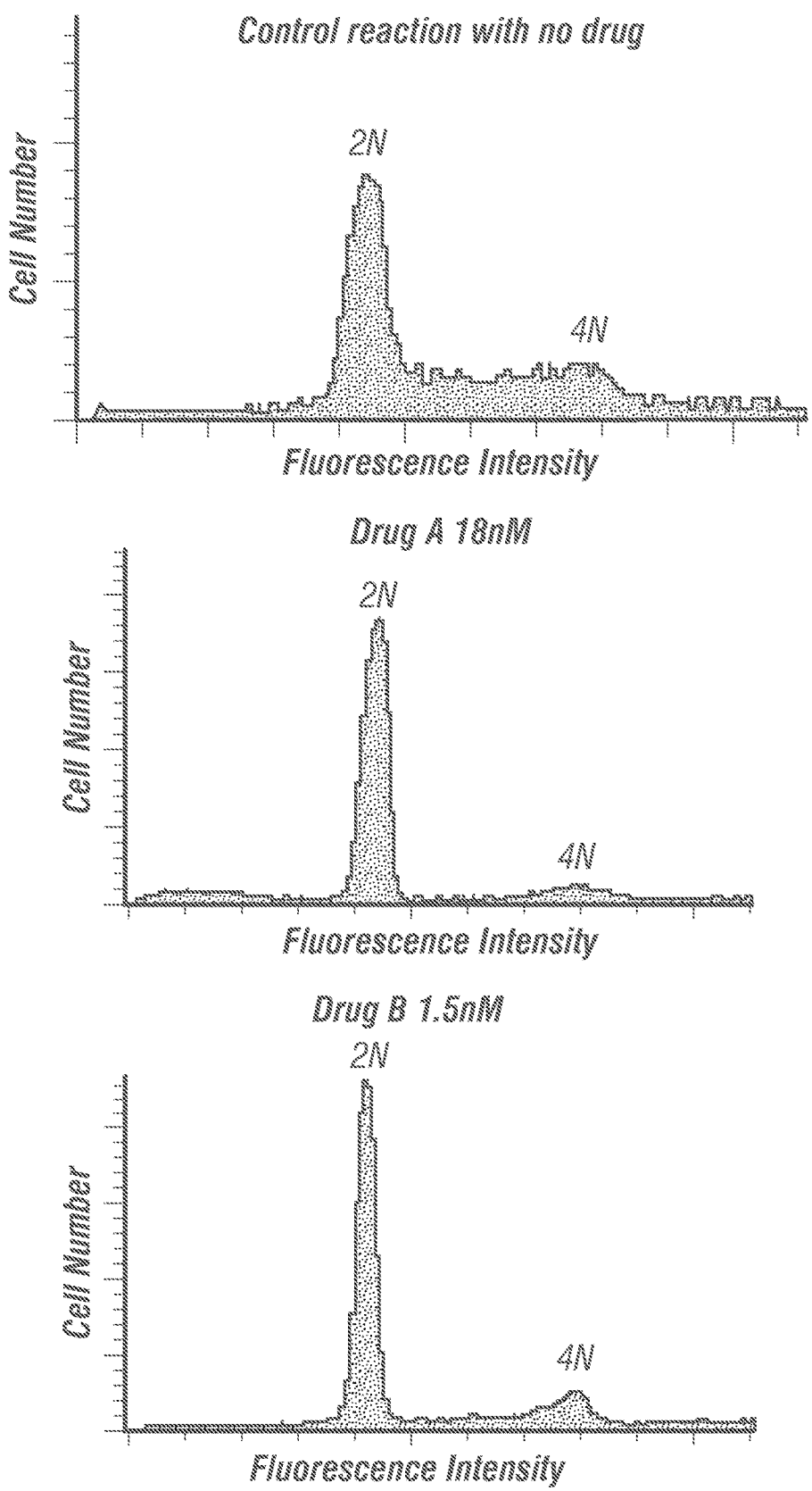
FIG. 3 shows the unedited images as obtained from flow cytometric analysis of six β-lactams (A, B, C, E, F, and L). The noise was cleared. Cell cycle analysis was performed on PANC-1 cells by culturing 100000 cells in DMEM 10% FBS+PS in 35 mm in a petri dish for 72 hrs in the presence of different drugs (A, B, C, E, F, and L) in their respective $IC_{50}$ values (identified by 3D assay, Table E) at 37° C. in a humidified atmosphere of 10% $CO_2$ in 1 mL media. After 72 hrs all the cells (including floaters) were collected, the adhered cells were trypsinized and collected as well. The cells were then centrifuged in a 50 mL centrifuge tube. The pellet was washed with PBS and reconstituted in 500 μL PBS. The cells were then fixed in ice cold ethanol by adding the ethanol dropwise while gently vortexing the cells. Stored at 4° C. for overnight. The cells were then centrifuged, and the pellet reconstituted in Guava cell cycle reagent and analyzed in a Guava flow cytometer. A similar experiment was conducted with normal pancreatic ductal epithelial cells (NPC) and the drug treatment was done according to the $IC_{50}$ values observed in the 2D assay conducted on them (Table E). Please note that 2N represents G0/G1 and 4N for G2 phases.
Figure 3:
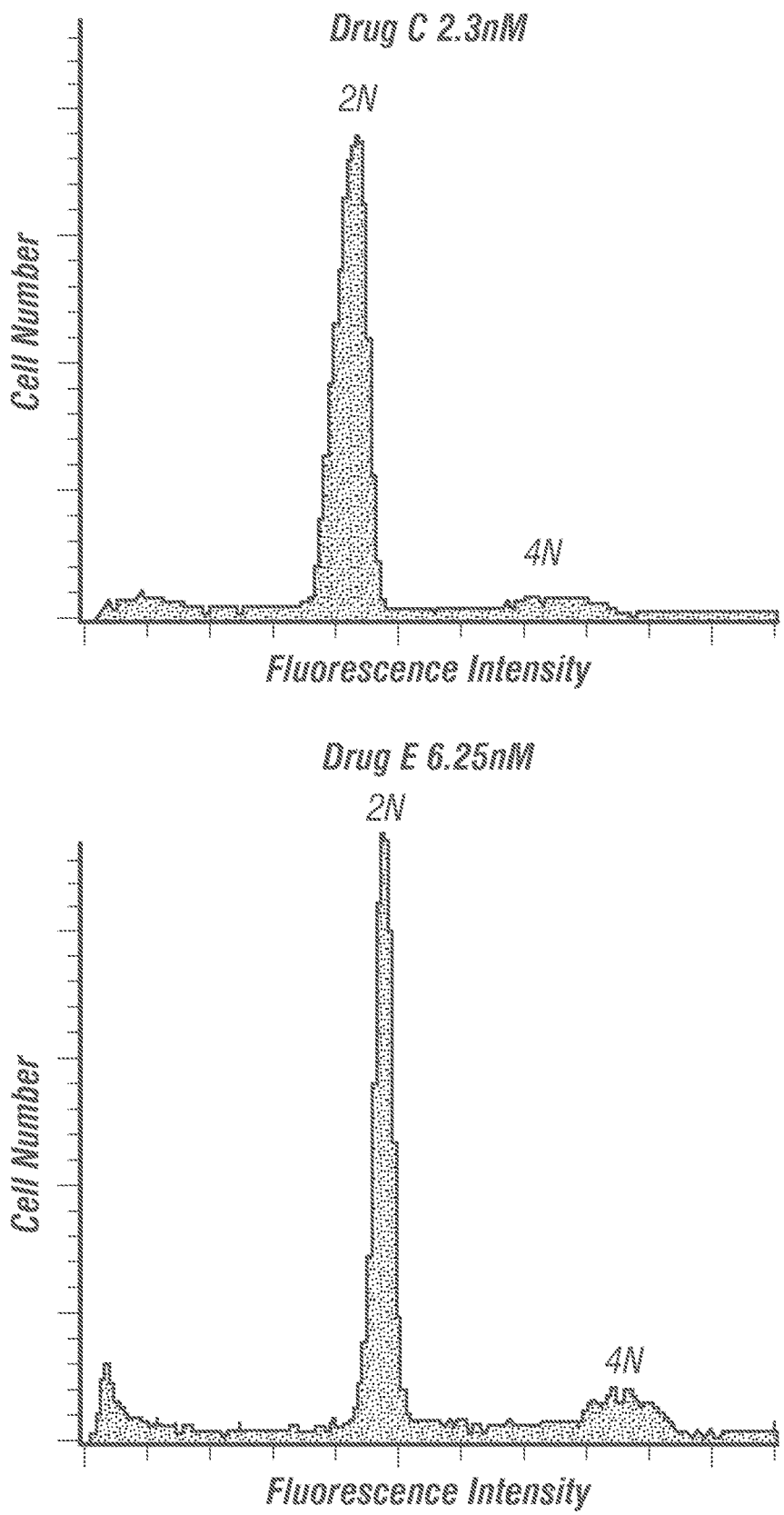
Figure 3:
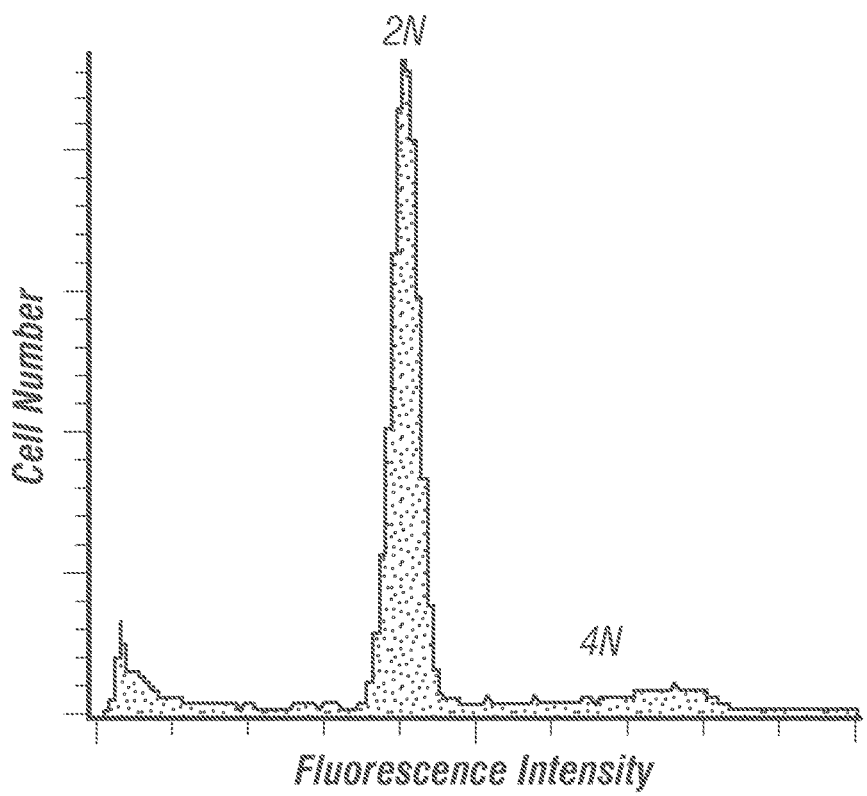
Figure 3:
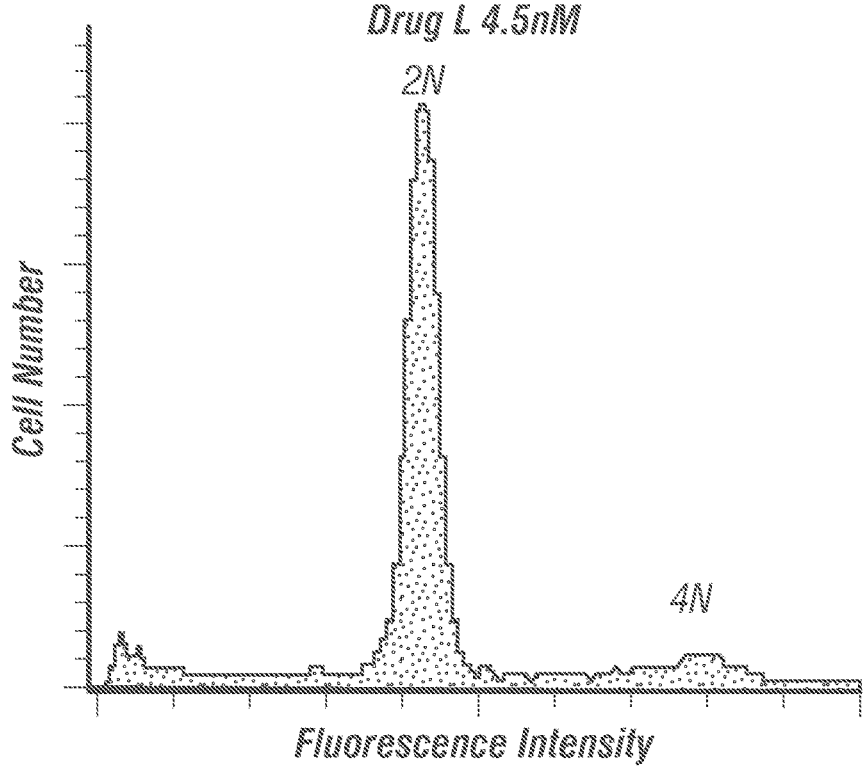
Figure 4A:
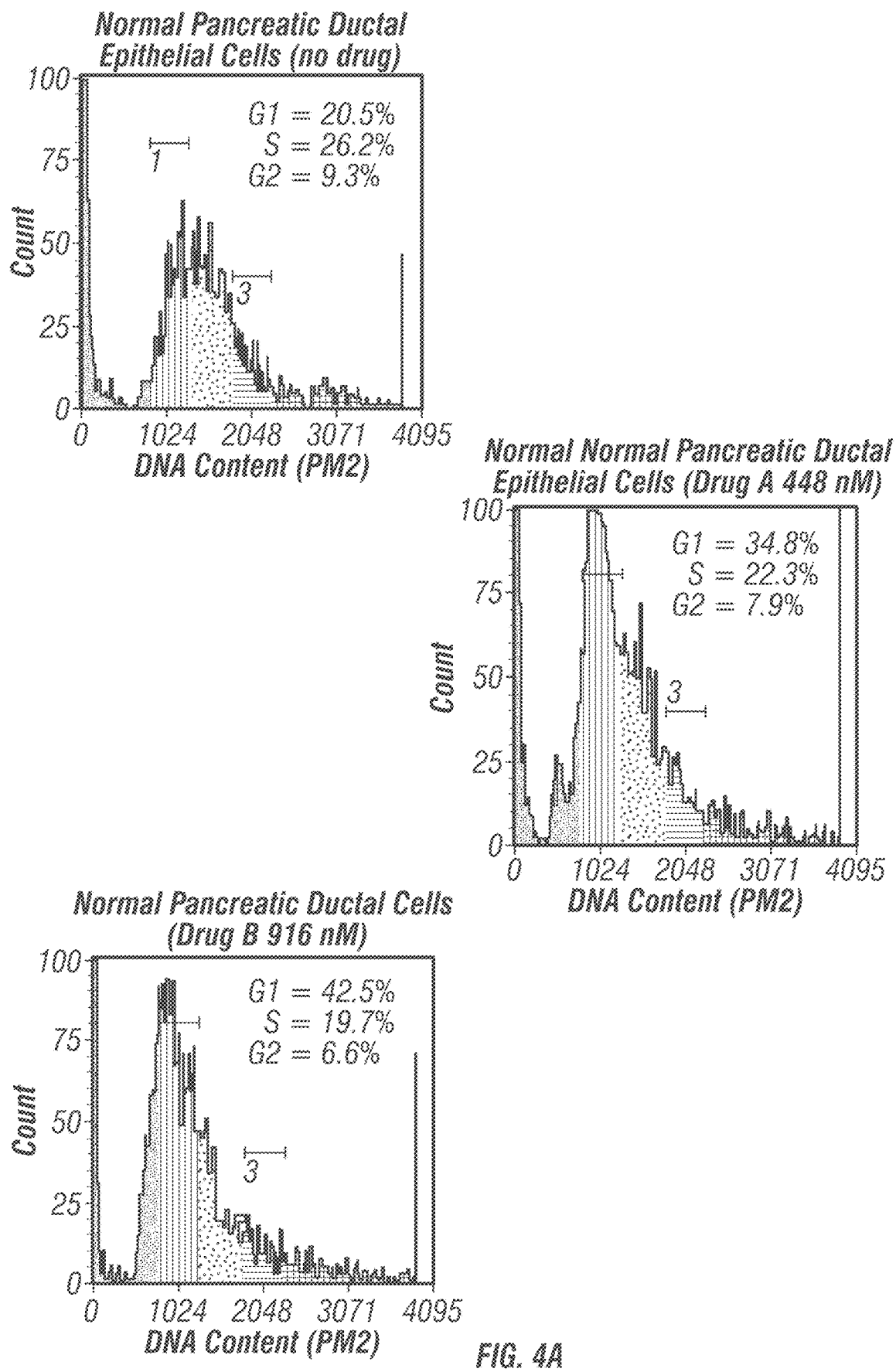
FIGS. 4A-4B show the raw images for both normal and PANC-1 cancer cell lines as obtained from the Guava Flow cytometer. The purpose of this experiment was to figure out if the tested molecule was a G0/G1 blocker or a G2 blocker. The results confirmed that all the six investigational β-lactams are G0/G1 blockers at their respective $IC_{50}$ concentrations that work through blocking DNA replication.
Figure 4A:
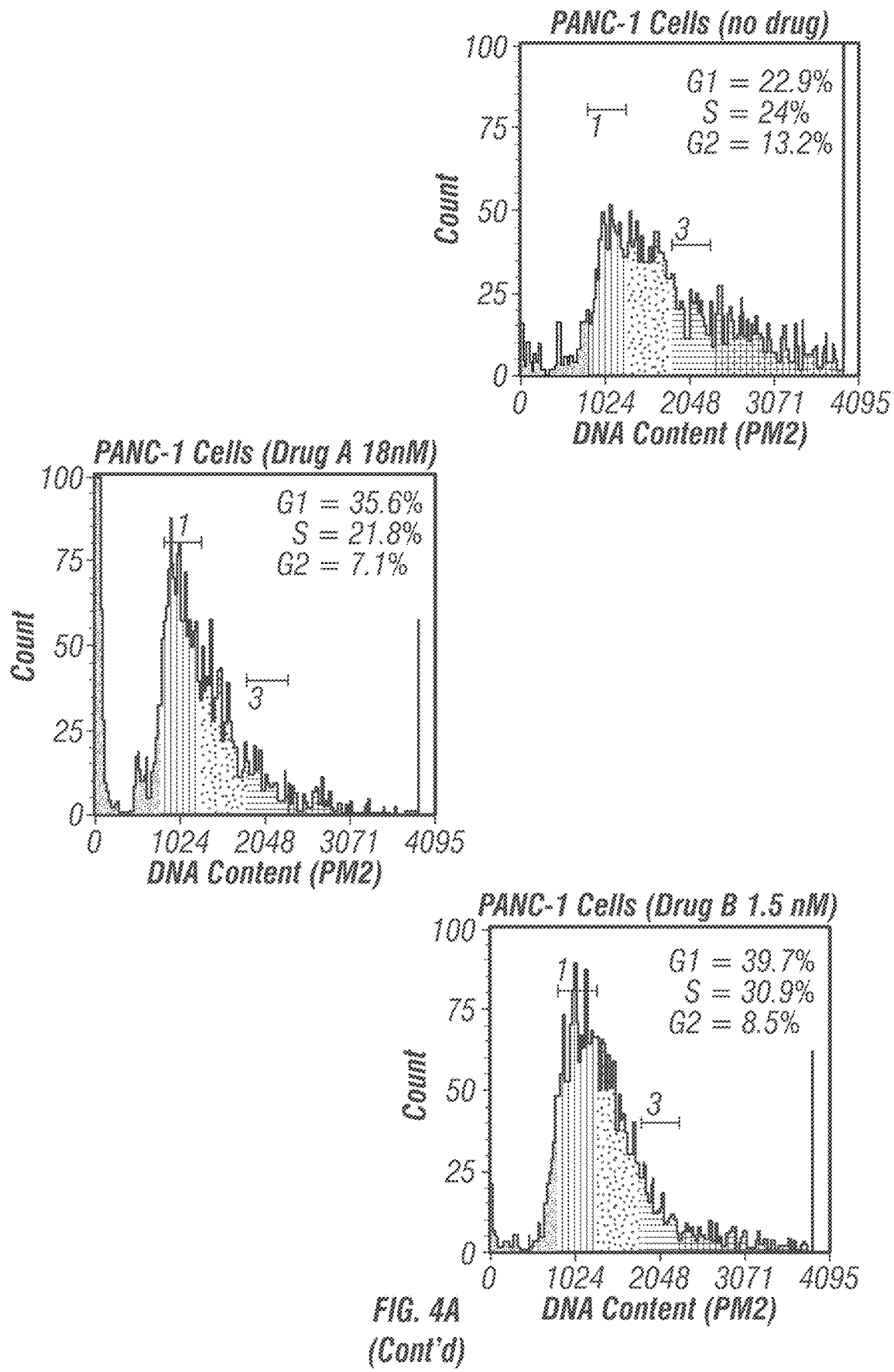
Figure 4B:
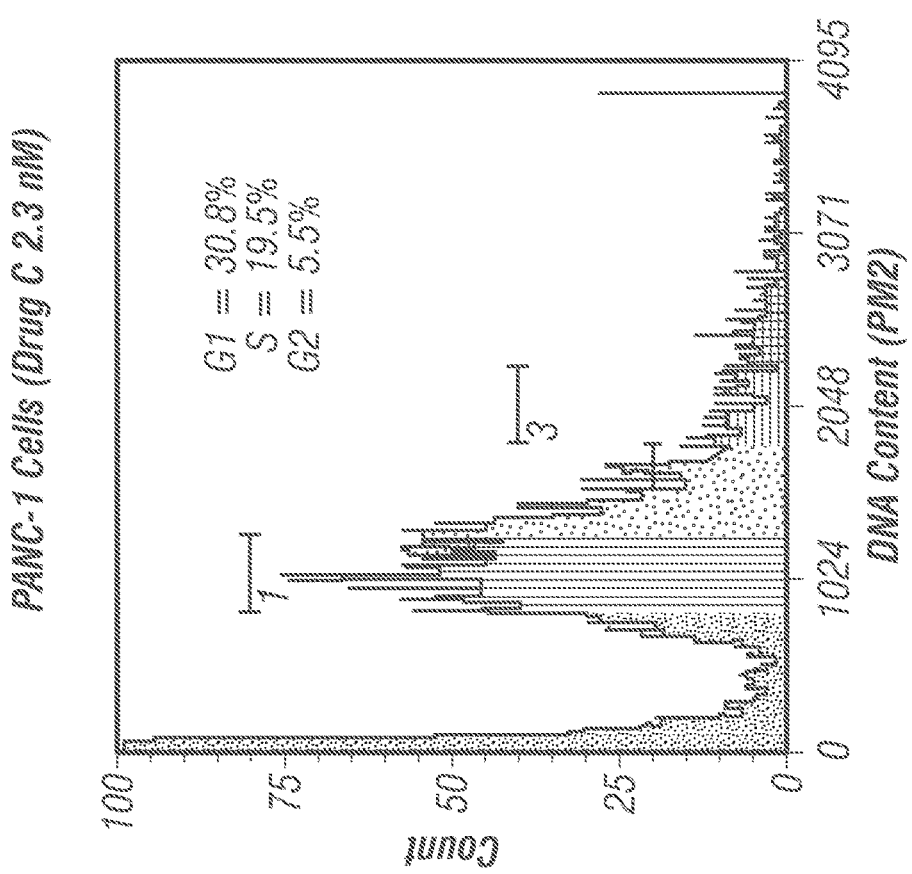
Figure 4B:
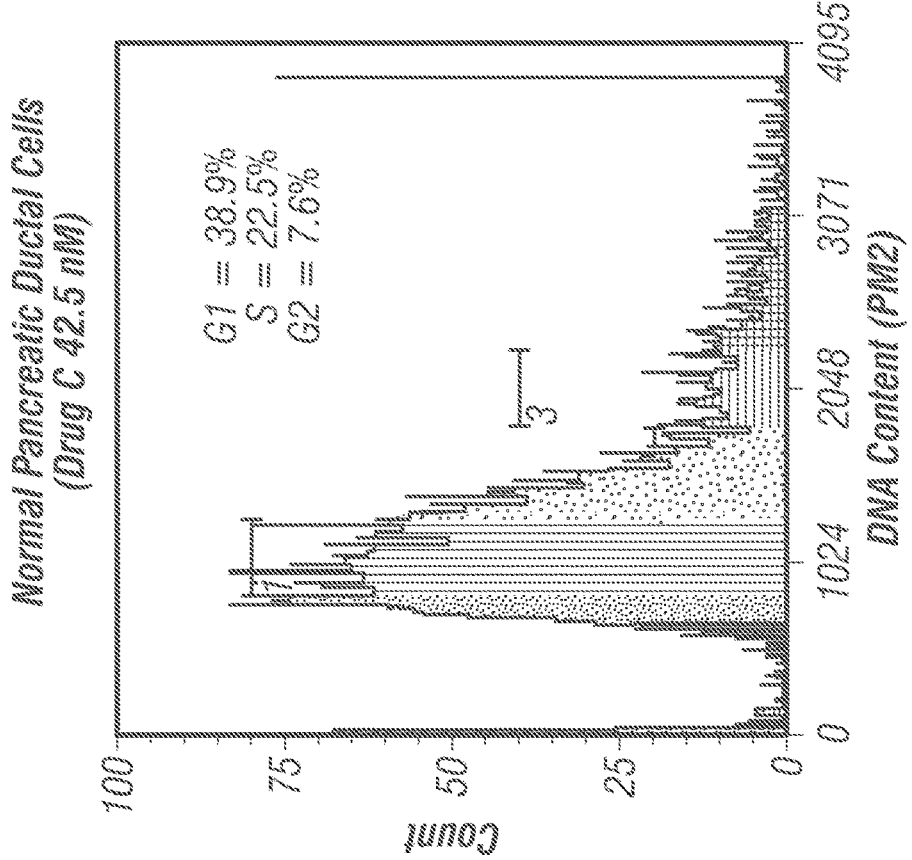
Figure 4B:
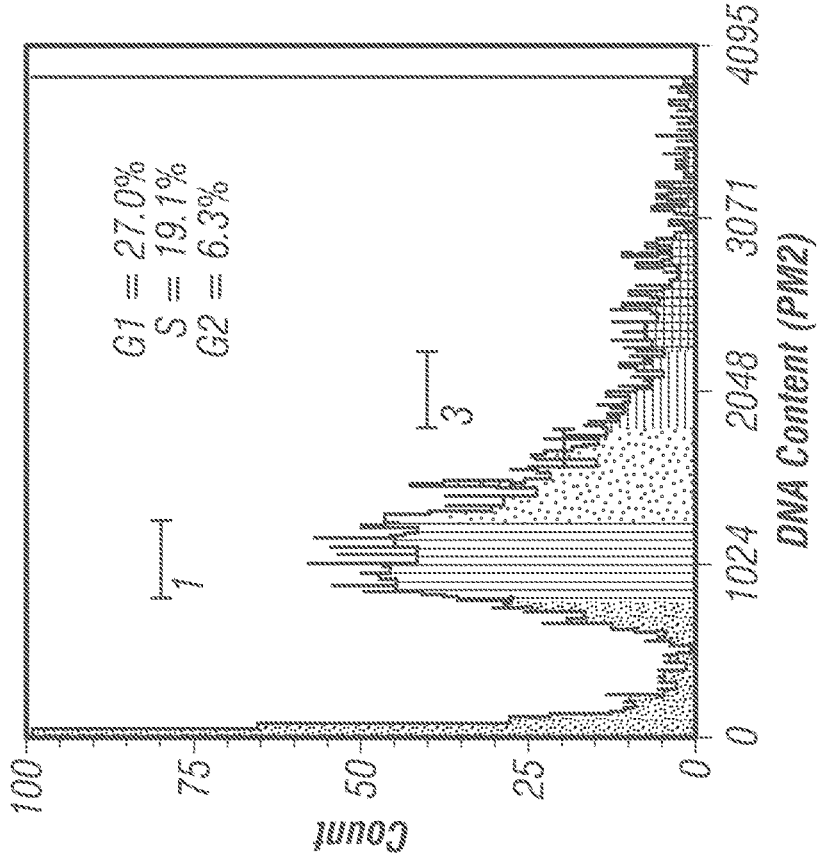
Figure 4B:
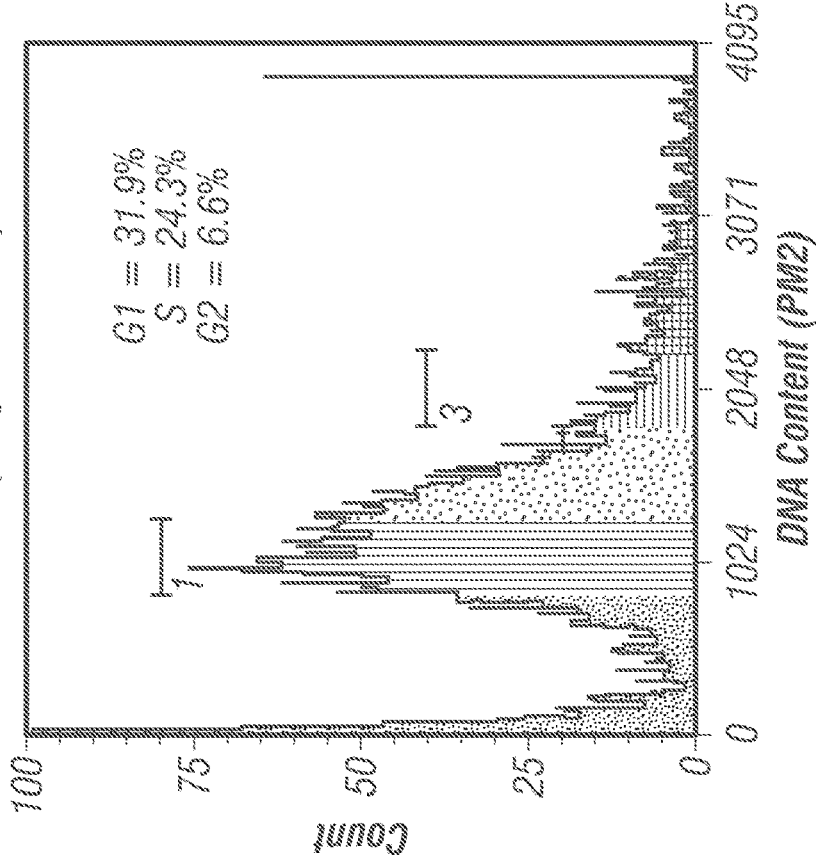
Figure 4B:
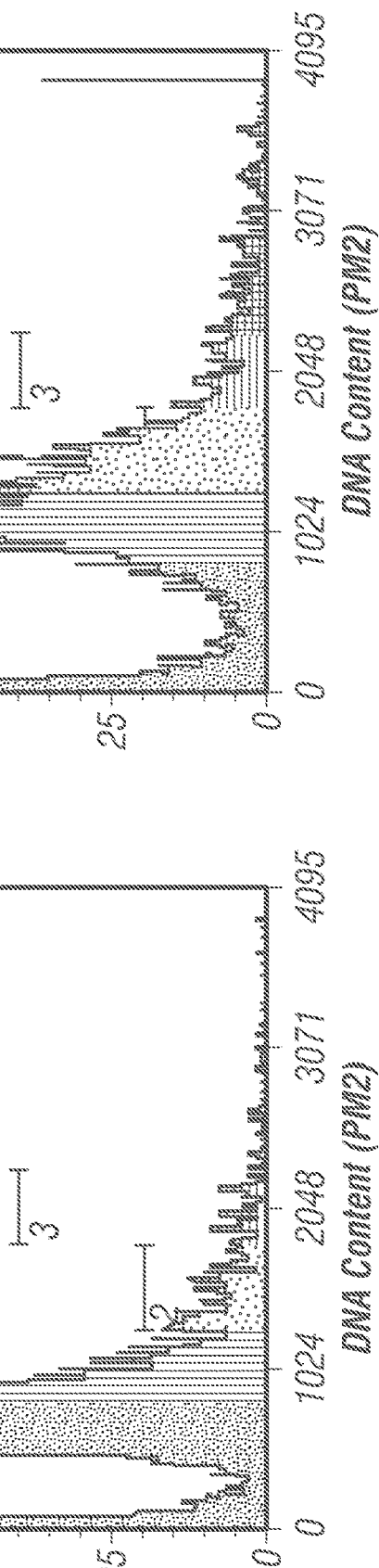
Figure 4B:
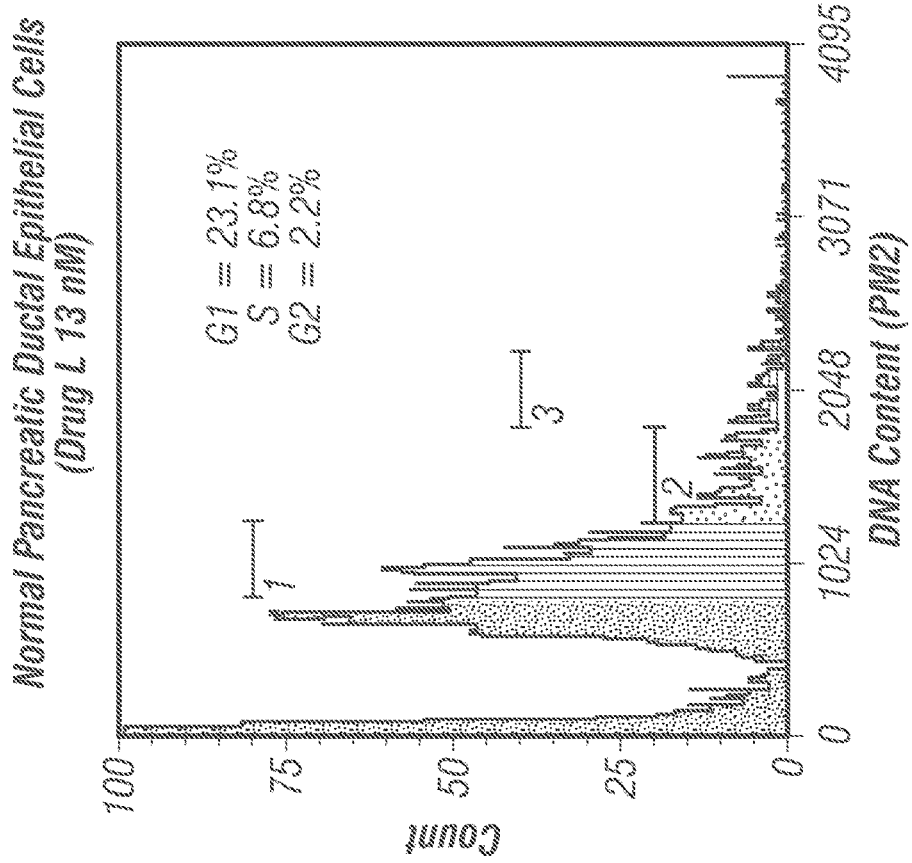

E. Flow Cytometric Analysis of the Compounds a, B, C, E, F, and L in PANC1 Cells Cell cycle analysis was performed on PANC-1 cells by culturing 100000 cells in DMEM 10% FBS+PS in 35 mm in a petri dish for 72 hrs in the presence of different drugs (A, B, C, E, F, and L) in their respective IC$_{50}$ values (identified by 3D assay, Table E) at 37° C. in a humidified atmosphere of 10% CO$_2$ in 1 mL media. After 72 hrs all the cells (including floaters) were collected, the adhered cells were trypsinized and collected as well. The cells were then centrifuged in a 50 mL centrifuge tube. The pellet was washed with PBS and reconstituted in 500 μL PBS. The cells were then fixed in ice cold ethanol by adding the ethanol dropwise while gently vortexing the cells. Stored at 4° C. for overnight. The cells were then centrifuged, and the pellet reconstituted in Guava cell cycle reagent and analyzed in a Guava flowcytometer. The experiment was initially conducted with two drugs A and L for 24, 48 and 72 hrs and maximum cell cycle blockage was observed at 72 hrs. A similar experiment was conducted with normal pancreatic ductal epithelial cells (NPC) and the drug treatment was done according to the IC$_{50}$ values observed in the 2D assay conducted on them (Table E). The unedited raw images from the Guava Flowcytometer are presented in FIGS. 3 and 4A-4B. Please note that 2N represents G0/G1 and 4N for G2 phases. The results confirm that all the six investigational β-lactams are G0/G1 blockers at their respective IC$_{50}$ concentrations that work through blocking DNA replication. First set of data with PANC-1 cells were analyzed by using FlowJo software, the noise was cleared (FIG. 3). The purpose of this experiment was to figure out if the tested molecule was a G0/G1 blocker or a G2 blocker. The second set contains raw data with both normal and PANC-1 cancer cell lines (FIGS. 4A-4B).

F. Annexin V Assay to Determine Apoptosis

Figure 5:
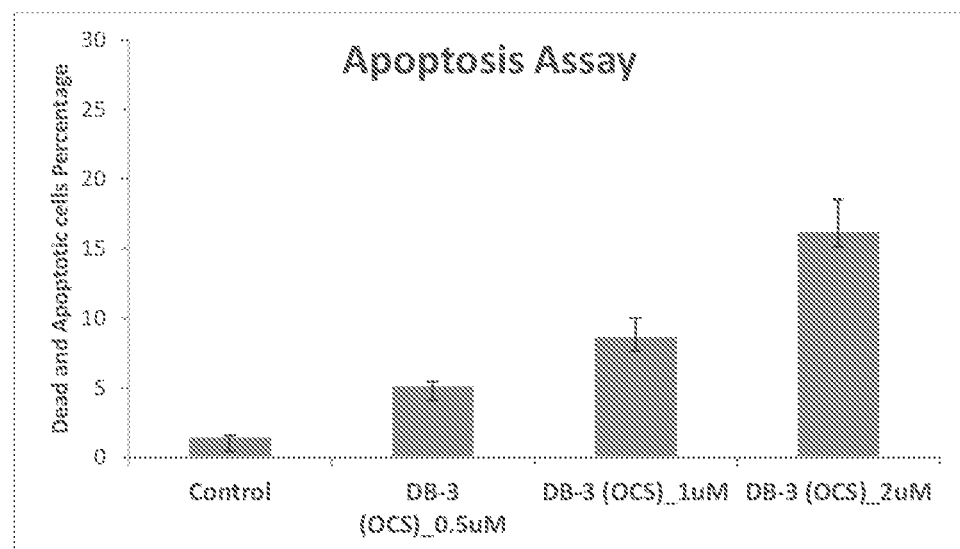
FIG. 5 shows Annexin V assay of compound D with PANC-1 cell lines to determine apoptosis. Cell death was identified as apoptosis through Annexin V assay. For this study, PANC-1, the most commonly known drug-resistance pancreatic cancer cell line was used. PANC-1 cells were treated with 0.5, 1, and 2 μM concentrations of the compound "D" for brief shock of 16 hrs and the cytotoxicity was measured by apoptosis assay. Error bars show standard deviation (n=3). For optimal throughput, final cell concentrations were maintained between $2 \times 10^4$ and $1 \times 10^5$ cells/well (or $1 \times 10^5$ to $5 \times 10^5$ cells/mL). Doxorubicin was used as control at a concentration of 5 μM for 16 hrs.

Prior to the determination of IC-$_{50}$ values in normal pancreatic ductal epithelial cells, the compound D was arbitrarily chosen as a representative compound to determine the mechanism of cell death. The cell death was identified as apoptosis (FIG. 5) through Annexin V assay. For this study, PANC-1, the most commonly known drug-resistance pancreatic cancer cell lines were used. PANC-1 cells were treated with 0.5, 1, and 2 μM concentrations of compound D for brief shock of 16 hrs and the cytotoxicity was measured by apoptosis assay. Error bars show standard deviation (n=3). For optimal throughput, final cell concentrations were maintained between 2×10$^4$ and 1×10$^5$ cells/well (or 1×10$^5$ to 5×10$^5$ cells/mL). Doxorubicin was used as a control at a concentration of 5 uM for 16 hrs (FIG. 5). Apoptosis was identified as the mechanism of cell death.

G. Immunocytochemistry-Immunofluorescence (ICC-IF) with Phospho-Histone H2A.X (Ser139)

Figure 6:
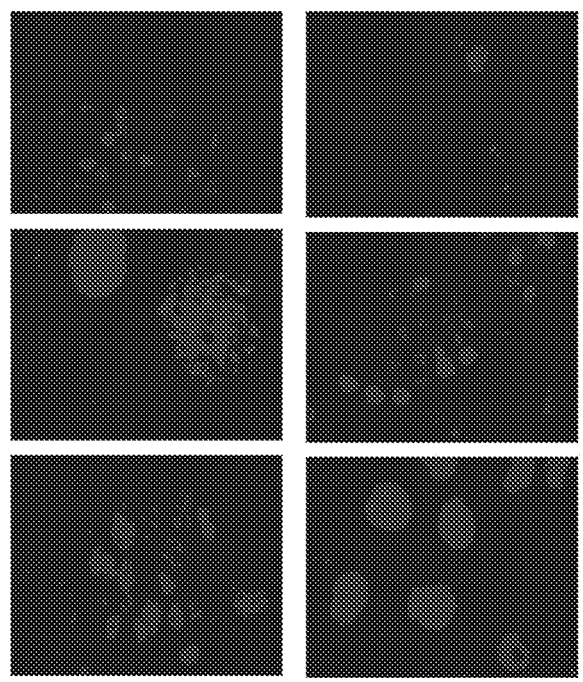
FIG. 6 shows γ-H2AX staining of compound D [DB-3 (OCS)]. This immunocytochemistry-immunofluorescence (ICC-IF) with Phospho-Histone H2A.X (Ser139) assay enables the quantitative detection of the histone variant H2AX, phosphorylated on serine 139. This modification serves as a sensitive biomarker for the detection of such breaks, localizing the site of DNA repair. Gamma-H2AX triggers cell cycle arrest and DNA damage response repair, and this assay is used to study genome stability, the cell cycle, DNA repair, and it serves as a biomarker for cancer and offers enhanced convenience over other immunoassay technologies. The PANC-1 cells were grown, treated with 1 μM concentration of the compound "D", fixed and strained directly in chamber slides. Cells were submerged with blocking buffer for 60 min and then incubated with primary antibody Phospho-Histone H2A.X (Ser139) for overnight at 4° C. Then the cells were rinsed for three times in 1×PBS for 5 min each. The specimen was incubated in fluorochrome-conjugated secondary antibody diluted in antibody dilution buffer for 1-2 h at room temperature in the dark and then rinsed for three times in 1×PBS for 5 min each. Coverslip slides with Prolong® Gold Antifade reagent were visualized under microscope. Red fluorophore/Alexa Fluor® 594 has been used for Gamma-H2AX staining.

This assay was also performed with the compound D, prior to the determination of IC$_{50}$ values in normal pancreatic ductal epithelial cell lines. This assay enables the quantitative detection of the histone variant H2AX, phosphorylated on serine 139. The double-stranded DNA can be broken by ionizing radiation as well as by endogenous physiological processes, H2AX becomes phosphorylated at Ser139. This modification, called gamma-H2AX (phospho-Ser139), serves as a sensitive biomarker for the detection of such breaks, localizing the site of DNA repair. Gamma-H2AX triggers cell cycle arrest and DNA damage response repair, and this assay is used to study genome stability, the cell cycle, DNA repair, and it serves as a biomarker for cancer and offers enhanced convenience over other immunoassay technologies. The PANC-1 cells were grown, treated with 1 μM concentration of the compound D, fixed and strained directly in chamber slides. The steps are as follows: Cells were submerged with blocking buffer for 60 min and then incubated with primary antibody (Phospho-Histone H2A.X (Ser139) for overnight at 4° C. Then the cells were rinsed for three times in 1×PBS for 5 min each. The specimen was incubated in fluorochrome-conjugated secondary antibody diluted in antibody dilution buffer for 1-2 h at room temperature in the dark and then rinsed for three times in 1×PBS for 5 min each. Coverslip slides with Prolong® Gold Antifade reagent were visualized under microscope. Red fluorophore/Alexa Fluor® 594 was used for Gamma-H2AX staining. Results are shown in FIG. 6.

Histones are elementary nuclear proteins that comprise the structure of nucleosome, a basic unit of DNA. Two molecules of each of the four core histones (H2A, H2B, H3, and H4) form an octamer and each histone octamer is wrapped with approximately 146 DNA base pairs in 1.67 left-handed superhelical turns around a histone octamer. Phospho-H2AX or γ-H2AX is an authentic marker of DNA damage through double-stranded breaks that can be stained for. In this experiment, positive staining is an indication of genomic instability due to telomere dysfunction in cancer cells (telomere is a specific nucleoprotein complex that wraps the terminals of eukaryotic chromosome). Telomere dysfunction triggers the canonical DNA damage response pathway that engages p53 to initiate apoptosis. The positive staining (with red fluorophore/Alexa Fluor® 5941) is visible by phospho-H2AX foci-dots in the nucleus of the compound D treated PANC-1 cell lines. Taken together, the dots (FIG. 6, right) are indicative of telomere dysfunction and subsequent DNA damage, followed by apoptosis and eventually death of compound D treated PANC-1 cells in comparison to the control (left).

H. BrdU (5-Bromo-2'-Deoxyuridine) Incorporation to Proceed with Immunostaining

Diluted BrdU in fresh, pre-warmed growth medium to a final concentration of 0.03 mg/mL. This mixture was added to cells and incubated at 37° C. for 30 min. The medium was aspirated; cells were completely covered with 70% ethanol for 5 min. The fixative was aspirated and the cells were rinsed three times in 1×PBS for 5 min each. Therefore, 1.5 mL HCl and incubated for 30 min at room temperature. Then the HCl was aspirated and rinsed to times in 1×PBS for 5 min each. Subsequent proceeding for immunostaining followed the below steps: The cells were submerged with blocking buffer for 60 min and subsequently incubated with primary antibody (BrdU Mouse mAb) for overnight at 4° C. Therefore, the cells were rinsed three times in 1×PBS for 5 min each and incubated in fluorochrome-conjugated secondary antibody diluted in antibody dilution buffer for 1-2 h at room temperature in the dark and then rinsed for three times in 1×PBS for 5 min each. Coverslip slides with Prolong® Gold Antifade reagent were visualized under microscope. Alexa Fluor® 488 (green) has been used for BrdU staining along with nuclear marker DAPI (blue). BrdU images were co-localized with nuclear marker DAPI blue. Highly promising result was obtained (FIG. 7).

5'-bromo-2'-deoxyuridine (BrdU) is an analog of the DNA nucleoside thymidine. Thymidine and BrdU have the identical structure except in place of a methyl ($CH_3$) in thymidine there is a bromine (Br) at C-5 in BrdU. BrdU incorporation is a highly explored assay to determine cell proliferation rates in a wide variety of species from plants to mammals. Because of structural identity, BrdU is incorporated (instead of thymidine) in the replicating cells, during the S-phase of the cell cycle (when DNA is replicated) into newly synthesized DNA. Incorporation of BrdU was detected with anti-BrdU antibodies (BrdU Mouse mAb) and subsequent incubation with fluorochrome-conjugated secondary antibody. BrdU specific antibodies were detected by staining with Alexa Fluor® 488 (green) along with nuclear marker DAPI (blue) to identify cells that were actively replicating their DNA. For successful staining, a DNA denaturing step is included to allow the antibody access to the incorporated BrdU. DAPI (4',6-diamidino-2-phenylindole) was used as a secondary stain to provide contrast that helped the primary stain (Alexa Fluor® 488) be prominent. Most amazingly, the FIG. 7 clearly shows the rate of DNA replication and subsequent cell proliferation were significantly low in compound D treated PANC-1 cells (right, only a few blue dots) in comparison to the control (left).

All the compounds, compositions, and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compounds, compositions, and methods without departing from the spirit, scope, and concept of the invention. All variations and modifications apparent to those skilled in the art are deemed to be within the spirit, scope, and concept of the invention as defined by the appended claims.

REFERENCES

The following references to the extent that they provide exemplary procedural or other details supplementary to those set forth herein, are specifically incorporated herein by reference.
U.S. Pat. No. 8,946,409
PCT Pub. WO 2012/103456
Anderson, *Practical Process Research & Development—A Guide for Organic Chemists*, 2$^{nd}$ ed., Academic Press, New York, 2012.
Furuya et al., *Nature*, 473:470, 2011
Garcia et al., *J. Clin. Invest.*, 124(11):4709-22, 2014.
*Handbook of Pharmaceutical Salts: Properties, and Use*, Stahl and Wermuth Eds., Verlag Helvetica Chimica Acta, 2002.
Johnson et al., *Bio. Protoc.*, 3(3): e325, 2013.
Mazur et al., *Nature*, 510(7504):283-87, 2014.
Reagan-Shaw et al., *FASEB J.*, 22(3):659-661, 2008.
Smith, *March's Advanced Organic Chemistry: Reactions, Mechanisms, and Structure*, 7$^{th}$ Ed., Wiley, 2013.

What is claimed is:

1. A compound of the formula:

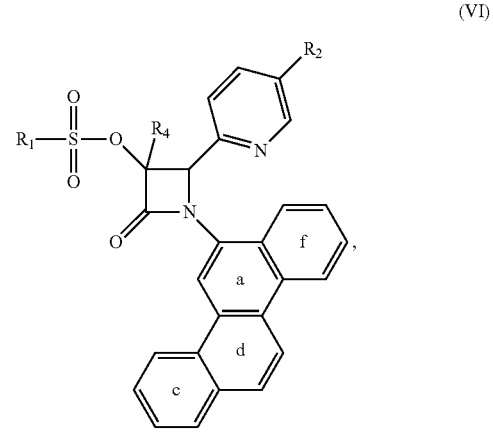

(VI)

wherein:
$R_1$ is hydrogen, hydroxy, amino, or isocyanyl; or
alkyl$_{(C≤12)}$, cycloalkyl$_{(C≤12)}$, alkenyl$_{(C≤12)}$, cycloalkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, alkylamino$_{(C≤12)}$, dialkylamino$_{(C≤12)}$, heterocycloalkyl$_{(C≤12)}$, or a substituted version of any of these groups;
$R_2$ is halo, hydroxy, or amino; or
alkoxy$_{(C≤12)}$, acyloxy$_{(C≤12)}$, alkylamino$_{(C≤12)}$, dialkylamino$_{(C≤12)}$, or a substituted version of any of these groups; and
$R_4$ is amino, azido, cyano, halo, hydrogen, or hydroxy; or
alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, alkoxy$_{(C≤12)}$, aryloxy$_{(C≤12)}$, aralkoxy$_{(C≤12)}$, acyloxy$_{(C≤12)}$, alkylamino$_{(C≤12)}$, dialkylamino$_{(C≤12)}$, amido$_{(C≤12)}$, or a substituted version of any of these groups;
or a pharmaceutically acceptable salt or tautomer thereof.

2. The compound of claim 1, wherein $R_2$ is fluoro.

3. The compound of claim 1, wherein $R_4$ is hydrogen.

4. The compound of claim 1, wherein $R_1$ is hydrogen, hydroxy, amino, or isocyanyl.

5. The compound of claim 4, wherein $R_1$ is isocyanyl.

6. The compound of claim 1, wherein $R_1$ is methyl, 2,2,2-trifluoroethyl, 3-cyanoazetidine, cyclobutyl, isopropyl (methyl)amino, cyclopropyl, 4-methylpiperizinyl, pyrrolidinyl, dimethylamino, or tolyl.

7. The compound of claim 1, wherein the carbon atom 3 is in the S conformation.

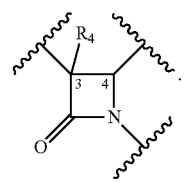

8. The compound of claim 1, wherein the carbon atom 4 is in the S conformation.

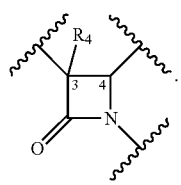
9. The compound of claim 1, wherein the compound is further defined as:
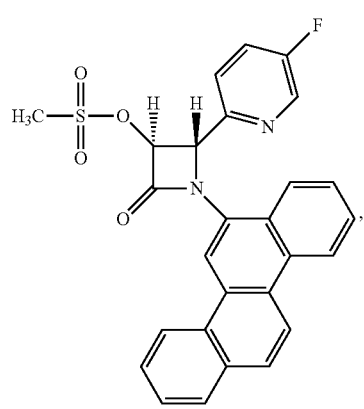
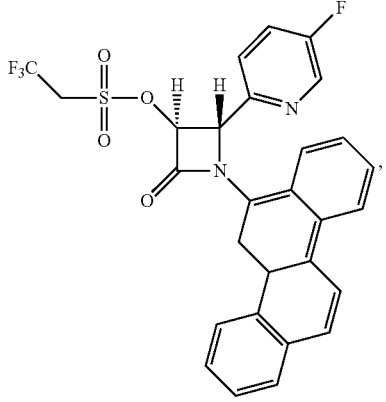
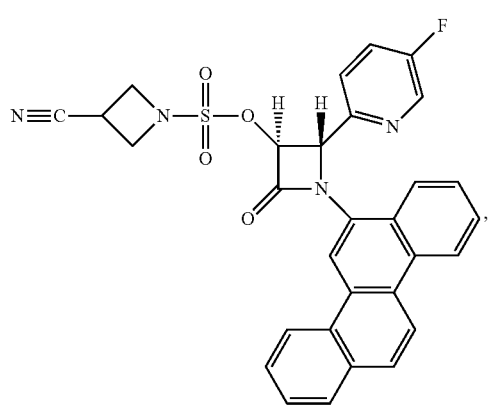
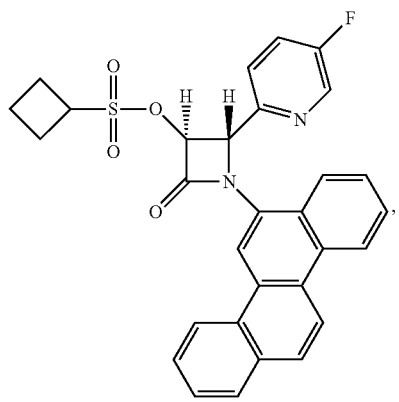
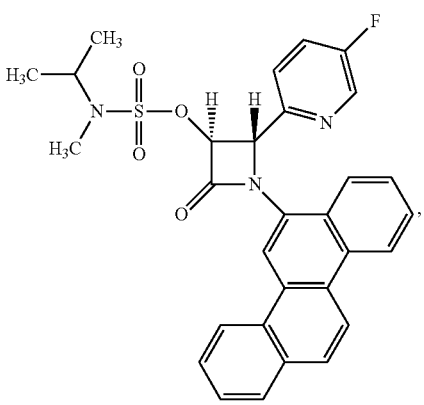
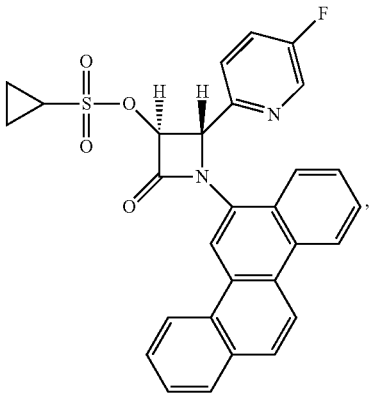
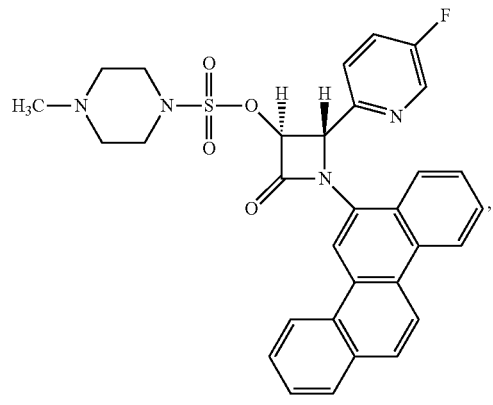

-continued

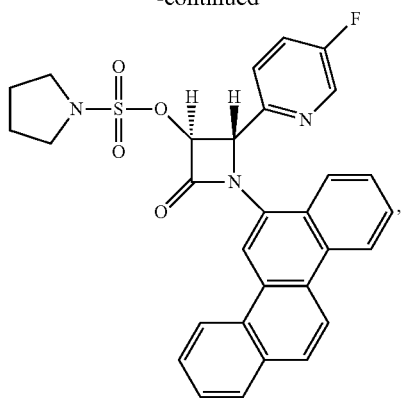

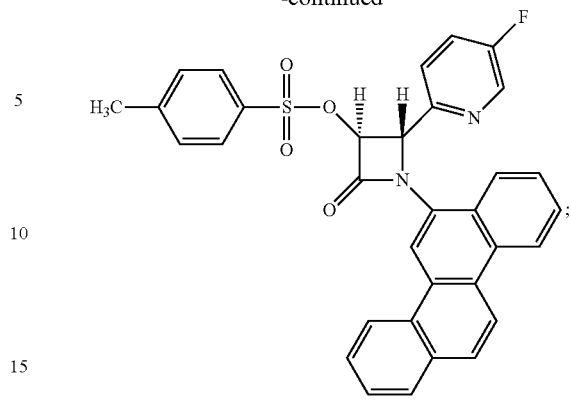

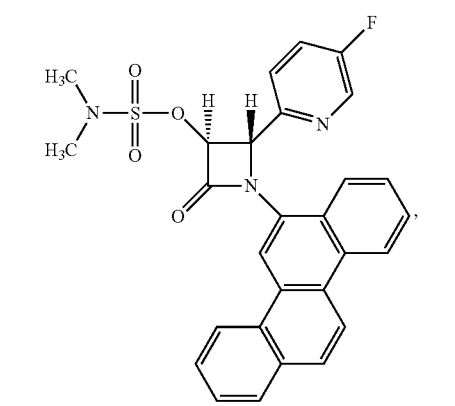, or or a pharmaceutically acceptable salt or tautomer thereof.

10. A pharmaceutical composition comprising:
(a) a compound of claim 1; and
(b) an excipient.

11. A method of treating KRAS-dependent disorder in a patient in need thereof comprising administering to the patient a therapeutically effective amount of a compound of claim 1.

12. The method of claim 11, wherein the KRAS-dependent disorder is cancer.

13. The method of claim 12, wherein the cancer is pancreatic cancer.

14. The method of claim 13, wherein the pancreatic cancer is resistant to treatment with gemcitabine.

15. The compound of claim 1, wherein the compound is further defined as:

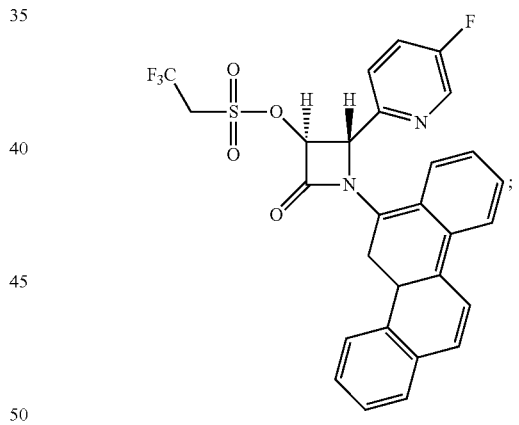

or a pharmaceutically acceptable salt or tautomer thereof.

* * * * *